(12) United States Patent
Flynn et al.

(10) Patent No.: US 7,279,576 B2
(45) Date of Patent: Oct. 9, 2007

(54) ANTI-CANCER MEDICAMENTS

(75) Inventors: Daniel L. Flynn, Lawrence, KS (US); Peter A. Petillo, Arlington, MA (US)

(73) Assignee: Deciphera Pharmaceuticals, LLC, Lawrence, KS (US)

( * ) Notice: Subject to any disclaimer, the term of this patent is extended or adjusted under 35 U.S.C. 154(b) by 162 days.

(21) Appl. No.: 10/746,607

(22) Filed: Dec. 24, 2003

(65) Prior Publication Data

US 2004/0176395 A1    Sep. 9, 2004

Related U.S. Application Data

(60) Provisional application No. 60/463,804, filed on Apr. 18, 2003, provisional application No. 60/437,487, filed on Dec. 31, 2002, provisional application No. 60/437,403, filed on Dec. 31, 2002, provisional application No. 60/437,415, filed on Dec. 31, 2002, provisional application No. 60/437,304, filed on Dec. 31, 2002.

(51) Int. Cl.
C07D 239/02    (2006.01)

(52) U.S. Cl. ............... 544/322; 544/330; 544/331; 544/122

(58) Field of Classification Search ............ 544/322, 544/330, 331, 122
See application file for complete search history.

(56) References Cited

U.S. PATENT DOCUMENTS

| | | | |
|---|---|---|---|
| 4,296,237 A | 10/1981 | Cragoe, Jr. | |
| 4,366,189 A | 12/1982 | Burdeska et al. | |
| 4,432,992 A | 2/1984 | Cragoe, Jr. et al. | |
| 5,103,014 A | 4/1992 | Musser et al. | |
| 5,494,925 A | 2/1996 | Court et al. | |
| 6,020,357 A | 2/2000 | Pinto et al. | |
| 6,166,219 A | 12/2000 | Yamasaki et al. | |
| 6,235,786 B1 | 5/2001 | Dai et al. | |
| 6,294,573 B1 | 9/2001 | Curtin et al. | |
| 6,319,921 B1 | 11/2001 | Cirillo et al. | |
| 6,352,985 B1 | 3/2002 | Yamasaki et al. | |
| 2001/0008898 A1 | 7/2001 | Tomiyama et al. | |
| 2003/0181411 A1 | 9/2003 | Bosch et al. | |
| 2003/0186221 A1 | 10/2003 | Lockhart et al. | |
| 2005/0288286 A1* | 12/2005 | Flynn et al. ............ 514/235.2 |

FOREIGN PATENT DOCUMENTS

| CA | 2134915 | 11/1993 |
|---|---|---|
| DE | 2 156 343 | 5/1972 |
| DE | 2 341 064 | 3/1974 |
| DE | 4302702 | 8/1994 |
| DE | 4337847 | 5/1995 |
| DE | 4343831 | 6/1995 |
| DE | 44 14 840 A1 | 11/1995 |
| DE | 4414840 | 11/1995 |
| EP | 0021228 | 1/1981 |
| EP | 0025232 | 3/1981 |
| EP | 0739884 | 10/1996 |
| EP | 0867435 | 9/1998 |
| EP | 0927555 | 7/1999 |
| EP | 0956855 | 11/1999 |
| EP | 1281399 | 2/2003 |
| FR | 2 337 554 | 8/1977 |
| FR | 2 396 549 | 2/1979 |
| GB | 971307 | 9/1964 |
| GB | 1127875 | 3/1967 |
| GB | 2276161 | 9/1984 |
| GB | 2220206 | 1/1990 |
| JP | 59-15247 | 1/1984 |
| JP | 59-177557 | 10/1984 |
| JP | 9-221476 | 8/1997 |
| JP | 10-7804 | 1/1998 |
| JP | 11-209350 | 8/1999 |
| JP | 2000-275886 | 10/2000 |
| JP | 2001-2687 | 1/2001 |
| WO | WO9119708 | 12/1991 |
| WO | WO9208693 | 5/1992 |
| WO | WO9424095 | 10/1994 |
| WO | WO9515954 | 6/1995 |
| WO | WO9534540 | 12/1995 |
| WO | WO9616046 | 5/1996 |
| WO | WO9619477 | 6/1996 |
| WO | WO9734900 | 9/1997 |
| WO | WO9822103 | 5/1998 |
| WO | WO9915164 | 4/1999 |
| WO | WO9923093 | 5/1999 |
| WO | WO9959959 | 11/1999 |
| WO | WO0002851 | 1/2000 |
| WO | WO0007980 | 2/2000 |
| WO | WO0018738 | 4/2000 |

(Continued)

OTHER PUBLICATIONS

O'Dell, J., et al. "Treatment of Rheumatoid Arthritis with Methotrexate Alone, Sulfasalazine and Hydroxychloroquine, or a Combination of All Three Medications," New. Eng. J. Med., vol. 334(20), pp. 1287-1291 (May 1996), at p. 1287, col. 1, lines 6-9.

Dumas, "Protein Kinase Inhibitors: Emerging From a Pharmacophores 1997-2000", Expert Opinion on Therepeudic Patents, (2001), vol. 11, pp. 405-429.

Schindler et al., "Structural Mechanism for STI-571 Inhibition of Abelson Tyrosine Kinase", Science, (Sep. 15, 2000), vol. 289, pp. 1938-1942.

Pargellis et al., "Inhibition of P38 MAp Kinase by Utilizing a Novel Allosteric Binding Site", Nature Structural Biology, (Apr. 2002), vol. 9, pp. 268-272.

(Continued)

Primary Examiner—Kamal A. Saeed
Assistant Examiner—Rei-tsang Shiao
(74) Attorney, Agent, or Firm—Hovey Williams LLP

(57) ABSTRACT

Novel compounds and methods of using those compounds for the treatment of oncological conditions are provided. In a preferred embodiment, modulation of the activation states of abl or bcr-abl α-kinase proteins comprises the step of contacting the kinase proteins with the novel compounds.

3 Claims, 8 Drawing Sheets

FOREIGN PATENT DOCUMENTS

| WO | WO0021927 | 4/2000 |
|---|---|---|
| WO | WO0041698 | 7/2000 |
| WO | WO0043384 | 7/2000 |
| WO | WO0059506 | 10/2000 |
| WO | WO0112621 | 2/2001 |
| WO | WO0114372 | 3/2001 |
| WO | WO0174771 | 10/2001 |
| WO | WO0196298 | 12/2001 |
| WO | WO0214291 | 2/2002 |
| WO | WO0228835 | 4/2002 |
| WO | WO0234727 | 5/2002 |
| WO | WO0240458 | 5/2002 |
| WO | WO02060869 | 8/2002 |
| WO | WO02060876 | 8/2002 |
| WO | WO03000189 | 1/2003 |
| WO | WO03053368 | 7/2003 |
| WO | WO03059373 | 7/2003 |
| WO | WO03072577 | 9/2003 |

OTHER PUBLICATIONS

Nofal et al., "Synthesis of Novel Uracil-5-Sulphonamide Derivatives of Possible Biological Activity", Egypt Journal of Chemistry, (1990), vol. 33, pp. 375-380.

Johnson et al., "The Stereochemistry Oxidation at Sulfur", Tetrahedron, (1969), vol. 25, pp. 5649-5653.

Griffith et al., "TPAP: Tetra-In-Propylammonium Perruthenate, a Mild and Convenient Oxidant for Alcohols", Aldrichimica Acta, (1990), vol. 23, pp. 13-19.

Zvilichovsky et al., "Aminolysis and Polymerization 3-(p-toluenesulfonoxy) Hydantoin", Israel Journal of Chemistry, (1969), vol. 7, pp. 547-554.

Yang et al., "Palladimum-Catalyzed Amination of Aryl Halides and Sulfonates", Journal of Organlmetallic Chemistry, (1999), vol. 576, pp. 125-146.

Kwong et al., "A General, Efficient, an Inexpensive Catalyst System for the Coupling of Aryl Iodies and Thiols", Organic Letters, (2002), vol. 4, pp. 3517-3520.

Leca et al., "A New Practical 1-Pot Access to Sulfonimidates", Organic Letters, (2002), vol. 4, pp. 4093-4095.

Cheng et al., "Novel Solution Phase Strategy for the Synthesis of Chemical Libraries Containing Small Organic Molecules", Journal American Chemical Society, (1996), vol. 118, pp. 2567-2573.

Dess et al., "A Useful 12-I-5 Triacetoxyperiodinane (the Dess-Martin Periodinane) for the Selective Oxidation of Primary or Secondary Alcohols in a Variety of Related 12-I-5 Species", Journal American Chemical Society , (1991), vol. 113, pp. 7277-7287.

Bausch et al., "Proton-transfer Chemistry of Urazoles and Related Imides, Amides and Diacyl Hydrazides", Journal Organic Chemistry, (1991), vol. 56, pp. 5643-5651.

Muller et al., "A General Synthesis of 4-substituted 1, 1-Dioxo-1, 2, 5-thiadiazolidin-3-ones Derived From a-Amino Acids", The Journal of Organic Chemistry, (1989), vol. 54, pp. 4471-4473.

Klyman et al., "The Reaction of S-Methiodide Derivatives of Activated Thioureas with Hydroxylic Compounds. A Novel Synthesis of Mercaptans", Journal of Organic Chemistry, (1972), vol. 37, pp. 1532-1537S.

Tremblay et al., "Efficient Solid-Phase Synthesis of Sulfahydantoins", Journal of Combinatorial Chemistry, (2002), vol. 4, pp. 429-435.

Peng et al., "Identification of Novel Inhibitors of BCR-ABL Tyrosine Kinase via Virtual Screening", Journal of Bioorganic and Medicinal Chemistry Letters, (2003), vol. 13, pp. 3693-3699.

Huse et al., "Conformational Plasticity of Protein Kinases", Cell, (2002), vol. 109, pp. 275-282.

Teague, "Implications of Protein Flexibility for Drug Discovery", Nature Reviews, (Jul. 2003), vol. 2, pp. 527-541.

Wu et al., "Discovery of a Novel Family of CDK Inhibitors with the Program LIDAEUS: Structural Basis for Ligand-Induced Disordering of the Activation Loop", Structure, (2003), vol. 11, pp. 399-410.

Askew et al., "Molecular Recognition with Convergent Functions Groups. Synthetic Instructural Studies with a Model Receptor for Nucleic Acid Components", Journal of American Chemical Society, (1989), vol. 111, pp. 1082-1090.

Regan et al., "Pyrazole Urea-Based Inhibitors of p38MAP Kinase: From Lead Compound to Clinical Candidate", Journal of Medicinal Chemistry, (2002), vol. 45, pp. 2994-3008.

Venter, et al., "The Sequence of the Human Genome", Science, (2001), vol. 291, pp. 1304-1351.

"Initial Sequencing and Analysis of the Human Genome", Nature, (2001), vol. 409, pp. 860-921.

Wollter et al., "Copper-Catalyzed Coupling of Aryl Iodides with Aliphatic Alcohols", Organic Letters, (2002), vol. 4, pp. 973-976.

Martinez et al., "First Non-ATP Competitive Glycogen Synthase Kinase 3β (GSK-3β) Inhibitors: Thiadiazolidinones (TDZD) as Potential Drugs for the Treatment of Alzheimer's Disease", Journal of Medicinal Chemistry , (2002), vol. 45, pp. 1292-1299.

Almerico et al., "On the Preparation of 1-Aryl-2-Heteroaryl- and 2-Aryl-1-Heteroaryl-Pyrroles as Useful Building Blocks for Biologically Interesting Hetrocycles", Abramobitch, (2001), p. 129-142.

Koch et al., "QSAR and Molecular Modeling for a Series of Isomeric X-Sulfanilamido-1-Phenylpyrazoles", Quantitive Structure Activity Relationships, (1993), vol. 12, pp. 373-382.

Mutlib et al., "Disposition of 1-[3-(Aminomethyl)phenyl]-N-[3-fluoro-2'-(methylsulfonyl)-p1, 1'-biphenyl]-4-yl-3-(trifluoromethyl)-1H-pyrazole-5-carboxamide (DPC 423) by Novel Metabolic Pathways. Characterization of Unusual Metabolites by Liquid chromatography/Mass Spectrometry and NMR" Chemical Research in Toxicology, (2002), vol. 15, pp. 48-62.

Mutlib et al., "P450-Mediated metabolism of 1-[3-(Aminomethyl)phenyl1]-N-[3-fluoro-2'-(methylsulfonyl)-[1,1'-biphenyl]-4-yl]-3-(trifluoromethyl)-1H-pyrazole-5-carboxamide (DPC 423) and Its Analogues to Aldoximes. Characterization of Glutathione Conjugates of Postulated Intermediates Derived from Aldoximes",Chemical Research Toxicology, (2002), vol. 15, pp. 63-75.

Boer et al., "Synthesis and Characterization of Conjugated Mono- and Dithiol Oligomers and Characterization of Their Self-Assembled Monolayers", Langmuir, (2003), vol. 19, pp. 4272-4284.

Johnson et al., "An evaluation of the effect of light stabilizers on the exterior durability of polyester powder coatings for the architectural market", Surface Coatings International, (1999), vol. 3, pp. 134-141.

Krasovitskii et al., "Synthesis and Spectral-Luminescence Properties of Hetarylethylene Derivatives of 2, 5-Diphenyloxazole and 2, 5-Diphenyl-1,3,4-Oxidiazole", Plenum Publishing Corporation, (1982), pp. 461-465.

Leung et al., "The Difluoromethylenesulfonic Acid Group as a Monoanionic Phosphate Surrogate for Obtaining PTP1B Inhibitors", Bioorganic & Medicinal Chemistry, (2002), vol. 10, pp. 2309-2323.

Shi et al., "Abnormal Diels-Alder Reaction of 5-Alkoxythiazoles with Highly Reactive Dienophiles; 4-Phenyl-3H-1,2,4-triazole-3,5(4H)-dione, Diethyl Azodicarboxylate, and Diethyl Oxomalonate", Bulletin Chem. Soc. Japan, (Dec. 1992), vol. 65, pp. 3315-3321.

Seimiya et al., "Telomere Shortening and Growth Inhibition of Human Cancer Cells by Novel Synthetic Telomerase Inhibitors MST-312, MST-295, and MST-199", Molecular Cancer Terapeutics, (Jul. 2002), vol. 1, pp. 657-665.

Byron et al., "The Shythesis of some Substituted Biphenyl-4-carboylic Acids, 4-Biphenylylacetic Acids, and 4-Aminobiphenyls", Journal of the Chemical Society, (1960), vol. 40, pp. 840-845.

Albericio et al., "Synthesis of a Sulfahydantion Library", American Chemical Society, (2001), vol. 3, pp. 290-300.

Katrizky et al., "Novel Chromophoric Heterocycles Based on Maleimide and Naphthoquinone", (Jul.-Aug. 1989), vol. 26, pp. 885-892.

Closier et al., "Nitrofuryl Heterocyclics", Journal of Medicinal Chemistry, (1970), vol. 13, pp. 638-640.

Kurogi et al., "Discovery of Novel Mesangial Cell Proliferation Inhibitors Using a Three-Dimensional Database Searching Method", Journal of Med. Chem. (2001), vol. 44, pp. 2304-2307.

Islip et al., "Nitrofuryl Heterocyclics", Journal of Medicinal Chemistry, (1973), vol. 16, pp. 1308-1310.

Rooney et al., "Inhibitors of Glycolic Acid Oxidase. 4-Substituted 3-Hydroxy-1H-pyrrole-2,5-dione Derivatives", Journal of Medicinal Chemistry, (1983), vol. 26, pp. 700-714.

Yoshino et al., "Organic Phosphorus Compounds. 2. Synthesis and Coronary Vasodilator Activity of (Benzothiazolylbenzyl) phosphonate Derivatives", Journal of Medicinal Chemistry, (1989), vol. 32, pp. 1528-1532.

Picard et al., "Inhibitors of Acyl-CoA: Cholesterol O-Acyltransferase. 17. Structure-Activity Relationships of Several Series of Compounds Derived from N-Chlorosulfonyl Isocyanate", Journal of Medicinal Chemistry, (1996), vol. 39, pp. 1243-1252.

Rebek Jr. et al., "Convergent Functional Groups: Synthetic and Structural Studies", J. Am. Chem. Soc., (1985), vol. 107, pp. 7476-7481.

Wilson et al., "Laser-Jet Delayed Trapping: Electron-Transfer Trapping of the Photoenol from 2-Methylbenzophenone", J. Am. Chem. Soc., (1987), vol. 109, pp. 4743-4745.

Garcia-Tellado et al., "Molecular Recognition in the Solid State: Controlled Assembly of Hydrogen-Bonded Molecular Sheets", J. Am. Chem. Soc. (1991), vol. 113, pp. 9265-9269.

Seminario et a., "Theoretical Study of a Molecular Resonant Tunneling Diode", J. Am. Chem. Soc., (2000), vol. 122, pp. 3015-3020.

Yoneda et al., "A New Synthesis of Purines", J.C.S. Chem. Comm., (1974), vol. 45, p. 551.

Anzai, Kentaro, "Alkyl- and Arylthiation of Uracil and Indole", Journal of Heterocyclic Chemistry, (Apr. 1979), pp. 567-569.

Link et al., "Synthesis of 8-Substituted 5-Deazaflavins", Journal of Heterocyclic Chemistry, (May-Jun. 1985), vol. 22, pp. 841-848.

Baker et al., "Irreversibly Enzyme Inhibitores. 188. Inhibitoin of Mammalian Thymidine Phosphorylase", Journal of Medicinal Chemistry, (1971), vol. 14, pp. 812-816.

Yoshimoto et al., "Correlation Analysis of Baker's Studies on Enzyme Inhibition. 2. Chymotrypsin, Trypsin, Thymidine Phosphorylase, Uridine Phosphorylase, Thymidylate Synthetase, Cytosine Nucleoside Deaminase, Dihydrofolate Reductase, Malate Dhydrogenase, Glutamate Dehydrogenase, Lactate Dehydrogenase, and Glyceraldehyde-phosphate Dehydrogenase", Journal of Medicinal Chemistry, (1976), vol. 19, pp. 71-98.

Bourdonnec et al., "Synthesis and Pharmacological Evaluation of New Pyrazolidine-3,5-diones as AT₁ Angiotensin II Receptor Antagonists", Journal of Medicinal Chemistry, (2000) vol. 43, pp. 2685-2697.

Rebek, Jr. et al., "Convergent Functional Groups. 2. Structure and Selectivity in Olefin Epoxidation with Peracids", J. Org. Chem., (1986), vol. 51, pp. 1649-1653.

Medebielle et al., "A convenient Synthesis of Perfluoroalkylated and Fluorinated-Aryl Nitrogen Bases by Electrochemically Induced Sm1 Substitution", J. Org. Chem., (1996), vol. 61, pp. 1331-1340.

Shinkai et al., "Coenzyme Models. Part 45. Synthesis of Atropisomeric Flavins and their Novel Redox-induced Racemisation", J. Chem. Soc., (1988), pp. 313-319.

Huang et al., "Inhibition of Nucleoside Transport by Protein Kinase Inhibitors", The Journal of Pharmacology and Experimental Therapeutics, (2003), vol. 304, pp. 753-760.

Byron et al., "The Synthesis of some Substituted Biphenyl-4-carboxylic Acids, 4-Biphenylylacetic Acids, and 4-Aminobiphenyls", J. Chem. Soc. (1963), pp. 840-845.

Mikhaleva et al., "Rlative Reactivities of the Chlorine Atoms of 2,2',4-Trichloro-4', 5-Dipyrimidinyl in its Reaction with Piperidine", Plenum Publishing Corporation, (1979), pp. 671-676.

Kim et al., "Solid phase synthesis of benzamindine and butylamine-derived hydantoin libraries", Molecular Diversity, (1998), vol. 3, pp. 129-132.

Yonezawa et al., "Synthesis of sequentially controlled isometric, wholly aromatic polyketones composed of 2-trifluoromethylbiphenylene and 2,2'-dimethoxybiphenylene units", Reactive & Functional Polymers, (2002) vol. 52, pp. 19-30.

Nikolaev et al., "Solubility polytherm in the system HNO3-H2O-(C4H9O)PO(C4H9)2", Institute of Inorganic Chemistry, (Feb. 1965), vol. 160, pp. 841-844.

Nantka-Namirski et al., "Condensation Reaction of Ethyl (4-URACIL)-Acetate with Ethyl Orthoformate", Acta Polon. Pharm., (1971), vol. 28, pp. 456-463.

Bais et al., "Inhibition of endogenous oxalate production: biochemical considerations of the roles of glycollate oxidase and lactate dehydrogenase", Chemical Science, (1989), vol. 76, pp. 303-309.

Satsangi et al., "1-(4-Substituted-thiazol-2-yl)hydantoins as Antiinflammatory and CNS-Active Agents", Pharmazie, (1983), vol. 38, pp. 341-342.

Furuya et al., "Addition of 4-Ethoxyimidazoles to Dimethyl Acetylenedicarboxylate and Transformationof the Adducts to Pyrimidin-5-yl Acetates", Chem. Pharm. Bull., (1988), vol. 36, pp. 1669-1675.

Zaidi et al., "New Anti-mycobacterial Hydantoins", Pharmazie, (1980), vol. 35, pp. 755-756.

Ishida et al., "Molecular arrangement and electrical conduction of self-assembled monolayers made from terphenyl thiols", Surface Science, (2002), vol. 514, pp. 187-193.

Kundu et al., "Depropargylation under palladium-copper catalysis: synthesis of diaryl sulfides", Tetrahedron, vol. 57, pp. 5885-5895.

Medebielle et al., "A New Convenient Synthesis of 5-Aryl Uracils SRN1 ARomatic Nucleophilic Substitution", Tetrahedron Letters, (1993), vol. 34, pp. 3409-3412.

Flatt et al., "Synthesis of thiol substituted oligoanilines for molecular device candidates", Tetrahedron Letters, (2003), vol. 44, pp. 6699-6702.

Saiga et al., "Consecutive cross-coupling of o-phenylenedizinc compound with acyl and/or aryl halides in the presence of Pd(0)-tris(2,4,6-trimethoxyphenyl)phosphine", Tetrahedron Letters, (2000), vol. 41, pp. 4629-4632.

Mamaev et al., "Synthesis of 2,5'-Bipyrimidines from Substituted 5-Cyanopyrimidines", Plenum Publishing Corporation, (1988), pp. 303-307.

Nofal et al., "Synthesis of Novel Uracil-5-Sulphonamide Derivatives of Possible Biological Activity", Egypt J. Chem., (1990), vol. 33, pp. 375-380.

Igarashi et al., "Antimicrobial activities of 2-arylthio-N-alkylmaleimides", Journal of Industrial Microbiology, (1992), vol. 9, pp. 91-96.

Fathalla et al., "Synthesis of New Uracil-5-Sulfonamide Derivatives and Immuno-Stimulatory Effect of a Chemically Modified Hemolymph of *Biomphalaria alexandrina* on *Schistosoma mansoni* Infected Mice", Arch Pahrm Res, (2003), vol. 26, pp. 358-366.

O.A. Fathalla, "Synthesis of New Pyrazolo[1,5-a]pyrimidine Derivative Using 5-Aminouracil and Ketene Dithioacetal", Arch Pharm Res, (1999), vol. 22, pp. 571-574.

Fathalla et al., "Synthesis of Some New Uracil—5—Sulphonamide-p-Phenyl Derivatives and Their Effect on *Biomphalaria alexandina* snails", Bull. N R C, Egypt, (2000), vol. 25, pp. 341-363.

Y. Guzel, "Investifation of the relationship between the inhibitory activity of glycolic acid oxidase (GAO) and its chemical structure: electron-topological approach.", Journal of Molecular Structure, (1996), vol. 366, pp. 131-137.

Brasher et al., "c-Abl Has High Intrinsic Tyrosine Kinase Activity That Is Stimulated by Mutation of the Src Homology 3 Domain and by Autophosphorylation at Two Distinct Regulatory Tyrosines", The Journal of Biological Chemistry, (Nov. 10, 2000), vol. 275, pp. 35631-35637.

Barker et al., "Characterization of pp60 Tyrosine Kinase Activities Using a Continuous Assay: Autoactivation of the Enzyme Is an Intermolecular Autophosphorylation Process", Biochemistry, (1995), vol. 34, pp. 14843-14851.

Okano et al., "o-Bromophenylzinc Compound: A Readily Available and Efficient Synthetic Equivalent of o-Phenylene 1-Anion 2-Cation", Tetrahedron Letters, (1998), vol. 39, pp. 3001-3004.

* cited by examiner

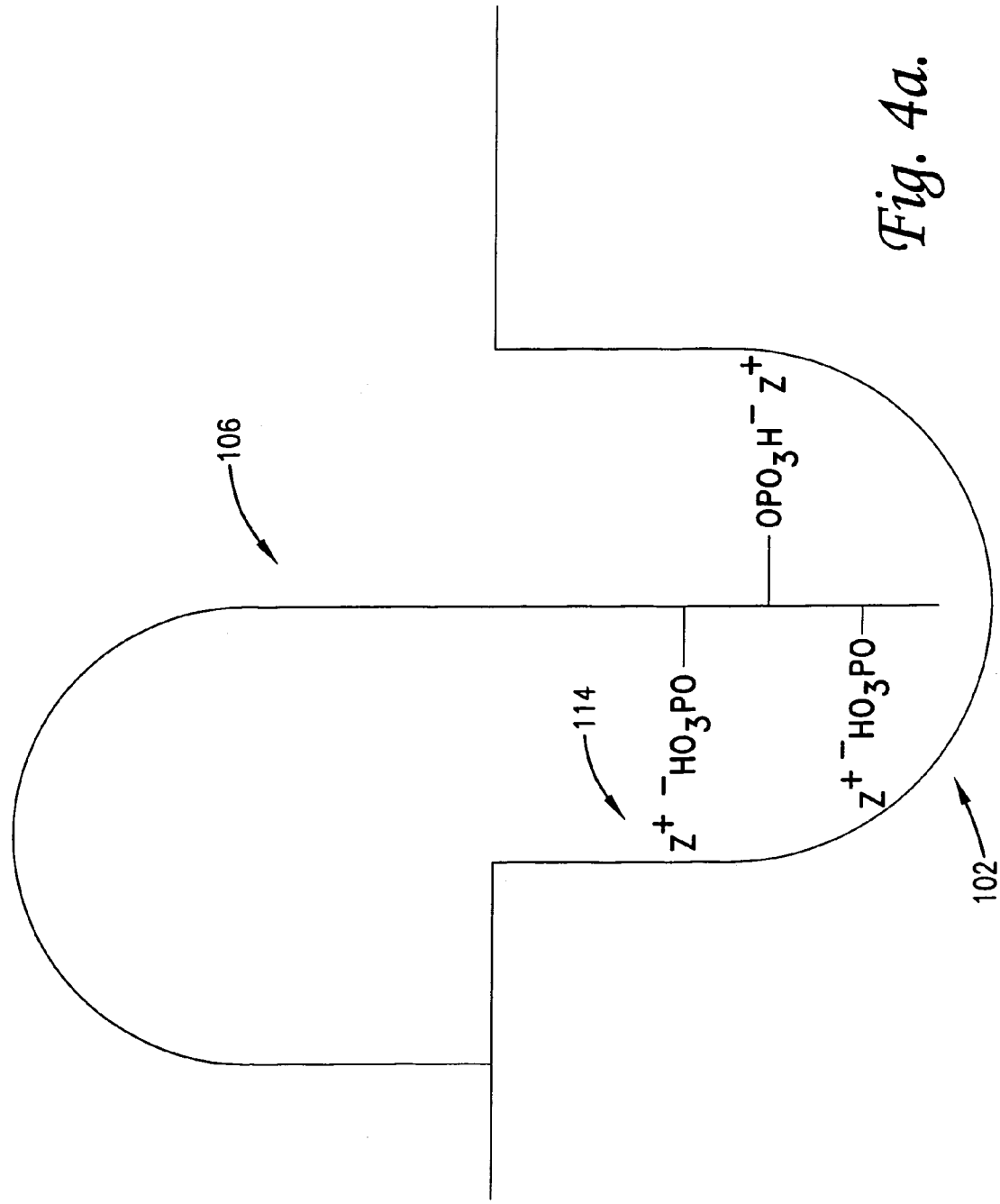

ANTI-CANCER MEDICAMENTS

RELATED APPLICATIONS

This application claims the benefit of provisional applications entitled Process For MODULATING PROTEIN FUNCTION, Ser. No. 60/437,487 filed Dec. 31, 2002, ANTI-CANCER MEDICAMENTS, Ser. No. 60/437,403 filed Dec. 31, 2002, ANTI-INFLAMMATORY MEDICAMENTS, Ser. No. 60/437,415 filed Dec. 31, 2002, ANTI-INFLAMMATORY MEDICAMENTS, Ser. No. 60/437,304 filed Dec. 31, 2002, and MEDICAMENTS FOR THE TREATMENT OF NEURODEGENERATIVE DISORDERS OR DIABETES, Ser. No. 60/463,804 filed Apr. 18, 2003. Each of these applications is incorporated by reference herein.

BACKGROUND OF THE INVENTION

1. Field of the Invention

The present invention relates to novel compounds and methods of using those compounds to treat oncological conditions.

2. Description of the Prior Art

Basic research has recently provided the life sciences community with an unprecedented volume of information on the human genetic code and the proteins that are produced by it. In 2001, the complete sequence of the human genome was reported (Lander, E. S. et al. Initial sequencing and analysis of the human genome. *Nature* (2001) 409:860; Venter, J. C. et al. The sequence of the human genome. *Science* (2001) 291:1304). Increasingly, the global research community is now classifying the 50,000+ proteins that are encoded by this genetic sequence, and more importantly, it is attempting to identify those proteins that are causative of major, under-treated human diseases.

Despite the wealth of information that the human genome and its proteins are providing, particularly in the area of conformational control of protein function, the methodology and strategy by which the pharmaceutical industry sets about to develop small molecule therapeutics has not significantly advanced beyond using native protein active sites for binding to small molecule therapeutic agents. These native active sites are normally used by proteins to perform essential cellular functions by binding to and processing natural substrates or tranducing signals from natural ligands. Because these native pockets are used broadly by many other proteins within protein families, drugs which interact with them are often plagued by lack of selectivity and, as a consequence, insufficient therapeutic windows to achieve maximum efficacy. Side effects and toxicities are revealed in such small molecules, either during preclinical discovery, clinical trials, or later in the marketplace. Side effects and toxicities continue to be a major reason for the high attrition rate seen within the drug development process. For the kinase protein family of proteins, interactions at these native active sites have been recently reviewed: see J. Dumas, Protein Kinase Inhibitors: Emerging Pharmacophores 1997-2001, *Expert Opinion on Therapeutic Patents* (2001) 11: 405-429; J. Dumas, Editor, New challenges in Protein Kinase Inhibition, in *Current Topics in Medicinal Chemistry* (2002) 2: issue 9.

It is known that proteins are flexible, and this flexibility has been reported and utilized with the discovery of the small molecules which bind to alternative, flexible active sites with proteins. For review of this topic, see Teague, *Nature Reviews/Drug Discovery*, Vol. 2, pp. 527-541 (2003).

See also, Wu et al., *Structure*, Vol. 11, pp. 399-410 (2003). However these reports focus on small molecules which bind only to proteins at the protein natural active sites. Peng et al., *Bio. Organic and Medicinal Chemistry Ltrs.*, Vol. 13, pp. 3693-3699 (2003), and Schindler, et al., *Science*, Vol. 289, p. 1938 (2000) describe inhibitors of abl kinase. These inhibitors are identified in WO Publication No. 2002/034727. This class of inhibitors binds to the ATP active site while also binding in a mode that induces movement of the kinase catalytic loop. Pargellis et al., *Nature Structural Biology*, Vol. 9, p. 268 (2002) reported inhibitors p38 alpha-kinase also disclosed in WO Publication No. 00/43384 and Regan et al., *J. Medicinal Chemistry*, Vol. 45, pp. 2994-3008 (2002). This class of inhibitors also interacts with the kinase at the ATP active site involving a concomitant movement of the kinase activation loop.

More recently, it has been disclosed that kinases utilize activation loops and kinase domain regulatory pockets to control their state of catalytic activity. This has been recently reviewed (see, e.g., M. Huse and J. Kuriyan, *Cell* (2002) 109:275).

SUMMARY OF THE INVENTION

The present invention is broadly concerned with new compounds for use in treating anti-inflammatory conditions and methods of treating such conditions. In more detail, the inventive compounds have the formula

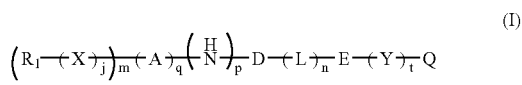

(I)

wherein:
R$^1$ is selected from the group consisting of aryls (preferably C$_6$-C$_{18}$, and more preferably C$_6$-C$_{12}$) and heteroaryls;

each X and Y is individually selected from the group consisting of —O—, —S—, —NR$_6$—, —NR$_6$SO$_2$—, —NR$_6$CO—, alkynyls (preferably C$_1$-C$_{12}$, and more preferably C$_1$-C$_6$), alkenyls (preferably C$_1$-C$_{12}$, and more preferably C$_1$-C$_6$), alkylenes (preferably C$_1$-C$_{12}$, and more preferably C$_1$-C$_6$), —O(CH$_2$)$_h$—, and —NR$_6$(CH$_2$)$_h$—, where each h is individually selected from the group consisting of 1, 2, 3, or 4, and where for each of alkylenes (preferably C$_1$-C$_{12}$, and more preferably C$_1$-C$_6$), —O(CH$_2$)$_h$—, and —NR$_6$(CH$_2$)$_h$—, one of the methylene groups present therein may be optionally double-bonded to a side-chain oxo group except that with —O(CH$_2$)$_h$—, the introduction of the side-chain oxo group does-not form an ester moiety;

A is selected from the group consisting of aromatic (preferably C$_6$-C$_{18}$, and more preferably C$_6$-C$_{12}$), monocycloheterocyclic, and bicycloheterocyclic rings;

D is phenyl or a five- or six-membered heterocyclic ring selected from the group consisting of pyrazolyl, pyrrolyl, imidazolyl, oxazolyl, thiazolyl, furyl, pyridyl, and pyrimidyl;

E is selected from the group consisting of phenyl, pyridinyl, and pyrimidinyl;

L is selected from the group consisting of —C(O)—, —S(O)$_2$—, —N(R$_6$)CO—, —N(R$_6$)SO$_2$—, —N(R$_6$)CON(R$_6$)—;

j is 0 or 1;

m is 0 or 1;

n is 0 or 1;
p is 0 or 1;
q is 0 or 1;
t is 0 or 1;
Q is selected from the group consisting of
Q-1
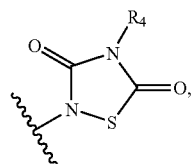
Q-2
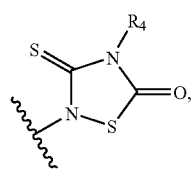
Q-3
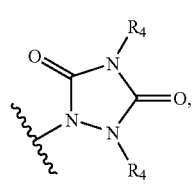
Q-4
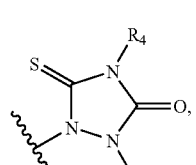
Q-5
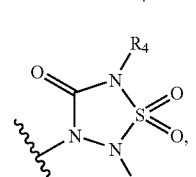
Q-6
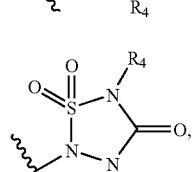
Q-7
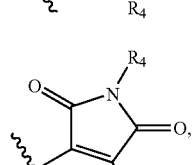
Q-8
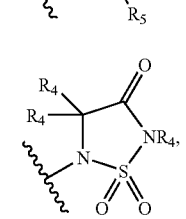
-continued
Q-9
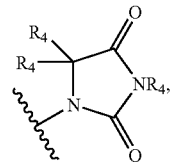
Q-10
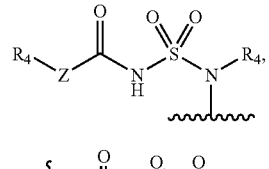
Q-11
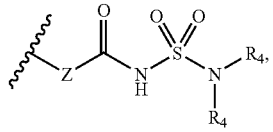
Q-12
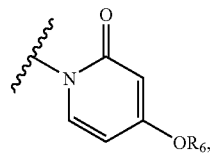
Q-13
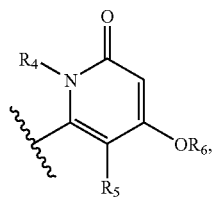
Q-14
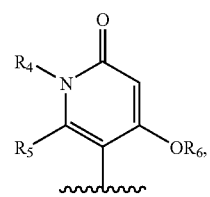
Q-15
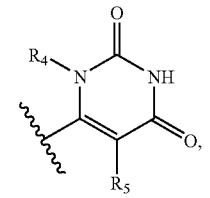
Q-16
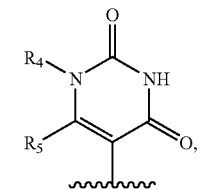
Q-17

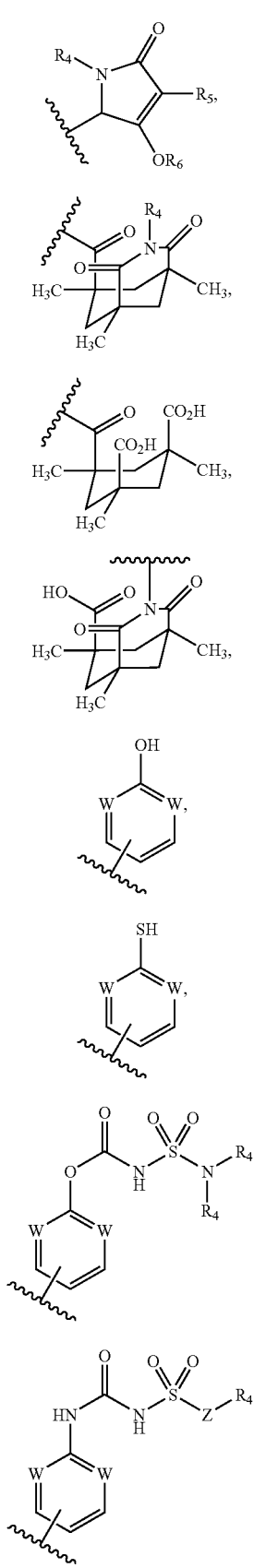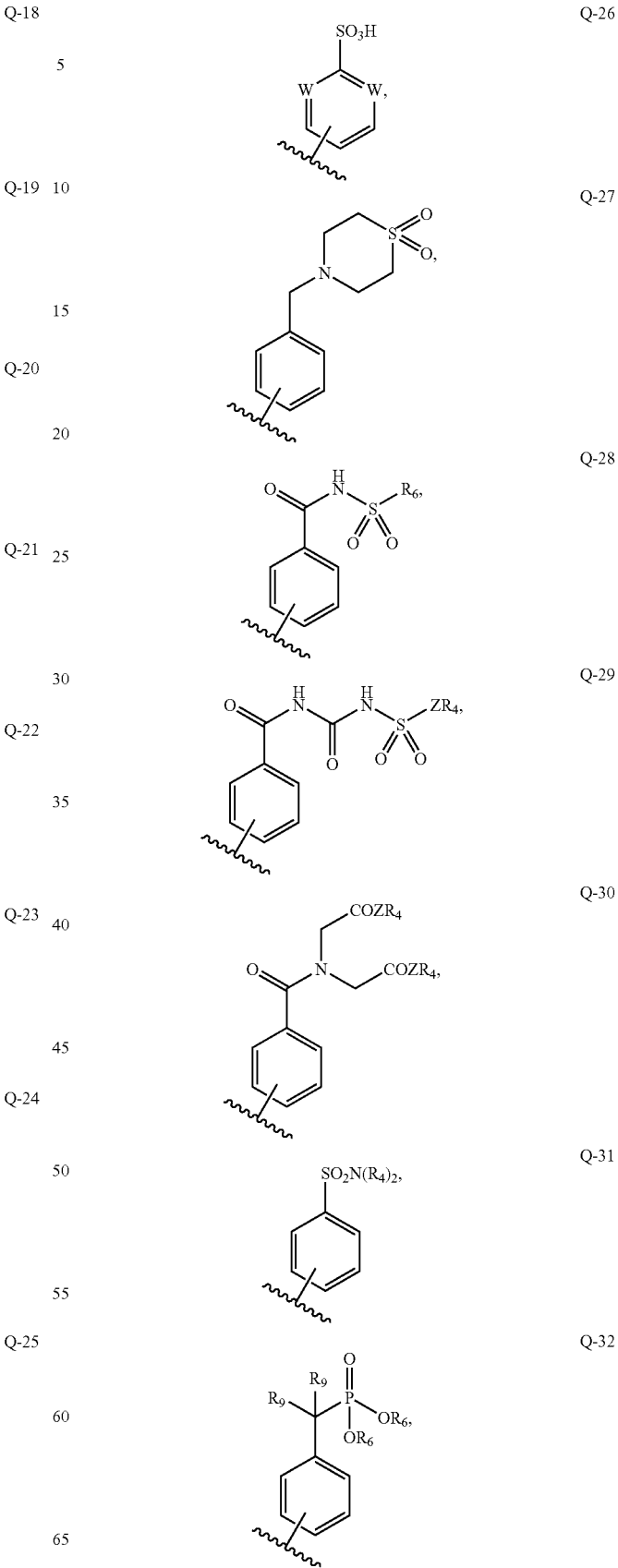

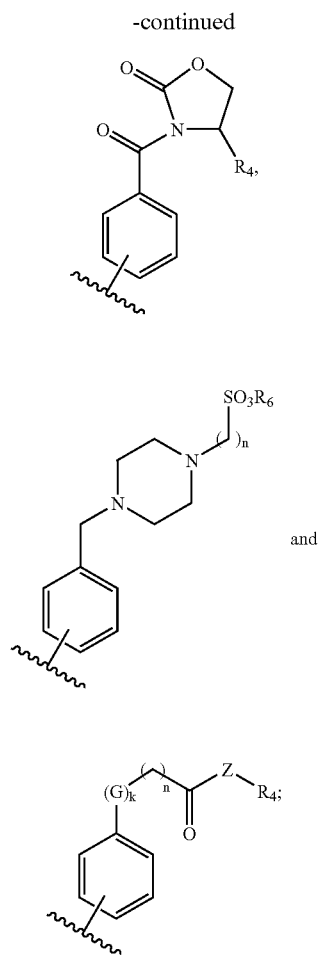

each R₄ group is individually selected from the group consisting of —H, alkyls (preferably $C_1$-$C_{12}$, and more preferably $C_1$-$C_6$), aminoalkyls (preferably $C_1$-$C_{12}$, and more preferably $C_1$-$C_6$), alkoxyalkyls (preferably $C_1$-$C_{12}$, and more preferably $C_1$-$C_6$), aryls (preferably $C_6$-$C_{18}$, and more preferably $C_6$-$C_{12}$), aralkyls (preferably $C_1$-$C_{12}$, and more preferably $C_1$-$C_6$), heterocyclyls, and heterocyclylalkyls except when the R₄ substituent places a heteroatom on an alpha-carbon directly attached to a ring nitrogen on Q;

when two R₄ groups are bonded with the same atom, the two R₄ groups optionally form an alicyclic or heterocyclic 4-7 membered ring;

each R₅ is individually selected from the group consisting of —H, alkyls (preferably $C_1$-$C_{12}$, and more preferably $C_1$-$C_6$), aryls (preferably $C_6$-$C_{18}$, and more preferably $C_6$-$C_{12}$), heterocyclyls, alkylaminos (preferably $C_1$-$C_{12}$, and more preferably $C_1$-$C_6$), arylaminos (preferably $C_6$-$C_{18}$, and more preferably $C_6$-$C_{12}$), cycloalkylaminos (preferably $C_3$-$C_{18}$, and more preferably $C_5$-$C_{12}$ and preferably $C_1$-$C_{12}$, and more preferably $C_1$-$C_6$), heterocyclylaminos, hydroxys, alkoxys (preferably $C_1$-$C_{12}$, and more preferably $C_1$-$C_6$), aryloxys (preferably $C_6$-$C_{18}$, and more preferably $C_6$-$C_{12}$), alkylthios (preferably $C_1$-$C_{12}$, and more preferably $C_1$-$C_6$), arylthios (preferably $C_6$-$C_{18}$, and more preferably $C_6$-$C_{12}$), cyanos, halogens, perfluoroalkyls (preferably $C_1$-$C_{12}$, and more preferably $C_1$-$C_6$), alkylcarbonyls (preferably $C_1$-$C_{12}$, and more preferably $C_1$-$C_6$), and nitros;

each R₆ is individually selected from the group consisting of —H, alkyls (preferably $C_1$-$C_{12}$, and more preferably $C_1$-$C_6$), allyls, and β-trimethylsilylethyl;

each R₈ is individually selected from the group consisting of alkyls (preferably $C_1$-$C_{12}$, and more preferably $C_1C_6$), aralkyls (preferably $C_1$-$C_{12}$, and more preferably $C_1$-$C_6$), heterocyclyls, and heterocyclylalkyls;

each R₉ group is individually selected from the group consisting of —H, —F, and alkyls (preferably $C_1$-$C_{12}$, and more preferably $C_1$-$C_6$), wherein when two R₉ groups are geminal alkyl groups, said geminal alkyl groups may be cyclized to form a 3-6 membered ring;

G is selected from the group consisting of —O—, —S—, and —N(R₄)—;

k is 0 or 1;

each Z is individually selected from the group consisting of —O— and —N(R₄)—; and each ring of formula (I) optionally includes one or more of R₇, where R₇ is a noninterfering substituent individually selected from the group consisting of —H, alkyls (preferably $C_1$-$C_{12}$, and more preferably $C_1$-$C_6$), aryls (preferably $C_6$-$C_{18}$, and more preferably $C_6$-$C_{12}$), heterocyclyls, alkylaminos (preferably $C_1$-$C_{12}$, and more preferably $C_1$-$C_6$), arylaminos (preferably $C_6$-$C_{18}$, and more preferably $C_6$-$C_{12}$), cycloalkylaminos (preferably $C_3$-$C_{18}$, and more preferably $C_5$-$C_{12}$ and preferably $C_1$-$C_{12}$, and more preferably $C_1$-$C_6$), heterocyclylaminos, hydroxys, alkoxys (preferably $C_1$-$C_{12}$, and more preferably $C_1$-$C_6$), aryloxys (preferably $C_6$-$C_{18}$, and more preferably $C_6$-$C_{12}$), alkylthios (preferably $C_1$-$C_{12}$, and more preferably $C_1$-$C_6$), arthylthios, cyanos, halogens, nitrilos, nitros, alkylsulfinyls (preferably $C_1$-$C_{12}$, and more preferably $C_1$-$C_6$), alkylsulfonyls (preferably $C_1$-$C_{12}$, and more preferably $C_1$-$C_6$), aminosulfonyls, and perfluoroalkyls (preferably $C_1$-$C_{12}$, and more preferably $C_1$-$C_6$).

In a preferred embodiment, the structure is of formula (I) except that:

when Q is Q-3 or Q-4, then the compound of formula (I) is not

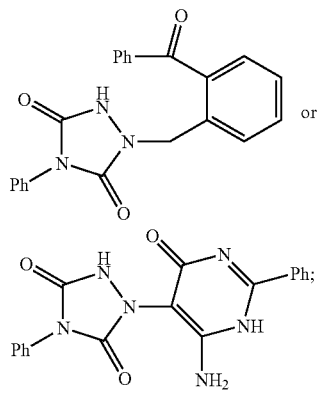

when Q is Q-7, then the compound of formula (I) is not

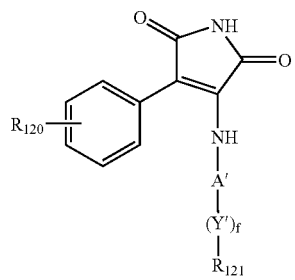

R120 = 2,3-difluoro; 2,3,6-trifluoro; 2, fluoro, 3-chloro; 2-chloro, 3-fluoro; 3-cyano; 4-chloro
A' = substituted phenyl
Y' = CO; —NHCO—; —SO2—; —SO2NH—;
f = 0 or 1
R121 = substituted phenyl; oxazolyl; pyridyl; pyrimidyl; pyrazolyl; imidazolyl

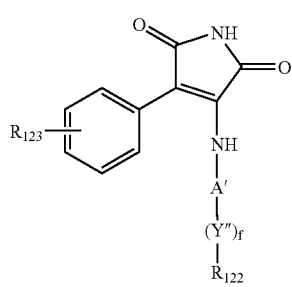

R123 = H; 2,3-difluoro; 3,5-difluoro; 2-fluoro; 4-fluoro; 2-chloro; 2,4-dichloro; 3,4-dichloro; 3-fluoro; 4-chloro, 2-bromo; 3-bromo; 4-bromo; 4-iodo; 2-methoxy; 3-methoxy; 4-methoxy; 3,4-dimethoxy; 2,4-dimethoxy; 2,5-dimethoxy; 3,4,5-trimethoxy; 3-CF3; 4-CF3; 3,5-di-CF3; 4-CF3O; 3-nitro; 3-nitro-4-chloro; 2-methyl; 3-methyl; 4-methyl; 3,5-dimethyl; 4-iso-propyl; 3-methylthio; 3-CF3S; 3-chloro-4-methoxy 4-methylthio; 4-hydroxy; 4-methoxymethyl; 4-methylsulfonyl
A' = substituted phenyl
Y" = CO; f = 0 or 1
R122 = substituted phenyl; oxazolyl; pyrimidyl when Q is Q-7, $R_5$ is —OH, Y is —O—, —S—, or —CO—, m is 0, n is 0, p is 0, q is 0, and E is phenyl, then D is not thienyl, thiazolyl, or phenyl;
when Q is Q-7, then the compound of formula (I) is not

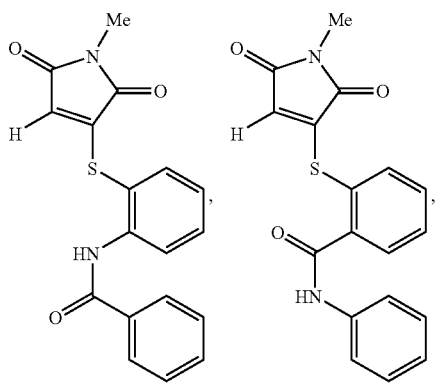

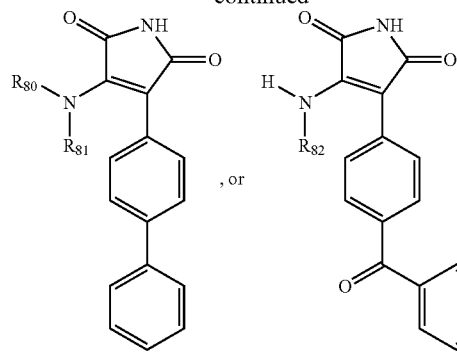

R80 is H, Me
R81 is substituted phenyl
R82 is substituted phenyl when Q is Q-9, then the compound of formula (I) is not

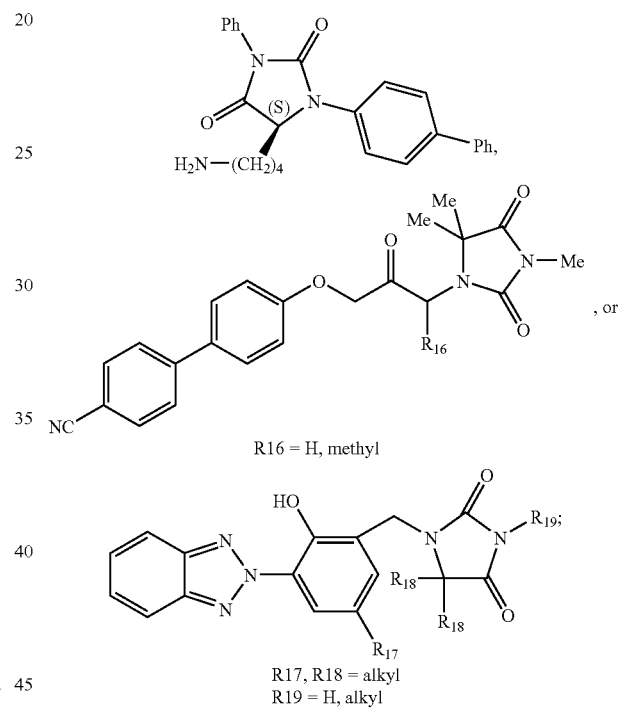

R16 = H, methyl

R17, R18 = alkyl
R19 = H, alkyl when Q is Q-10, then the compound of formula (I) is not

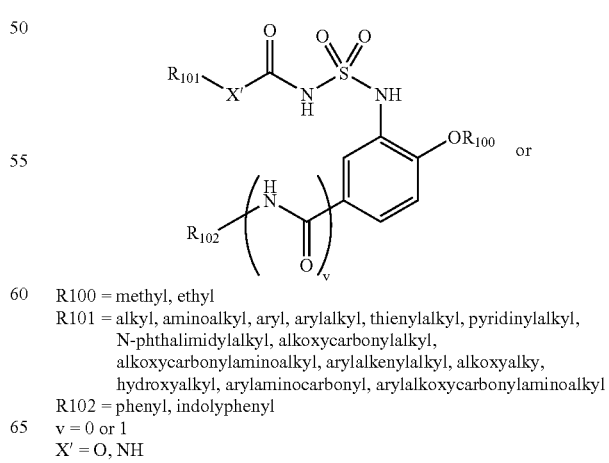

R100 = methyl, ethyl
R101 = alkyl, aminoalkyl, aryl, arylalkyl, thienylalkyl, pyridinylalkyl, N-phthalimidylalkyl, alkoxycarbonylalkyl, alkoxycarbonylaminoalkyl, arylalkenylalkyl, alkoxyalky, hydroxyalkyl, arylaminocarbonyl, arylalkoxycarbonylaminoalkyl
R102 = phenyl, indolyphenyl
v = 0 or 1
X' = O, NH -continued

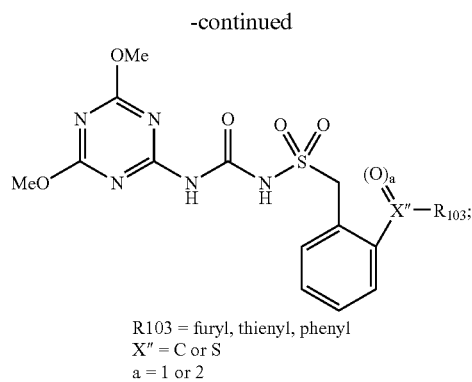

R103 = furyl, thienyl, phenyl
X" = C or S
a = 1 or 2 wherein there is a bond between Q and

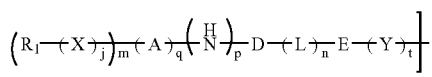

of formula (I), and when Q is Q-11, t is 0, and E is phenyl, then any $R_7$ on E is not an o-alkoxy in relation to said bond;

when Q is Q-11, then the compound of formula (I) is not

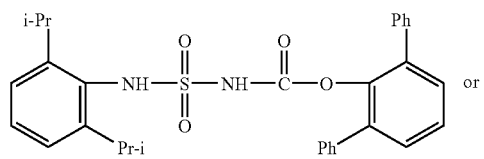

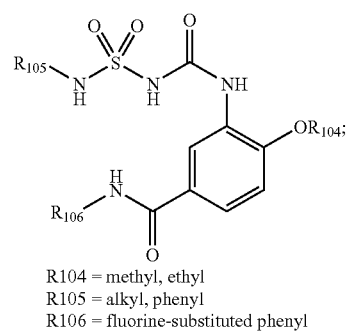

R104 = methyl, ethyl
R105 = alkyl, phenyl
R106 = fluorine-substituted phenyl when Q is Q-15, then the compound of formula (I) is not

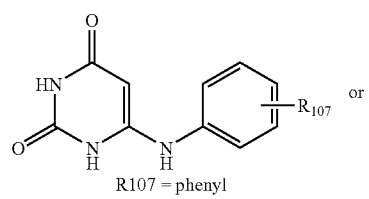

R107 = phenyl

-continued

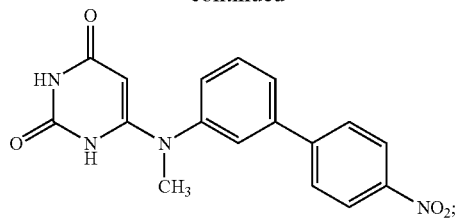

when Q is Q-16, then the compound of formula (I) is not

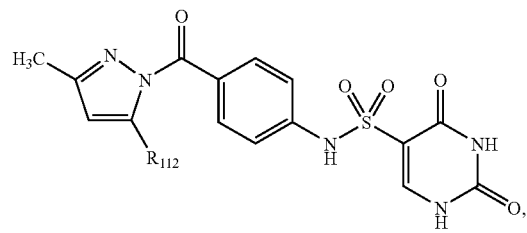

$R_{112}$ = Me, OH

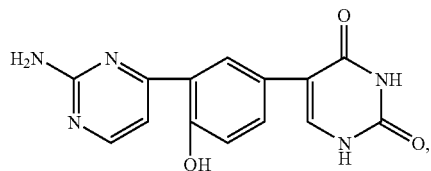

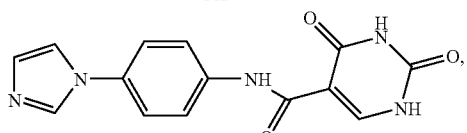

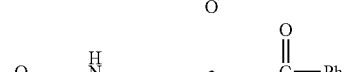

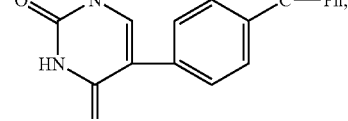

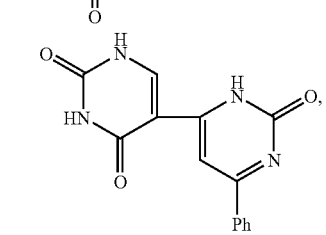

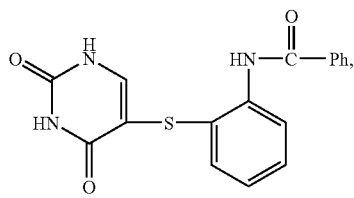

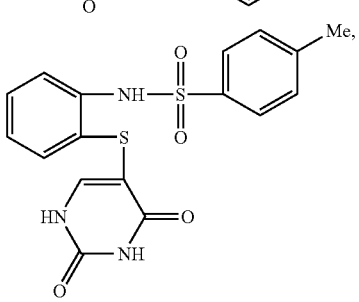

$R_{108}$ = OH, SH, NH2
$R_{109}$ = hydrogen or one or more methoxy, hydroxy, halogen, nitro, dimethylamino, or furanyl
$R_{110}$ = substituted phenyl, furanyl
$R_{111}$ = OH or Cl
$X_3$ = O, NH when Q is Q-17, then the compound of formula (I) is not $R_{29}$ = alkyl
$R_{30}$ = H, t-Bu, benzoyl when Q is Q-21, then the compound of formula (I) is not when Q is Q-22, then the compound of formula (I) is selected from the group consisting of

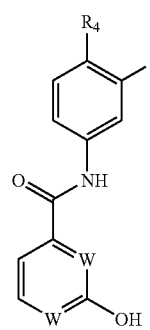
L₁-C(O) or S(O₂)
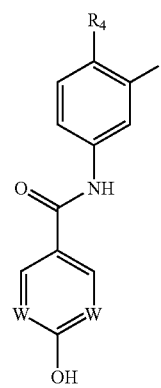
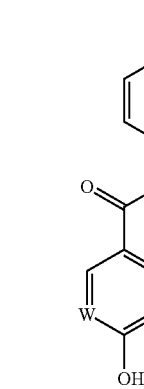
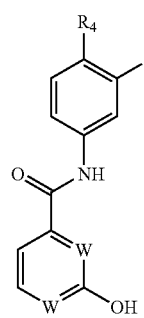
, and
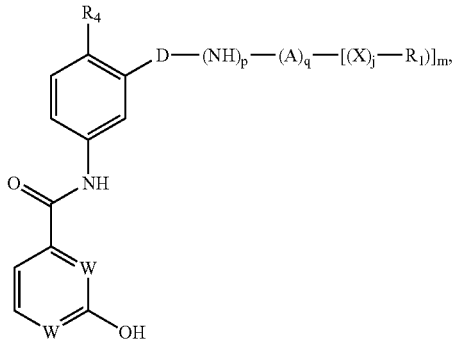
but excluding
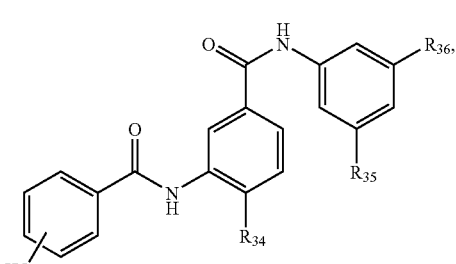
meta or para-
R34 = Me, Cl
R35 = —N(Me)2, morpholino
R36 = H, F
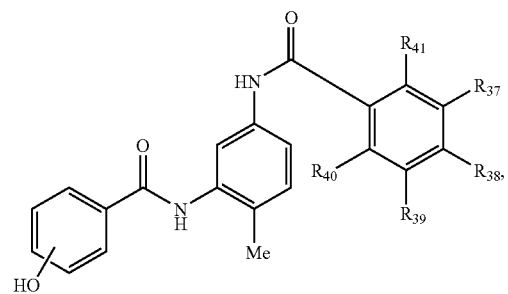
meta or para-
R37 = N(Me)2, morpholino, OMe, OH, H
R38 = H, CN, OMe, OH, benzyloxy, phenyl, nitro
R39 = H, OH
R40 = H, F
R41 = H, Cl
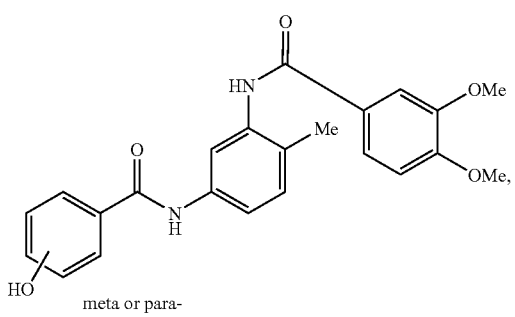
meta or para- -continued
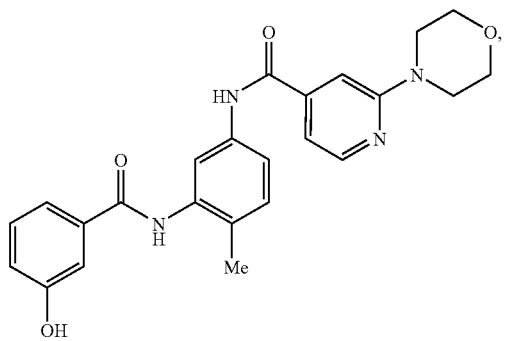
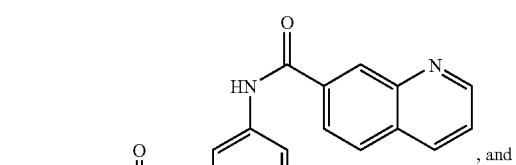
meta or para-
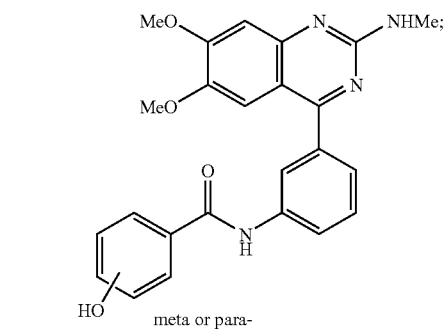
meta or para-
when Q is Q-23, then the compound of formula (I) is not
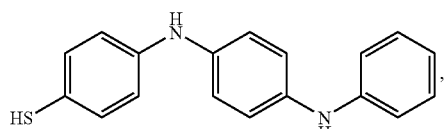
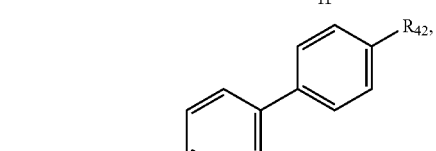
R₄₂ = H, Me
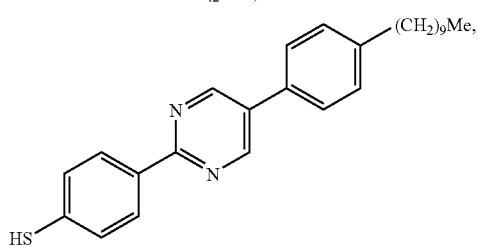
-continued
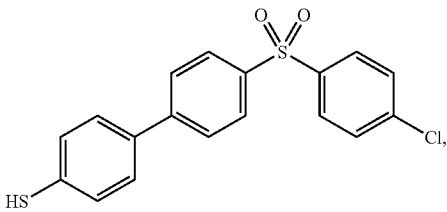
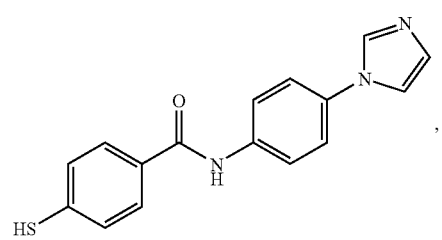
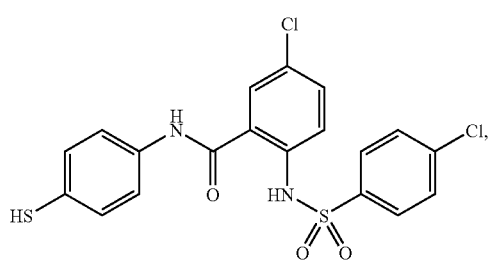
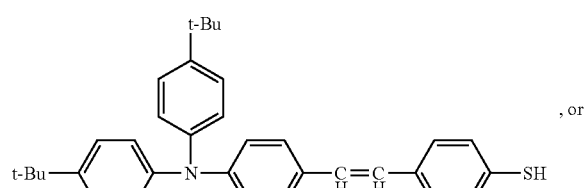
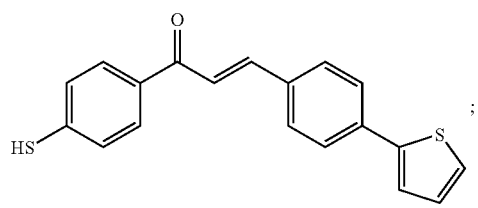
when Q is Q-24, Q-25, Q-26, or Q-31, then
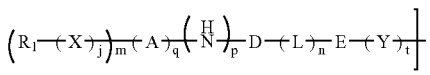
is selected from the group consisting of
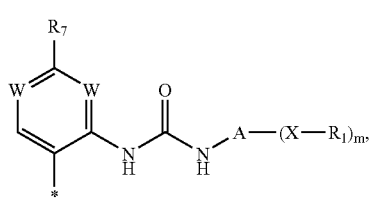

-continued

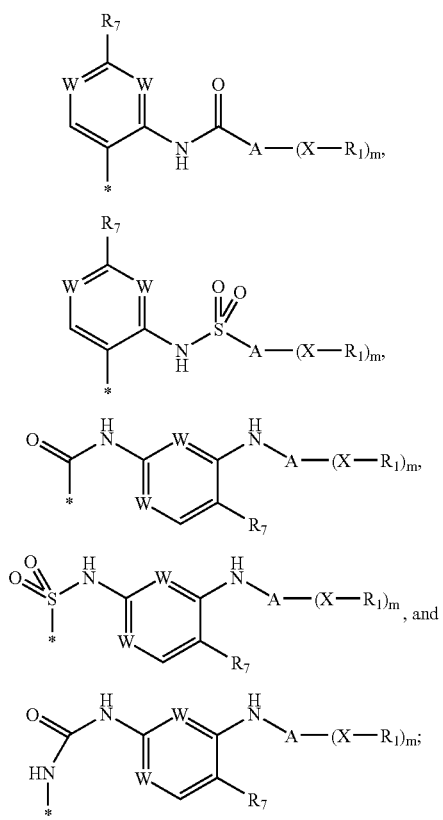

wherein each W is individually selected from the group consisting of —CH— and —N—; and -continued

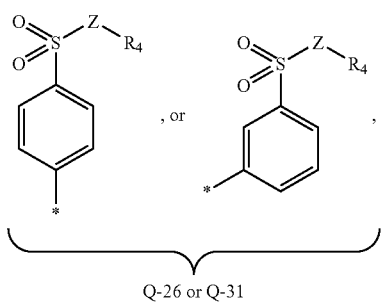

Q-26 or Q-31 where * denotes the point of attachment to Q-24, Q-25, Q-26, or Q-31;

when Q is Q-31, then the compound of formula (I) is not

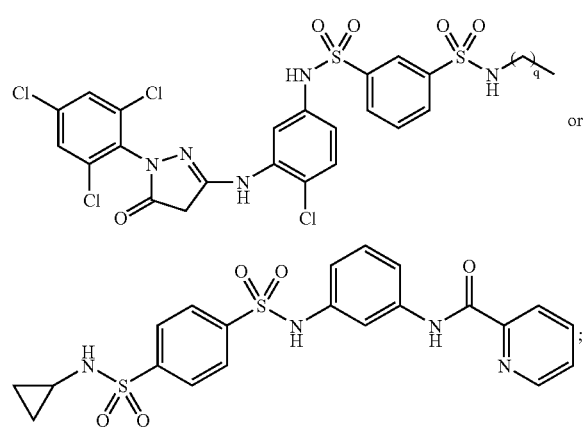

when Q is Q-28, then the compound of formula (I) is not

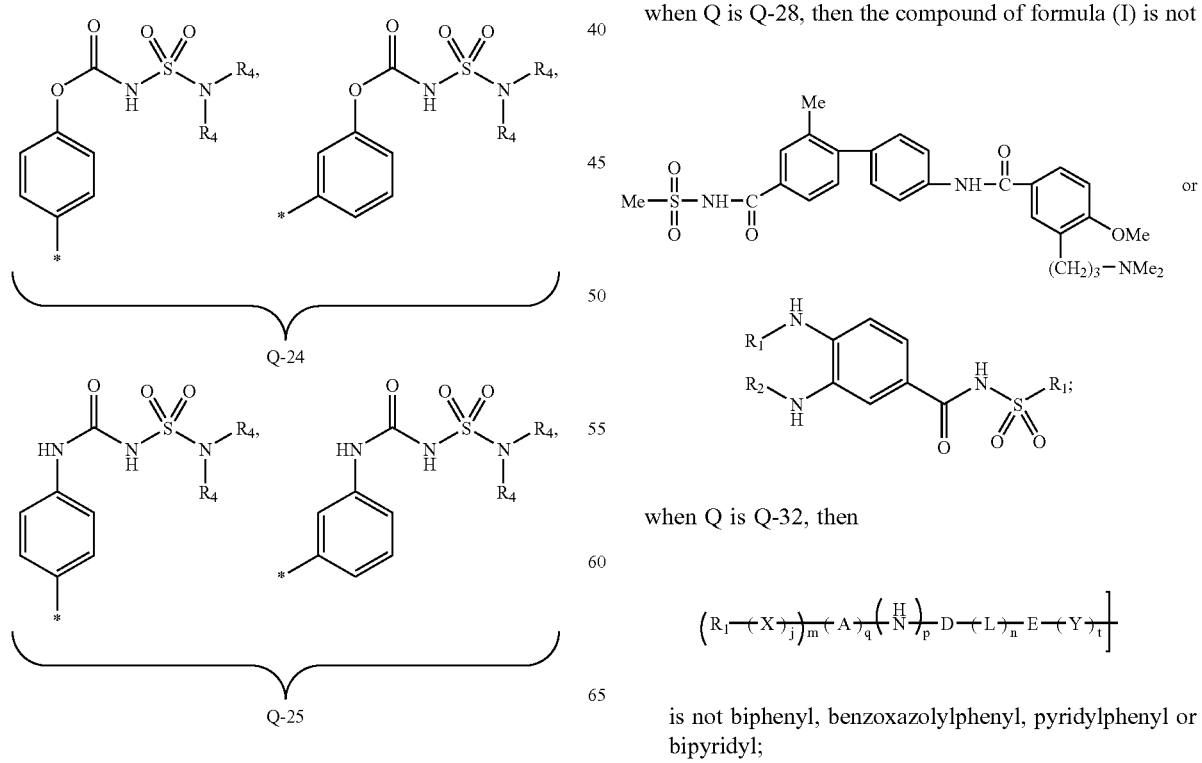

when Q is Q-32, then $$\left(R_1{+}(X{)_j}{)_m}{+}A{)_q}{+}N{)_p}{\overset{H}{}}D{+}L{)_n}E{+}Y{)_t}\right]$$

is not biphenyl, benzoxazolylphenyl, pyridylphenyl or bipyridyl;

when Q is Q-32, then the compound of formula (I) is not

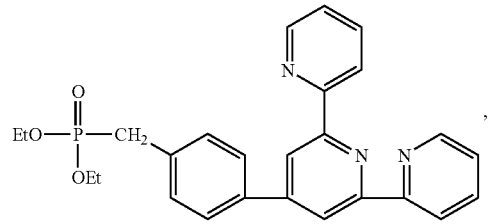

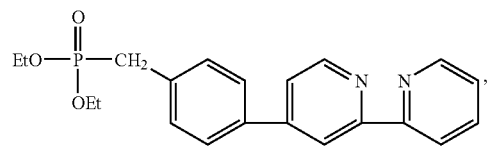

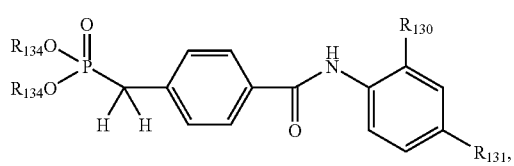

R_{130} = benzoyl, substituted phenylaminocarbonyl
R_{131} = Cl, Br, SPh, benzoyl, phenylsulfonyl
R_{132} = substituted phenylaminocarbonyl
R_{133} = H, Cl
R_{134} = H, alkyl, allyl, B-trimethylsilylethyl

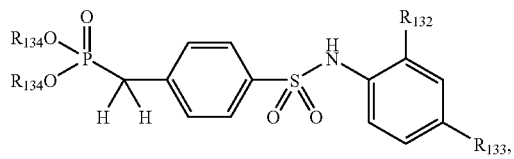

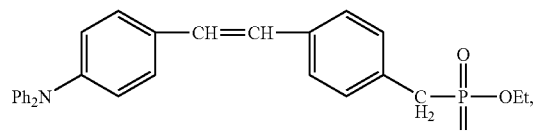

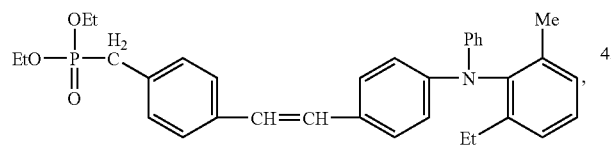

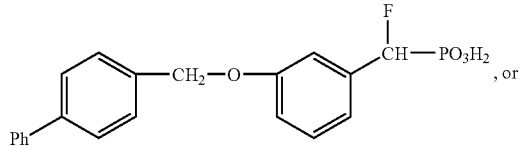

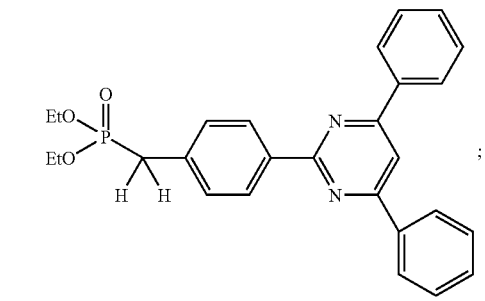

when Q is Q-35 as shown

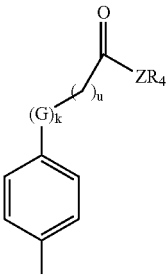

Q-35 (para)

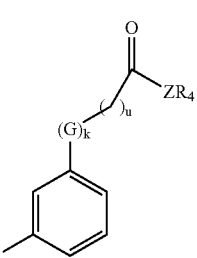

Q-35 (meta)

wherein G is selected from the group consisting of —O—, —S—, and —NR_4—, k is 0 or 1, and u is 1, 2, 3, or 4, then

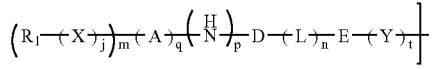

is selected from the group consisting of

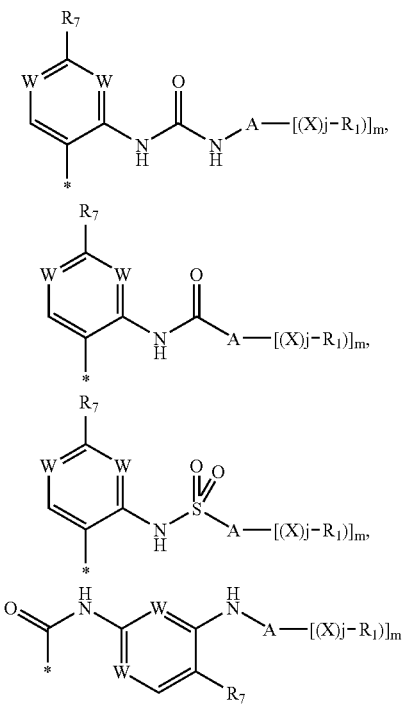

-continued
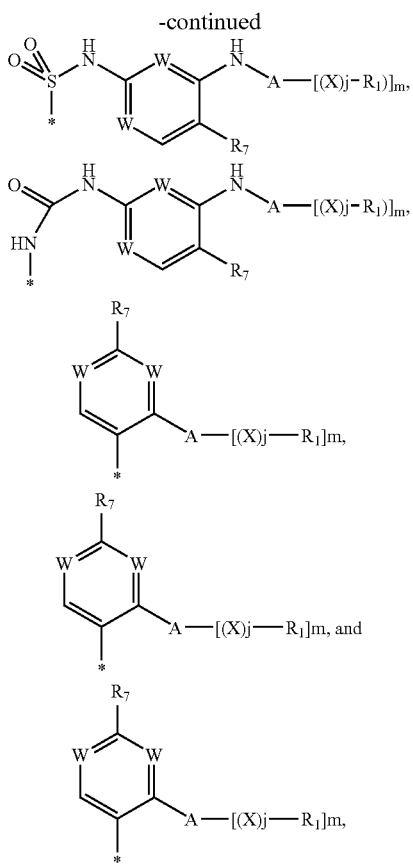
except that the compound of formula (I) is not
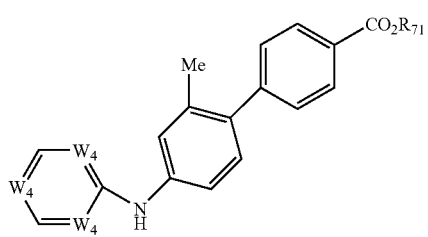
R71 = H, Me
W4 = N, CH
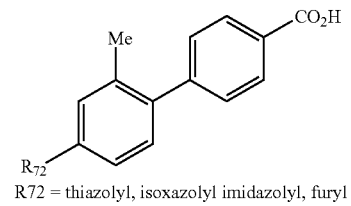
R72 = thiazolyl, isoxazolyl imidazolyl, furyl
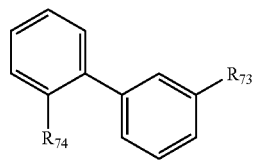
28.1 R73 = —OCH2CO2H
R74 = oxazolyl, imidazolyl
28.2 R73 = CO2Me
R74 = chlorophenyl
-continued
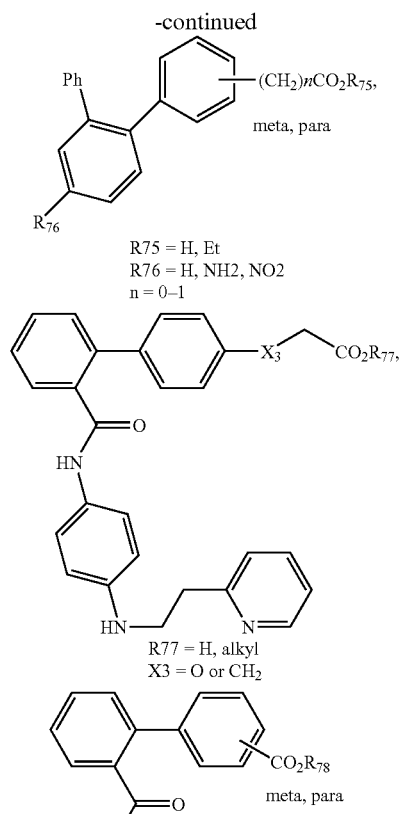
R75 = H, Et
R76 = H, NH2, NO2
n = 0–1
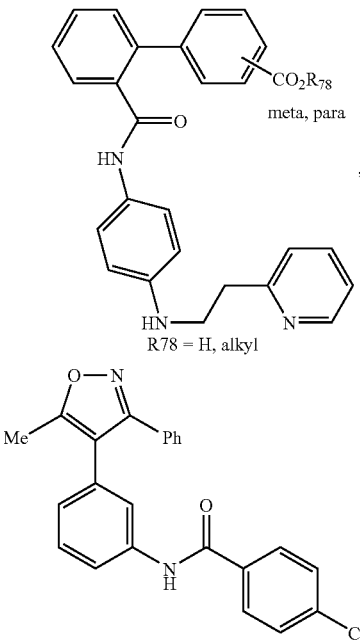
R77 = H, alkyl
X3 = O or CH2
R78 = H, alkyl
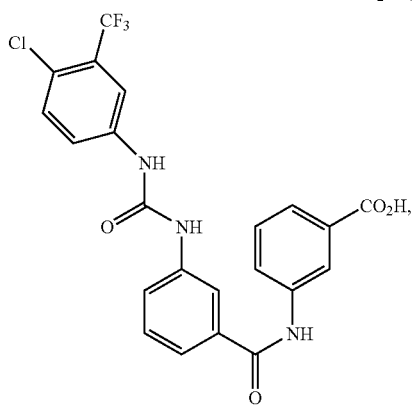

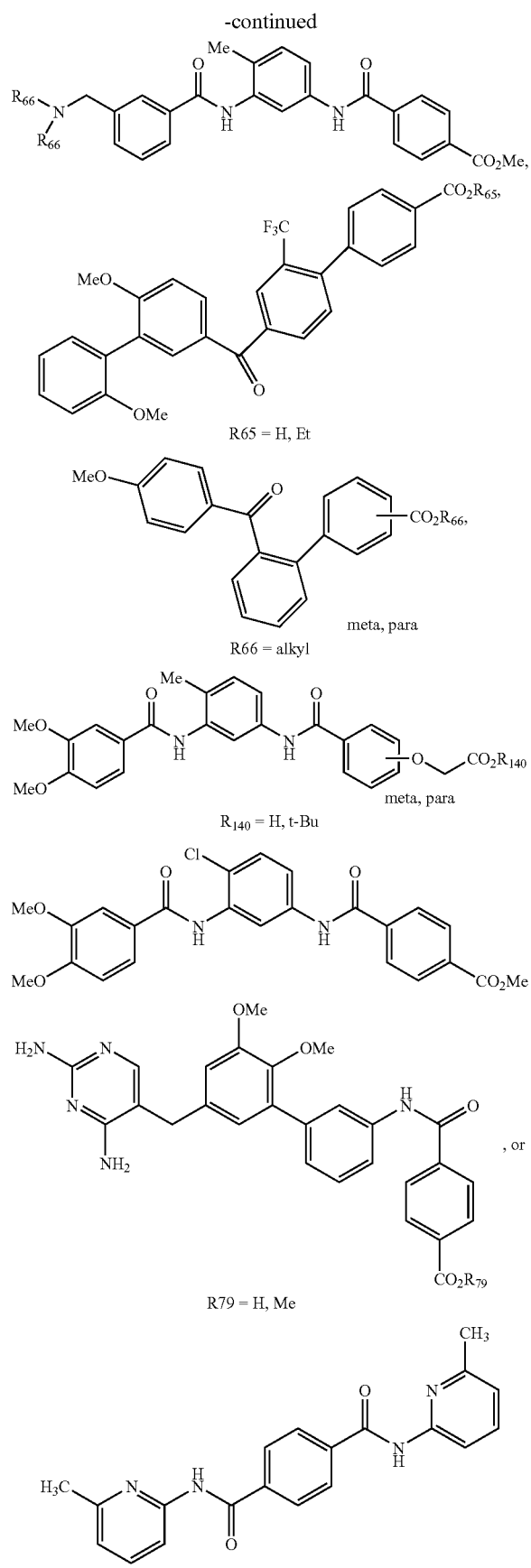

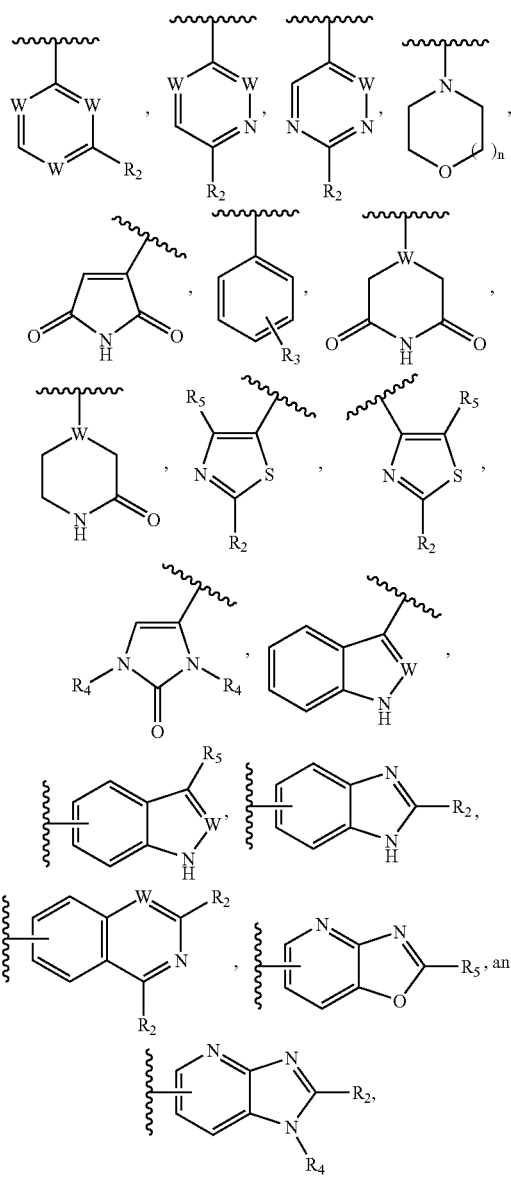

In a preferred embodiment, $R_1$ is selected from the group consisting of 6-5 fused heteroaryls, 6-5 fused heterocyclyls, 5-6 fused heteroaryls, and 5-6 fused heterocyclyls. In a particularly preferred embodiment, $R_1$ is selected from the group consisting of each $R_2$ is individually selected from the group consisting of —H, alkyls (preferably $C_1$-$C_{12}$, and more preferably $C_1$-$C_6$), aminos, alkylaminos (preferably $C_1$-$C_{12}$, and more preferably $C_1$-$C_6$), arylaminos (preferably $C_6$-$C_{18}$, and more preferably $C_6$-$C_{12}$), cycloalkylaminos (preferably $C_3$-$C_{18}$, and more preferably $C_5$-$C_{12}$ and preferably $C_1$-$C_{12}$, and more preferably $C_1$-$C_6$), heterocyclylaminos, halogens, alkoxys (preferably $C_1$-$C_{12}$, and more preferably $C_1$-$C_6$), and hydroxys; and each $R_3$ is individually selected from the group consisting of —H, alkyls (preferably $C_1$-$C_{12}$, and more preferably $C_1$-$C_6$), alkylaminos (preferably $C_1$-$C_{12}$, and more preferably $C_1$-$C_6$), arylaminos (preferably $C_6$-$C_{18}$, and more preferably $C_6$-$C_{12}$), cycloalkylaminos (preferably $C_1$-$C_{12}$, and more preferably $C_1$-$C_6$), heterocyclylaminos, alkoxys (preferably $C_1$-$C_{12}$, and more preferably $C_1$-$C_6$), hydroxys, cyanos, halogens, perfluoroalkyls (preferably $C_1$-$C_{12}$, and more preferably $C_1$-$C_6$), alkylsulfinyls (preferably $C_1$-$C_{12}$, and more preferably $C_1$-$C_6$), alkylsulfonyls (preferably $C_1$-$C_{12}$, and more preferably $C_1$-$C_6$), $R_4NHSO_2$—, and —$NHSO_2R_4$.

In another embodiment, A is selected from the group consisting of phenyl, naphthyl, pyridyl, pyrimidyl, thienyl, furyl, pyrrolyl, thiazolyl, oxazolyl, imidazolyl, indolyl, indazolyl, benzimidazolyl, benzotriazolyl, isoquinolyl, quinolyl, benzothiazolyl, benzofuranyl, benzothienyl, pyrazolylpyrimidinyl, imidazopyrimidinyl, and purinyl.

With respect to the methods of the invention, the activation state of a kinase is determined by the interaction of switch control ligands and complemental switch control pockets. One conformation of the kinase may result from the switch control ligand's interaction with a particular switch control pocket while another conformation may result from the ligand's interaction with a different switch control pocket. Generally interaction of the ligand with one pocket, such as the "on" pocket, results in the kinase assuming an active conformation wherein the kinase is biologically active. Similarly, an inactive conformation (wherein the kinase is not biologically active) is assumed when the ligand interacts with another of the switch control pockets, such as the "off" pocket. The switch control pocket can be selected from the group consisting of simple, composite and combined switch control pockets. Interaction between the switch control ligand and the switch control pockets is dynamic and therefore, the ligand is not always interacting with a switch control pocket. In some instances, the ligand is not in a switch control pocket (such as occurs when the protein is changing from an active conformation to an inactive conformation). In other instances, such as when the ligand is interacting with the environment surrounding the protein in order to determine with which switch control pocket to interact, the ligand is not in a switch control pocket. Interaction of the ligand with particular switch control pockets is controlled in part by the charge status of the amino acid residues of the switch control ligand. When the ligand is in a neutral charge state, it interacts with one of the switch control pockets and when it is in a charged state, it interacts with the other of the switch control pockets. For example, the switch control ligand may have a plurality of OH groups and be in a neutral charge state. This neutral charge state results in a ligand that is more likely to interact with one of the switch control pockets through hydrogen boding between the OH groups and selected residues of the pocket, thereby resulting in whichever protein conformation results from that interaction. However, if the OH groups of the switch control ligand become charged through phosphorylation or some other means, the propensity of the ligand to interact with the other of the switch control pockets will increase and the ligand will interact with this other switch control pocket through complementary covalent binding between the negatively or positively charged residues of the pocket and ligand. This will result in the protein assuming the opposite conformation assumed when the ligand was in a neutral charge state and interacting with the other switch control pocket.

Of course, the conformation of the protein determines the activation state of the protein and can therefore play a role in protein-related diseases, processes, and conditions. For example, if a metabolic process requires a biologically active protein but the protein's switch control ligand remains in the switch control pocket (i.e. the "off" pocket) that results in a biologically inactive protein, that metabolic process cannot occur at a normal rate. Similarly, if a disease is exacerbated by a biologically active protein and the protein's switch control ligand remains in the switch control pocket (i.e. the "on" pocket) that results in the biologically active protein conformation, the disease condition will be worsened. Accordingly, as demonstrated by the present invention, selective modulation of the switch control pocket and switch control ligand by the selective administration of a molecule will play an important role in the treatment and control of protein-related diseases, processes, and conditions.

One aspect of the invention provides a method of modulating the activation state of a kinase, preferably abl or bcr-abl alpha-kinase and including both the consensus wild type sequence and disease polymorphs thereof. The activation state is generally selected from an upregulated or downregulated state. The method generally comprises the step of contacting the kinase with a molecule having the general formula (I). When such contact occurs, the molecule will bind to a particular switch control pocket and the switch control ligand will have a greater propensity to interact with the other of the switch control pockets (i.e., the unoccupied one) and a lesser propensity to interact with the occupied switch control pocket. As a result, the protein will have a greater propensity to assume either an active or inactive conformation (and consequenctly be upregulated or downregulated), depending upon which of the switch control pockets is occupied by the molecule. Thus, contacting the kinase with a molecule modulates that protein's activation state. The molecule can act as an antagonist or an agonist of either switch control pocket. The contact between the molecule and the kinase preferably occurs at a region of a switch control pocket of the kinase and more preferably in an interlobe oxyanion pocket of the kinase. In some instances, the contact between the molecule and the pocket also results in the alteration of the conformation of other adjacent sites and pockets, such as an ATP active site. Such an alteration can also effect regulation and modulation of the active state of the protein. Preferably, the region of the switch control pocket of the kinase comprises an amino acid residue sequence operable for binding to the Formula I molecule. Such binding can occur between the molecule and a specific region of the switch control pocket with preferred regions including the α-C helix, the α-D helix, the catalytic loop, the activation loop, and the C-terminal residues or C-lobe residues (all residues located downstream (toward the C-end) from the Activation loop), and combinations thereof. When the binding region is the α-C helix, one preferred binding sequence in this helix is the sequence VEEFLKEAAVM, (SEQ ID NO. 2). When the binding region is the catalytic loop, one preferred binding sequence in this loop is HRDLAARNXL (SEQ ID NO. 3). When the binding region is the activation loop, one preferred binding sequence in this loop is a sequence selected from the group consisting of DFGLSRLMT (SEQ ID NO. 4), GDTYTAH (SEQ ID NO. 5), and combinations thereof. When the binding region is in the C-lobe residues, one preferred binding residue is F, found at position 416 relative to the full length sequence (residue 194 in SEQ ID NO. 1). When a biologically inactive protein conformation is desired, molecules which interact with the switch control pocket that normally results in a biologically active protein conformation (when interacting with the switch control ligand) will be selected. Similarly, when a biologically active protein conformation is desired, molecules which interact with the switch control pocket that normally results in a biologically inactive protein conformation (when interacting with the switch control ligand) will be selected. Thus, the propensity of the protein to assume a desired conformation will be modulated by administration of the molecule. In preferred forms, the molecule will be administered to an individual undergoing treatment for cancer including but not limited to chronic myelogeneous leukemia and stromal gastrointestinal tumors. In such forms, it will be desired to select molecules that interact with the switch control pocket that generally leads to a biologically active protein conformation so that the protein will have the propensity to assume the biologically inactive form and thereby alleviate the condition. It is contemplated that the molecules of the present invention will be administerable in any conventional form including oral, parenteral, inhalation, and subcutaneous. It is preferred for the administration to be in the oral form. Preferred molecules include the preferred formula (I) compounds discussed above.

Another aspect of the present invention provides a method of treating cancer comprising the step of administering a molecule having the structure of the formula (I) compounds to the individual. Such conditions are often the result of an overproduction of the biologically active form of a protein, including kinases. For example, a hallmark feature of chronic myelogeneous leukemia involves a reciprocal chromosomal translocation involving human chromosomes 9 and 22. This mutation fuses a segment of the bcr gene upstream of the second exon of the c-abl nonreceptor tyrosine kinase gene. This fusion protein is called bcr-abl. While the normal c-abl gene and its protein are tightly controlled in normal cells, the fusion protein product bcr-abl presents with elevated, constitutive kinase activity. It is this activity that enables bcr-abl fusion protein to transform cells and cause malignancy. Thus, the invention discloses and utilizes small molecule inhibitors of bcr-abl kinase. These inhibitors contain functionality which enable them to bind to an binding region, preferably an interlobe oxyanion regulator pocket in abl kinase: The inhibitors may also contain functionality which bind to the ATP pocket or other kinase amino acid residues taken from the N-lobe or C-lobe of the kinase.

The administering step generally includes the step of causing said molecule to contact a kinase involved with elevated kinase activity such as that found in cancer. A particularly preferred kinase to contact is bcr-abl kinase. When the contact is between the molecule and a kinase, the contact preferably occurs in a binding region (preferably an interlobe oxyanion pocket of the kinase) that includes an amino acid residue sequence operable for binding to the Formula I molecule. Preferred binding regions of the interlobe oxyanion pocket include the α-C helix region, the catalytic loop, the activation loop, the C-terminal lobe or residues, and combinations thereof. When the binding region is the α-C helix, one preferred binding sequence in this helix is the sequence VEEFLKEAAVM (SEQ ID NO. 2). When the binding region is the catalytic loop, one preferred binding sequence in this loop is HRDLAARNXL (SEQ ID NO. 3). When the binding region is the activation loop, one preferred binding sequence in this loop is a sequence selected from the group consisting of DFGLSR-LMT (SEQ ID NO. 4), GDTYTAH (SEQ ID NO. 5), and combinations thereof. A preferred residue with which to bind in the C-terminal lobe is F.

Such a method permits treatment of cancer by virtue of the modulation of the activation state of a kinase by contacting the kinase with a molecule that associates with the switch control pocket that normally leads to a biologically active form of the kinase when interacting with the switch control ligand. Because the ligand cannot easily interact with the switch control pocket associated with or occupied by the molecule, the ligand tends to interact with the switch control pocket leading to the biologically inactive form of the protein, with the attendant result of a decrease in the amount of biologically active protein. Preferably, the cancer is selected from the group consisting of chronic mylogeneous leukemia and stromal gastrointestinal tumors. As with the other methods of the invention, the molecules may be administered in any conventional form, with any conventional excipients or ingredients. However, it is preferred to administer the molecule in an oral dosage form. Preferred molecules are again selected from the group consisting of the preferred formula (I) compounds as discussed above.

BRIEF DESCRIPTION OF THE DRAWINGS

FIG. 4a is an enlarged schematic view illustrating a representative binding between the phosphorylated residues of the switch control ligand, and complemental residues from the on switch control pocket;

DETAILED DESCRIPTION OF THE PREFERRED EMBODIMENTS

Figure 1:
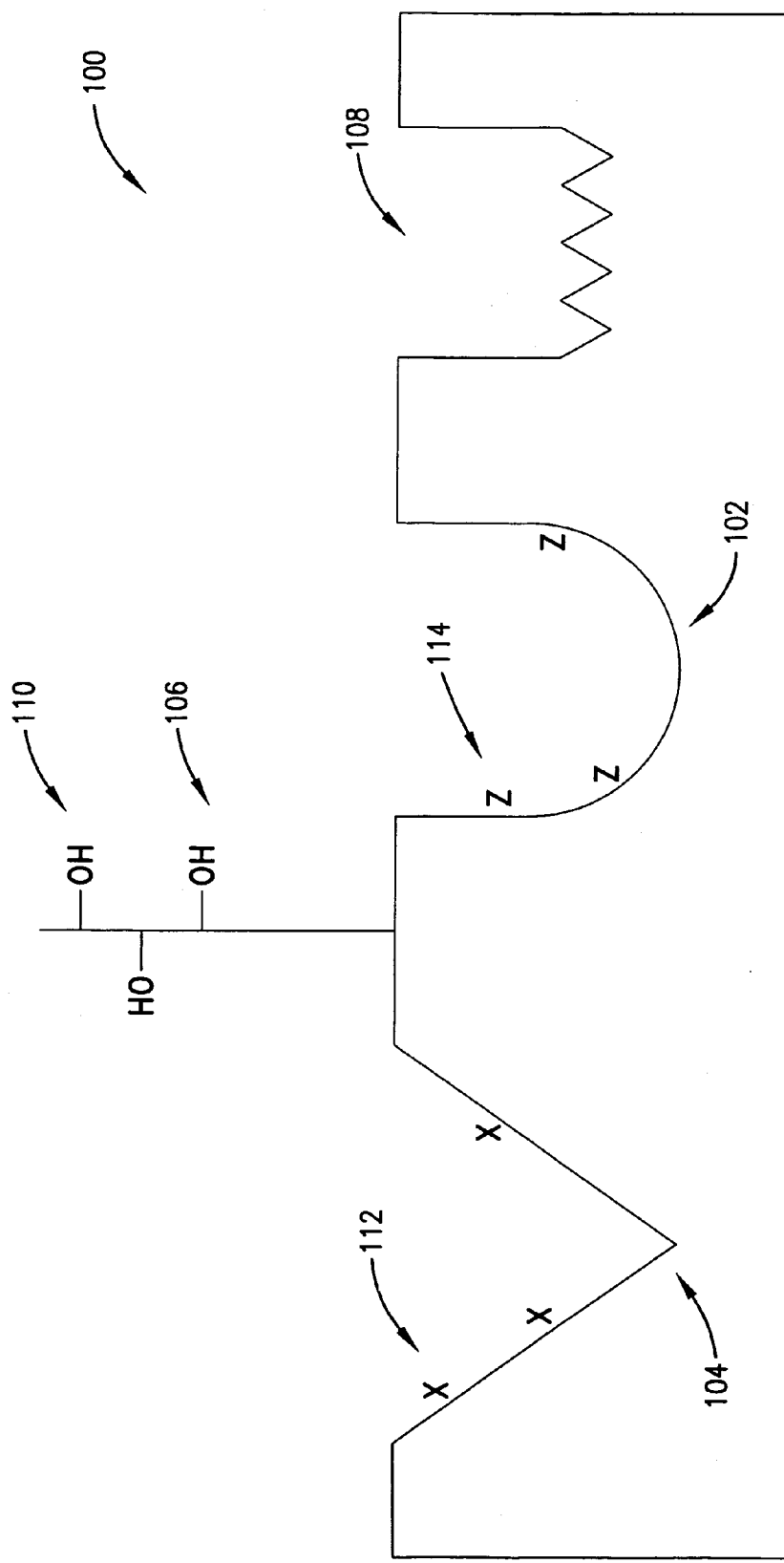
FIG. 1 is a schematic representation of a naturally occurring mammalian protein in accordance with the invention including "on" and "off" switch control pockets, a transiently modifiable switch control ligand, and an active ATP site.

The present invention provides a way of rationally developing new small molecule modulators which interact with naturally occurring proteins (e.g., mammalian, and especially human proteins) in order to modulate the activity of the proteins. Novel protein-small molecule adducts are also provided. The invention preferably makes use of naturally occurring proteins having a conformational property whereby the proteins change their conformations in vivo with a corresponding change in protein activity. For example, a given enzyme protein in one conformation may be biologically upregulated, while in another conformation, the same protein may be biologically downregulated. The invention preferably makes use of one mechanism of conformation change utilized by naturally occurring proteins, through the interaction of what are termed "switch control ligands" and "switch control pockets" within the protein.

As used herein, "switch control ligand" means a region or domain within a naturally occurring protein and having one or more amino acid residues therein which are transiently modified in vivo between individual states by biochemical modification, typically phosphorylation, sulfation, acylation or oxidation. Similarly, "switch control pocket" means a plurality of contiguous or non-contiguous amino acid residues within a naturally occurring protein and comprising residues capable of binding in vivo with transiently modified residues of a switch control ligand in one of the individual states thereof in order to induce or restrict the conformation of the protein and thereby modulate the biological activity of the protein, and/or which is capable of binding with a non-naturally occurring switch control modulator molecule to induce or restrict a protein conformation and thereby modulate the biological activity of the protein.

A protein-modulator adduct in accordance with the invention comprises a naturally occurring protein having a switch control pocket with a non-naturally occurring molecule bound to the protein at the region of said switch control pocket, said molecule serving to at least partially regulate the biological activity of said protein by inducing or restricting the conformation of the protein. Preferably, the protein also has a corresponding switch control ligand, the ligand interacting in vivo with the pocket to regulate the conformation and biological activity of the protein such that the protein will assume a first conformation and a first biological activity upon the ligand-pocket interaction, and will assume a second, different conformation and biological activity in the absence of the ligand-pocket interaction.

The nature of the switch control ligand/switch control pocket interaction may be understood from a consideration of schematic FIGS. 1-4. Specifically, in FIG. 1, a protein 100 is illustrated in schematic form to include an "on" switch control pocket 102, and "off" switch control pocket 104, and a switch control ligand 106. In addition, the schematically depicted protein also includes an ATP active site 108. In the exemplary protein of FIG. 1, the ligand 106 has three amino acid residues with side chain OH groups 110. The off pocket 104 contains corresponding X residues 112 and the on pocket 102 has Z residues 114. In the exemplary instance, the protein 100 will change its conformation depending upon the charge status of the OH groups 110 on ligand 106, i.e., when the OH groups are unmodified, a neutral charge is presented, but when these groups are phosphorylated a negative charge is presented.

Figure 2:
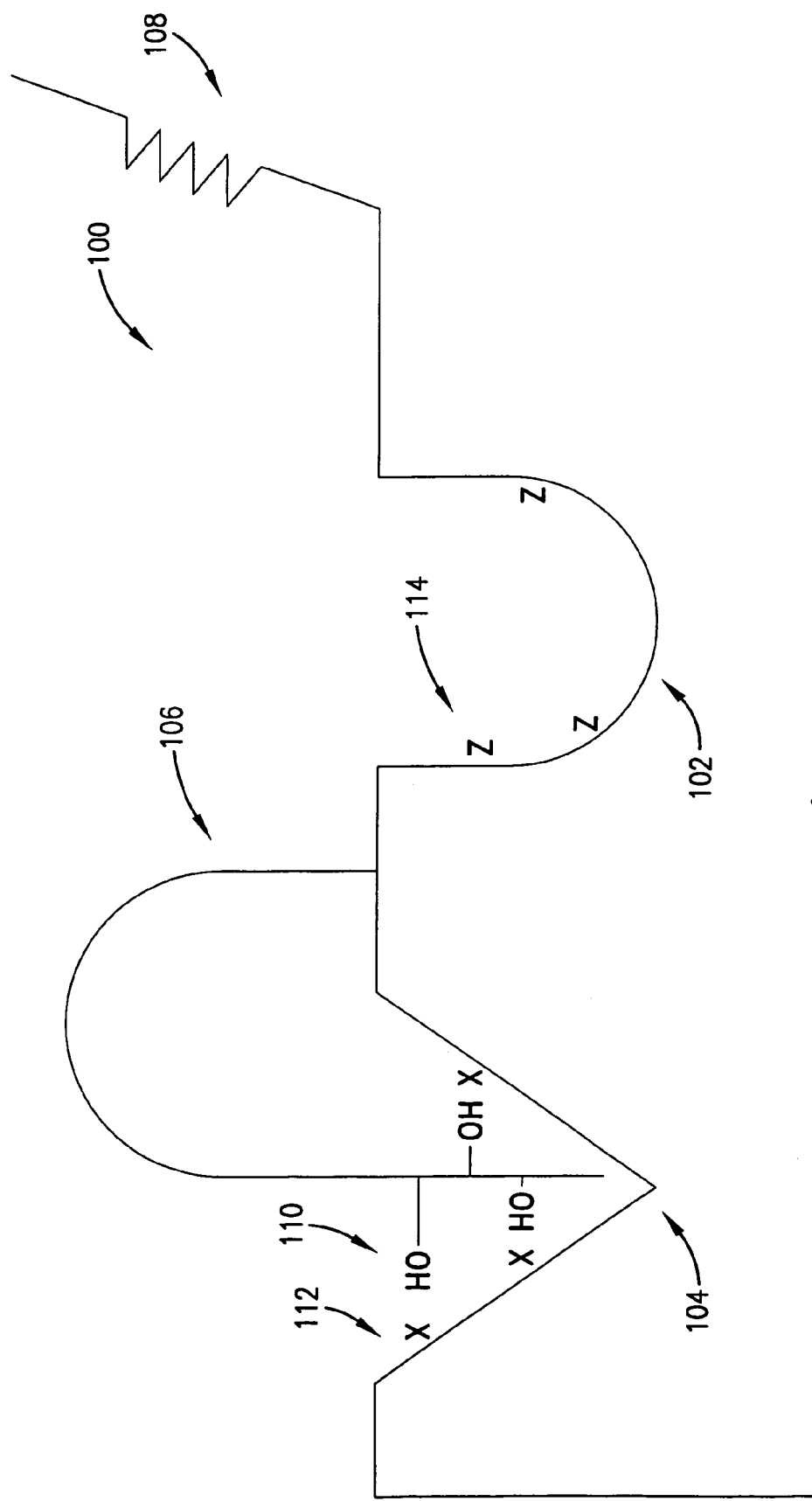
FIG. 2 is a schematic representation of the protein of FIG. 1, wherein the switch control ligand is illustrated in a binding relationship with the off switch control pocket, thereby causing the protein to assume a first biologically downregulated conformation.
Figure 3:
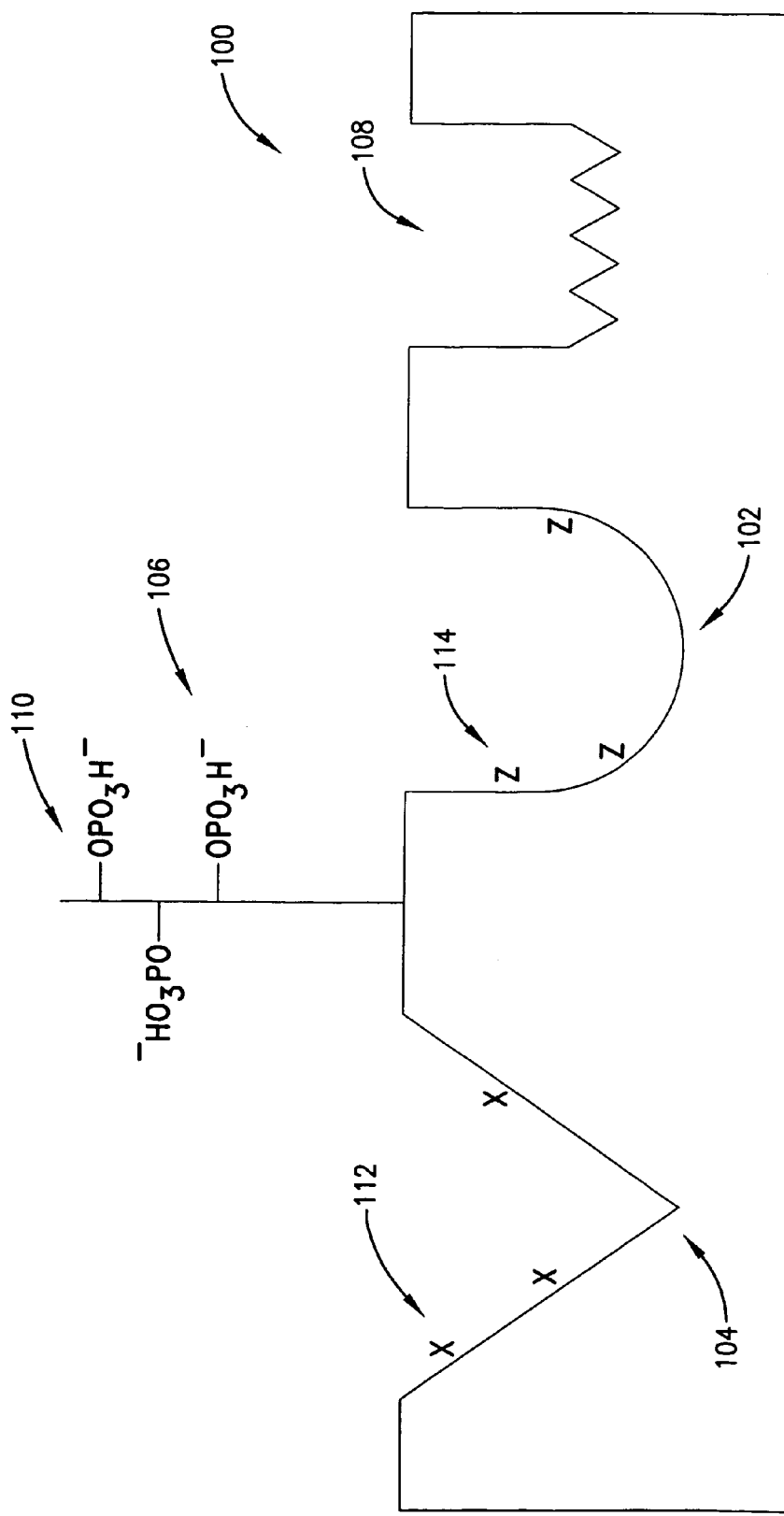
FIG. 3 is a view similar to that of FIG. 1, but illustrating the switch control ligand in its charged-modified condition wherein the OH groups of-certain amino acid residues have been phosphorylated.
Figure 4:
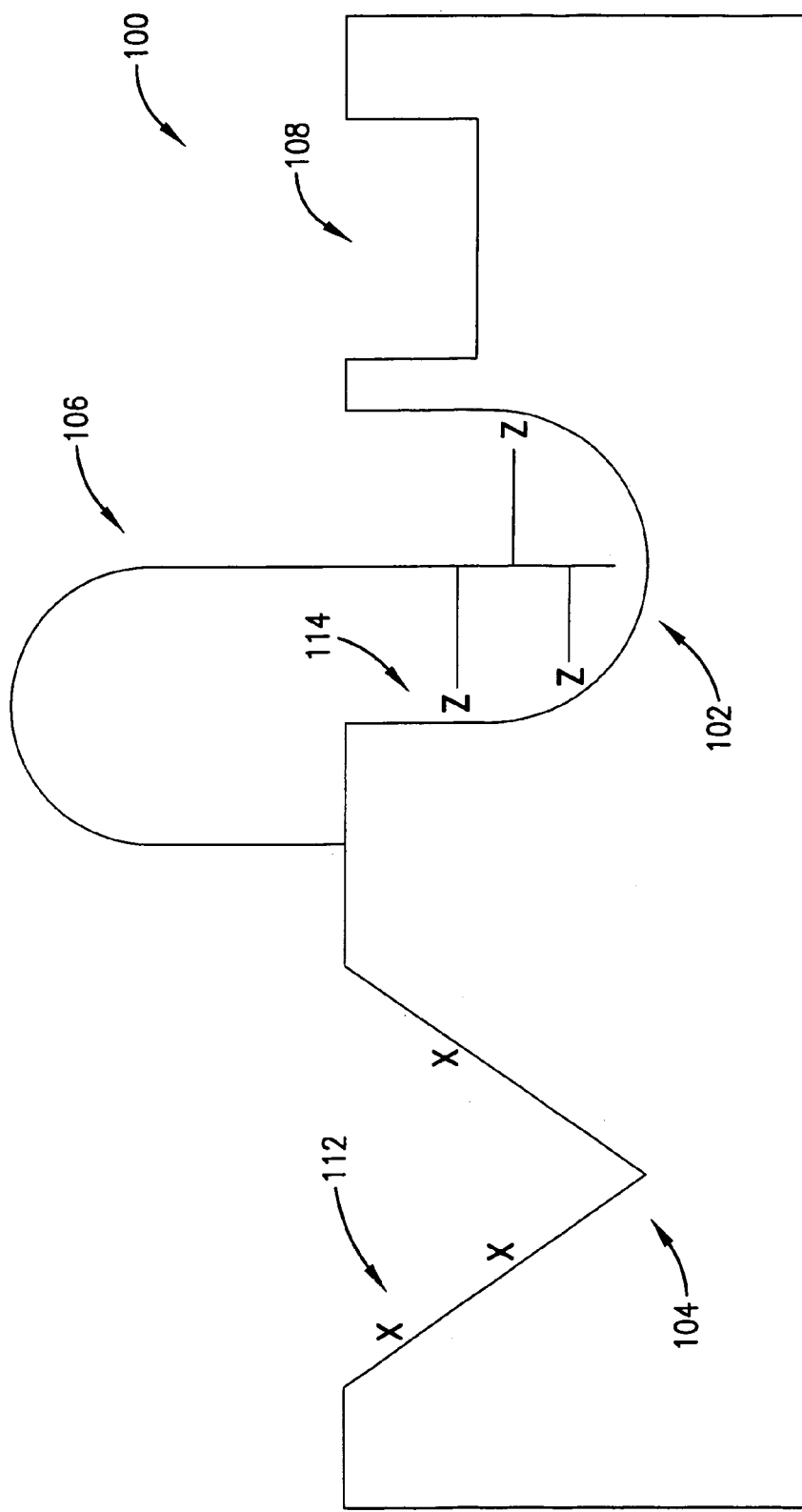
FIG. 4 is a view similar to that of FIG. 2, but depicting the protein wherein the switch control ligand is in a binding relationship with the on switch control pocket, thereby causing the protein to assume a second biologically-active conformation different than the first conformation of FIG. 2.
Figure 5:
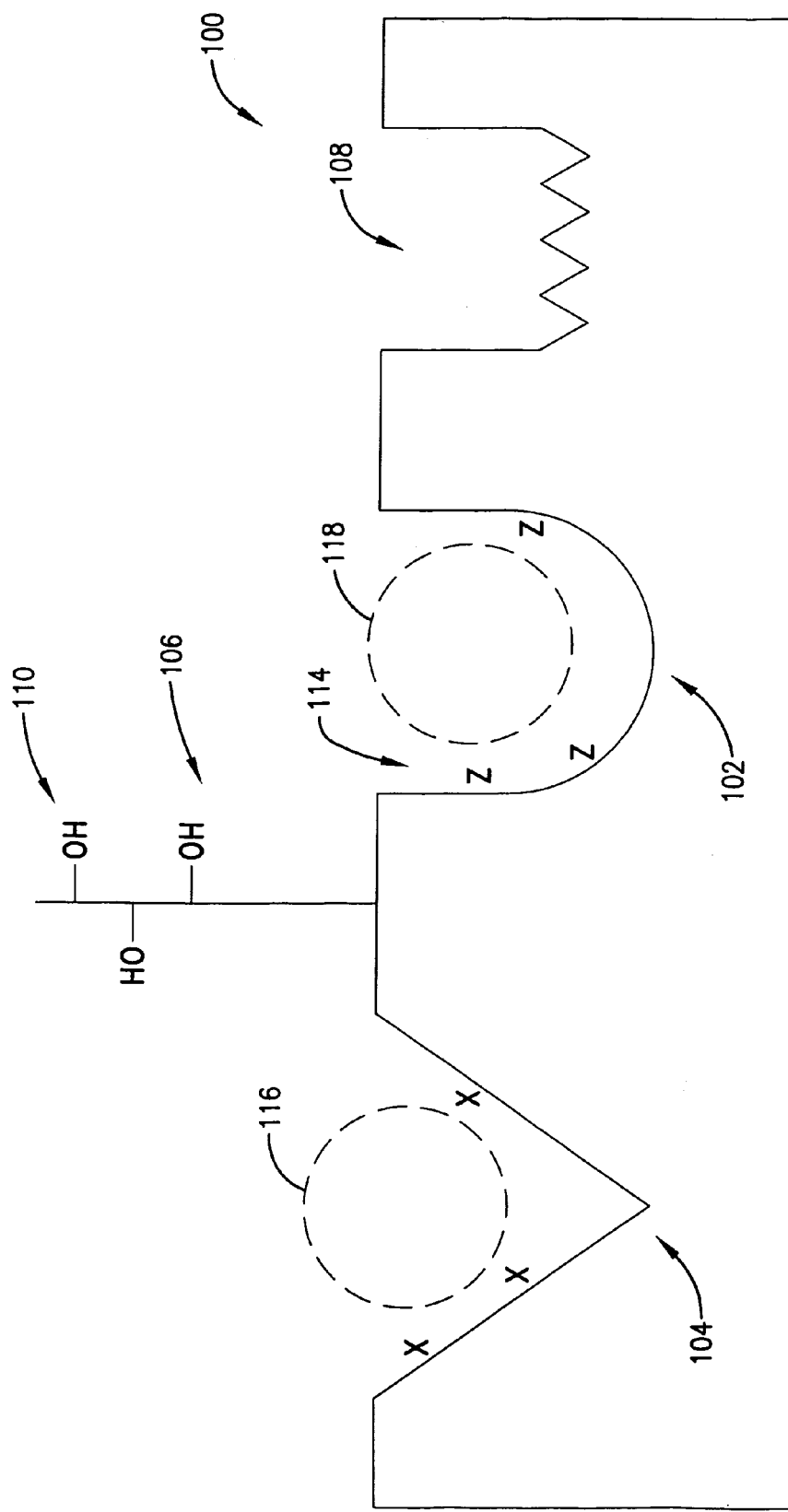
FIG. 5 is a view similar to that of FIG. 1, but illustrating in schematic form possible small molecule compounds in a binding relationship with the on and off switch control pockets.

The functionality of the pockets 102, 104 and ligand 106 can be understood from a consideration of FIGS. 2-4. In FIG. 2, the ligand 106 is shown operatively interacted with the off pocket 104 such that the OH groups 110 interact with the X residues 112 forming a part of the pocket 104. Such interaction is primarily by virtue of hydrogen bonding between the OH groups 110 and the residues 112. As seen, this ligand/pocket interaction causes the protein 100 to assume a conformation different from that seen in FIG. 1 and corresponding to the off or biologically downregulated conformation of the protein.

FIG. 3 illustrates the situation where the ligand 106 has shifted from the off pocket interaction conformation of FIG. 2 and the OH groups 110 have been phosphorylated, giving a negative charge to the ligand. In this condition, the ligand has a strong propensity to interact with on pocket 102, to thereby change the protein conformation to the on or biologically upregulated state (FIG. 4). FIG. 4a illustrates that the phosphorylated groups on the ligand 106 are attracted to positively charged residues 114 to achieve an ionic-like stabilizing bond. Note that in the on conformation of FIG. 4, the protein conformation is different than the off conformation of FIG. 2, and that the ATP active site is available and the protein is functional as a kinase enzyme.

Figure 6:
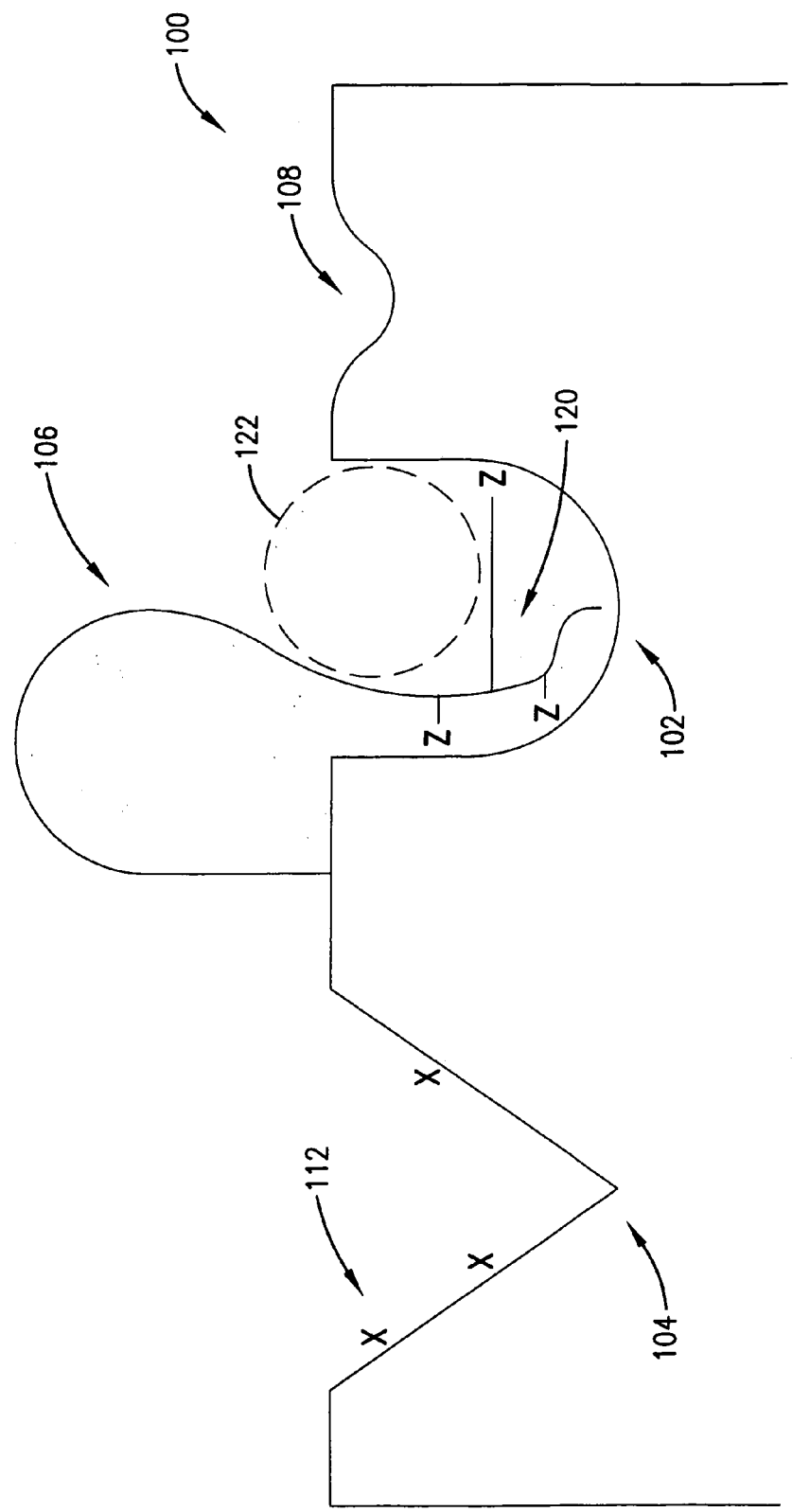
FIG. 6 is a schematic view of the protein in a situation where a composite switch control pocket is formed with portions of the switch control ligand and the on switch control pocket, and with a small molecule in binding relationship with the composite pocket.

FIGS. 1-4 illustrate a simple situation where the protein exhibits discrete pockets 102 and 104 and ligand 106. However, in many cases a more complex switch control pocket pattern is observed. FIG. 6 illustrates a situation where an appropriate pocket for small molecule interaction is formed from amino acid residues taken both from ligand 106 and, for example, from pocket 102. This is termed a "composite switch control pocket" made up of residues from both the ligand 106 and a pocket, and is referred to by the numeral 120. A small molecule 122 is illustrated which interacts with the pocket 120 for protein modulation purposes.

Figure 7:
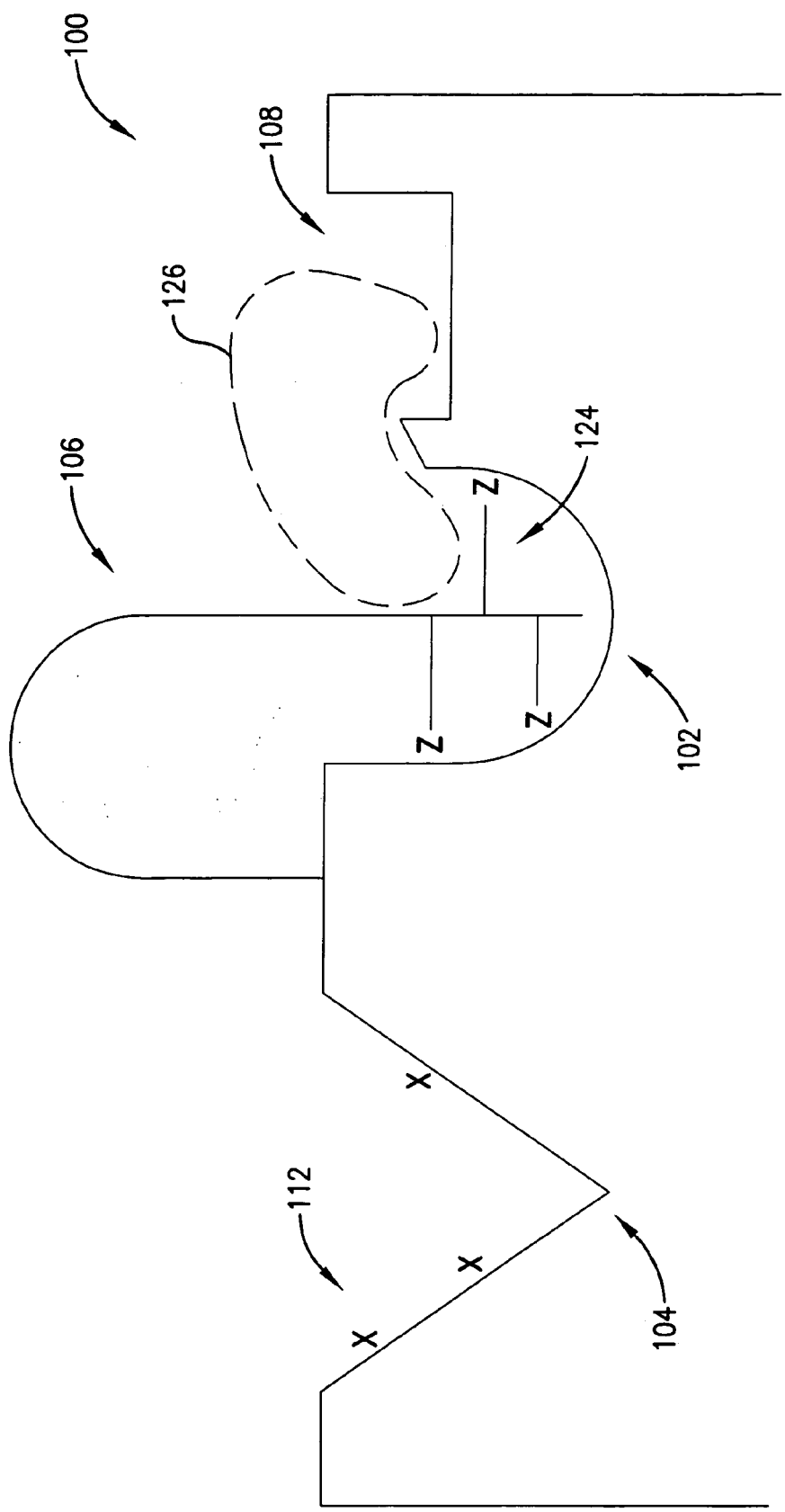
FIG. 7 is a schematic view of the protein in a situation where a combined switch control pocket is formed with portions of the on switch control pocket, the switch control ligand sequence, and the active ATP site, and with a small molecule in binding relationship with the combined switch control pocket.

Another more complex switch pocket is depicted in FIG. 7 wherein the pocket includes residues from on pocket 102, and ATP site 108 to create what is termed a "combined switch control pocket." Such a combined pocket is referred to as numeral 124 and may also include residues from ligand 106. An appropriate small molecule 126 is illustrated with pocket 124 for protein modulation purposes.

It will thus be appreciated that while in the simple pocket situation of FIGS. 1-4, the small molecule will interact with the simple pocket 102 or 104, in the more complex situations of FIGS. 6 and 7 the interactive pockets are in the regions of the pockets 120 or 124. Thus, broadly the small molecules interact "at the region" of the respective switch control pocket.

General Synthesis of Compounds

In the synthetic schemes of this section, q is 0 or 1. When q=0, the substituent is replaced by a synthetically non-interfering group $R_7$.

Compounds of Formula I wherein D is taken from D-1 or D-2 and Y is alkylene are prepared according to the synthetic route shown in Scheme 1.1. Reaction of isothiocyanate 1 with chlorine, followed by addition of isocyanate 2 affords 3-oxo-thiadiazolium salt 3. Quenching of the reaction with air affords compounds of Formula I-4. Alternatively, reaction of isothiocyanate 1 with isothiocyanate 5 under the reaction conditions gives rise to compounds of Formula I-7. See A. Martinez et al, *Journal of Medicinal Chemistry* (2002) 45:1292.

Intermediates 1, 2 and 5 are commercially available or prepared according to Scheme 1.2. Reaction of amine 8 with phosgene or a phosgene equivalent affords isocyanate 2.

Similarly, reaction of amine 8 with thiophosgene affords isothiocyanate 5. Amine 8 is prepared by palladium(0) catalyzed amination of 9, wherein Q is a group capable of oxidative insertion into palladium(0), according to methodology reported by S. Buchwald. See M. Wolter et al, *Organic Letters* (2002) 4:973; B. H. Yang and S. Buchwald, *Journal of Organometallic Chemistry* (1999) 576(1-2):125. In this reaction sequence, P is a suitable amine protecting group. Use of and removal of amine protecting groups is accomplished by methodology reported in the literature (Protective Groups in Organic Synthesis, Peter G. M. Wutts, Theodora Greene (Editors) 3rd edition (April 1999) Wiley, John & Sons, Incorporated; ISBN: 0471160199). Starting compounds 9 are commercially available or readily prepared by one of ordinary skill in the art: See March's Advanced Organic Chemistry: Reactions, Mechanisms, and Structure, Michael B. Smith & Jerry March (Editors) 5th edition (January 2001) Wiley John & Sons; ISBN: 0471585890.

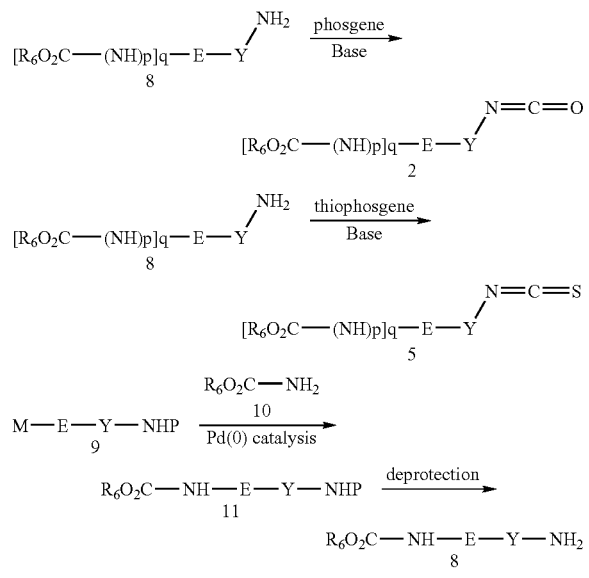

Compounds of Formula I wherein Q is taken from Q-1 or Q-2 and Y is alkylene are also available via the synthetic route shown in Scheme 1.3. Reaction of amine 8 with isocyanate or isothiocyanate 2a yields the urea/thiourea 8a which can be cyclized by the addition of chlorocarbonyl sulfenyl chloride. See GB1115350 and U.S. Pat. No. 3,818,024, Revankar et. al U.S. Pat. No. 4,093,624, and Klayman et. al *JOC* 1972, 37(10), 1532 for further details. Where $R_4$ is a readily removable protecting group (e.g. R=3,4-d-methoxybenzyl amine), the action of mild, acidic deprotection conditions such as CAN or TFA will reveal the parent ring system of I-4 (X=O) and I-7 (X=S).

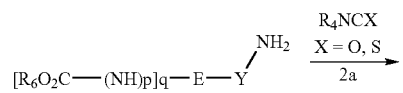

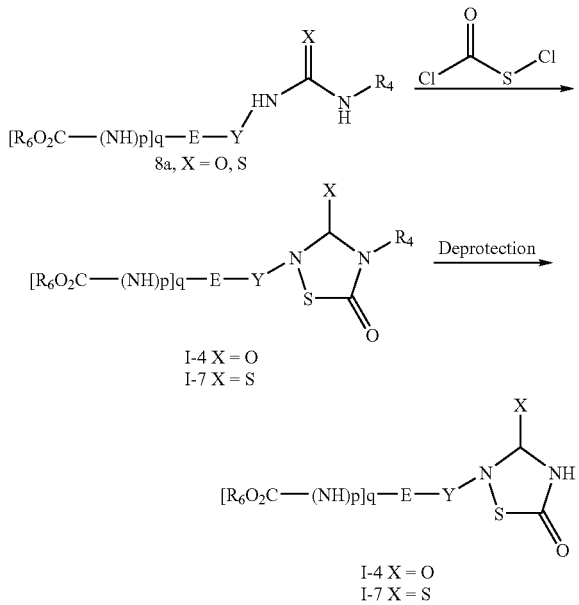

Compounds of Formula I wherein Q is taken from Q-1 or Q-2 and Y is alkylene are also available as shown in Scheme 1.4. Condensation of isocyanate or isothiocyanate 2a with amine $R_5NH_2$ yields urea/thiourea 2b, which, when reacted with chlorocarbonyl sulfenyl chloride according to GB1115350 and U.S. Pat. No. 3,818,024 yields 2c. Where $R_4$ is a readily removable protecting group (e.g., R=3,4-d-methoxybenzyl amine), the action of mild, acidic deprotection conditions such as CAN or TFA will reveal the parent ring system of 2d. Reaction of 2d with NaH in DMF, and displacement wherein M is a suitable leaving group such as chloride, bromide or iodide yields I-4 (X=O) and I-7 (X=S).

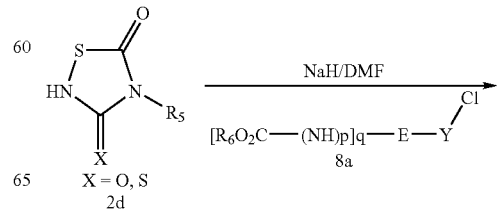

-continued

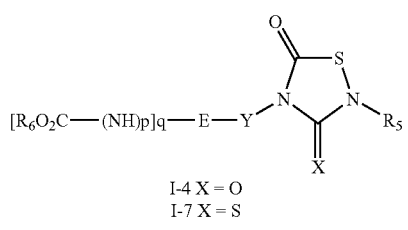

I-4 X = O
I-7 X = S

Compounds of Formula I wherein Q is taken from Q-1' or Q-2' and Y is alkylene are available via the synthetic route shown in Scheme 1.5. Condensation of isocyanate or isothiocyanate 2a with ammonia yields urea/thiourea 2e, which, when reacted with chlorocarbonyl sulfenyl chloride according to GB1115350 and U.S. Pat. No. 3,818,024 yields 2f. Reaction of 2f with NaH in DMF, and displacement wherein M is a suitable leaving group such as chloride, bromide or iodide yields 1-4' (X=O) and I-7' (X=S).

Scheme 1.5

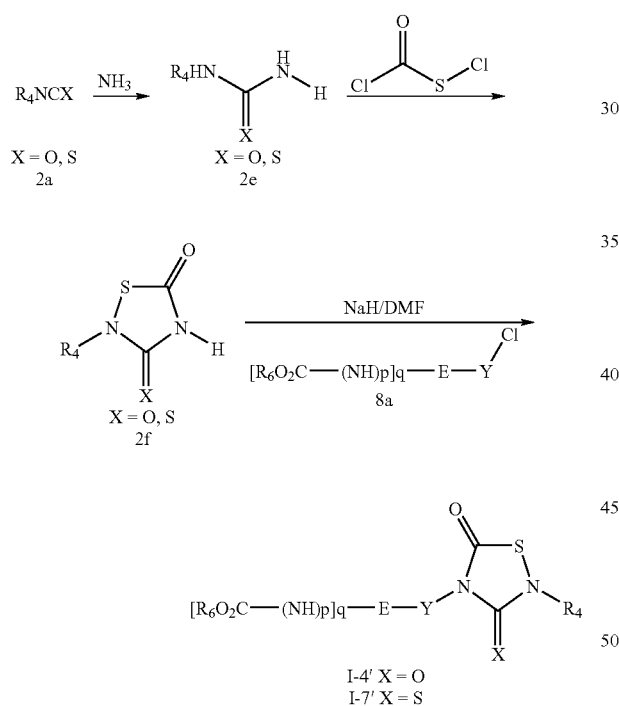

I-4' X = O
I-7' X = S

Compounds of Formula I wherein Q is taken from Q-3 or Q-4 and Y is alkylene, are prepared according to the synthetic route shown in Schemes 2.1 and 2.2, respectively. Reaction of 12, wherein M is a suitable leaving group, with the carbamate-protected hydrazine 13 affords intermediate 14. Reaction of 14 with an isocyanate gives rise to intermediate 15. Thermal cyclization of 15 affords 1,2,4-triazolidinedione of Formula I-16. By analogy, scheme 2.2 illustrates the preparation of 3-thio-5-oxo-1,2,4-triazolidines of Formula I-18 by reaction of intermediate 14 with an isothiocyanate and subsequent thermal cyclization.

Scheme 2.1

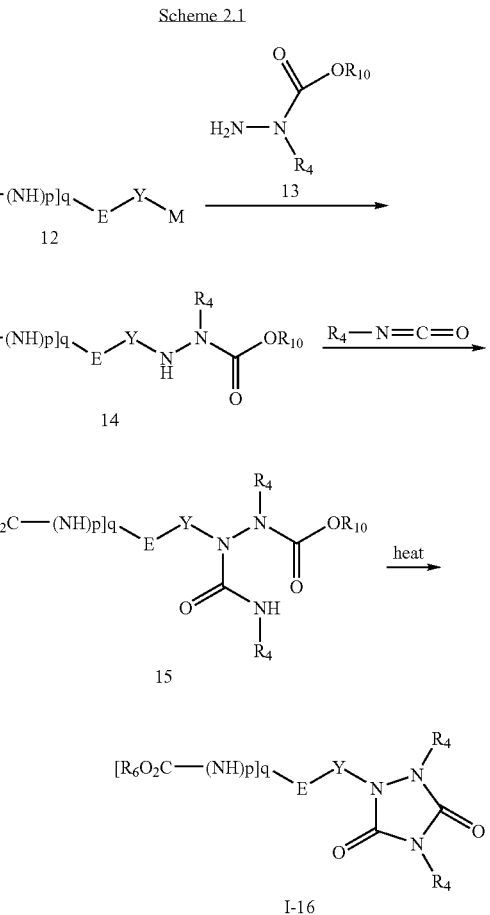

Scheme 2.2

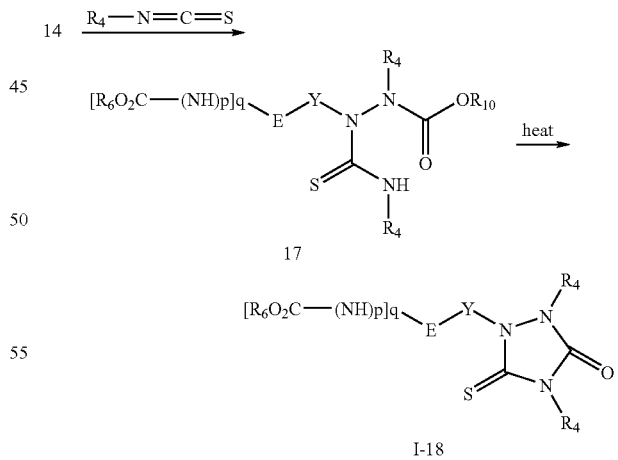

Intermediates 12 wherein p is 1 are readily available or are prepared by reaction of 19 with carbamates 10 under palladium (0)-catalyzed conditions. $M_1$ is a group which oxidatively inserts palladium(0) over group M. $M_1$ is preferably iodo or bromo. Compounds 19 are either commercially available or prepared by one of ordinary skill in the art.

37

Scheme 2.3

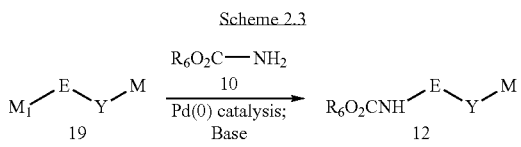

38

Compounds of Formula I wherein Q is taken from Q-3 or Q-4 and Y is alkylene are also prepared according to the synthetic route shown in Scheme 2.4. Oxidation of amine $R_4NH_2$ to the corresponding hydrazine, condensation with ethyl chloroformate subsequent heating yields 1,2,4-triazolidinedione 15a. After the action of NaH in DMF, displacement wherein M is a suitable leaving group such as chloride, bromide or iodide yields I-16 (X=O) and I-18 (X=S).

Scheme 2.4

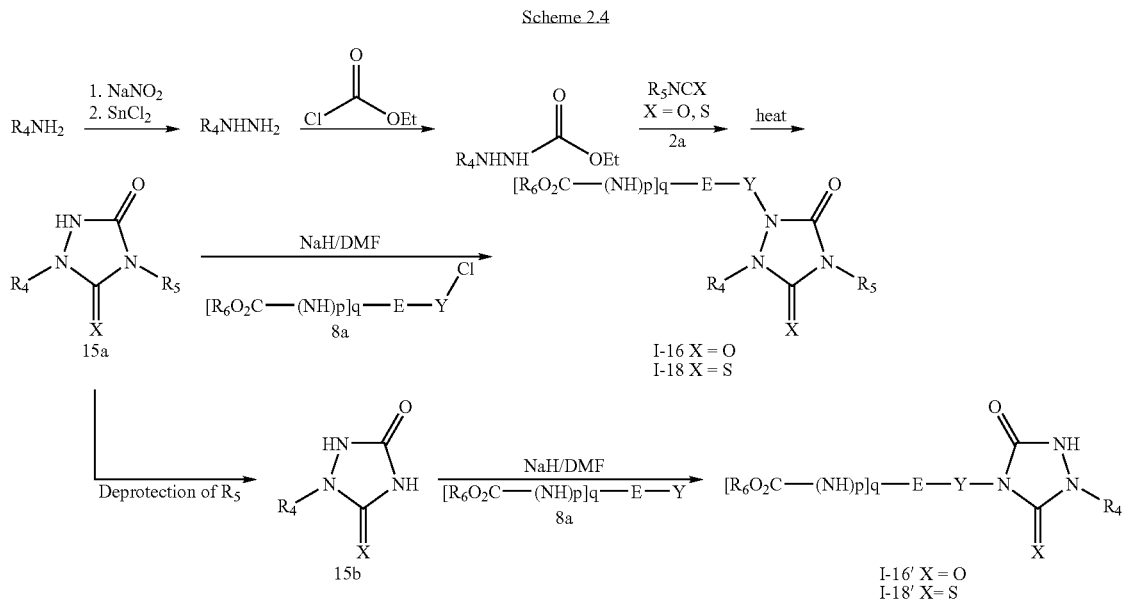

Compounds of Formula I wherein Q is taken from Q-3' or Q-4' and Y is alkylene are also prepared according to the synthetic route shown in Scheme 2.4. When $R_5$ is a readily removable protecting group (e.g. R=3,4-d-methoxybenzyl amine), the action of mild, acidic deprotection conditions such as CAN or TFA on 15a will reveal 1,2,4-triazolidinedione 15b. After deprotonation of 15b by NaH in DMF, displacement wherein M is a suitable leaving group such as chloride, bromide or iodide yields I-16' (X=O) and I-18' (X=S).

Compounds of Formula I wherein Q is taken from Q-5 or Q-6 and Y is alkylene are prepared according to the synthetic route shown in Scheme 3. Reaction of hydrazine 20 with chlorosulfonylisocyanate and base, such as triethylamine, gives rise to a mixture of intermediates 21A and 21B which are not isolated but undergo cyclization in situ to afford compounds of Formulae I-22A and I-22B. Compounds I-22A and I-22B are separated by chromatography or fractional crystallization. Optionally, compounds I-22A and I-22B can undergo Mitsunobu reaction with alcohols $R_4OH$ to give compounds of Formulae I-23A and I-23B. Compounds 20 are prepared by acid-catalyzed deprotection of t-butyl carbamates of structure 14, wherein $R_{10}$ is t-butyl.

Scheme 3

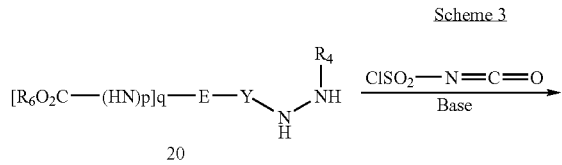

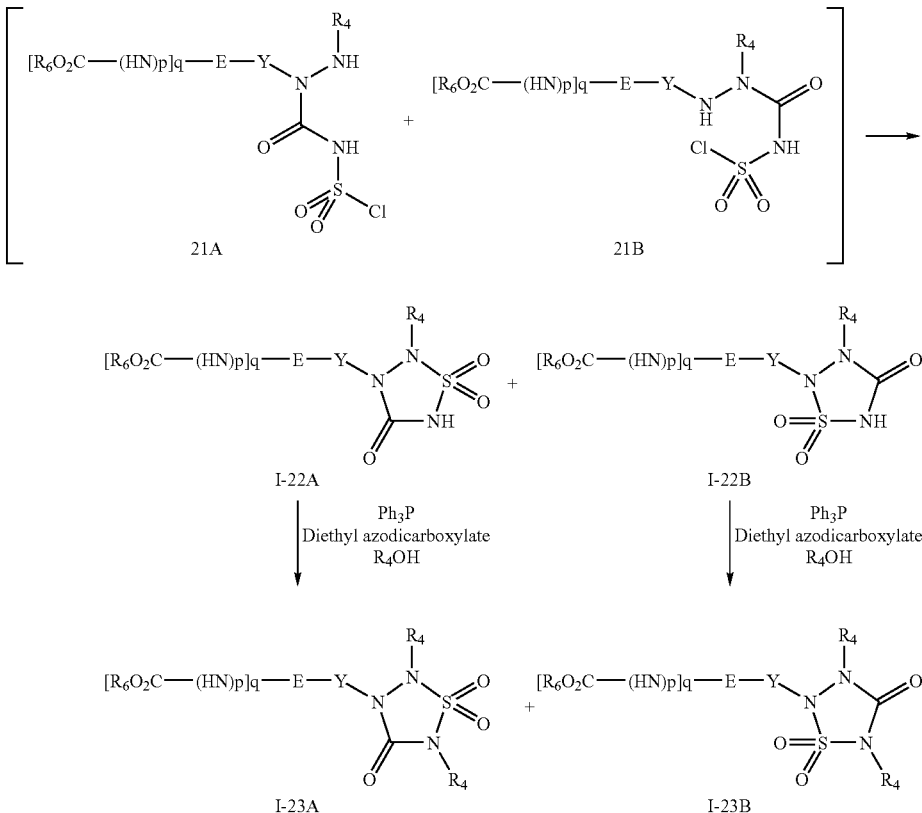

Compounds of Formula I wherein Q is Q-7 and Y is alkylene are prepared as shown in Scheme 4. Reaction of amine 8 with maleimide 24, wherein M is a suitable leaving group, affords compounds of Formula I-25. Reaction of compound 26, wherein M is a group which can oxidatively insert Pd(0), can participate in a Heck reaction with maleimide 27, affording compounds of Formula I-28. Maleimides 24 and 27 are commercially available or prepared by one of ordinary skill in the art.

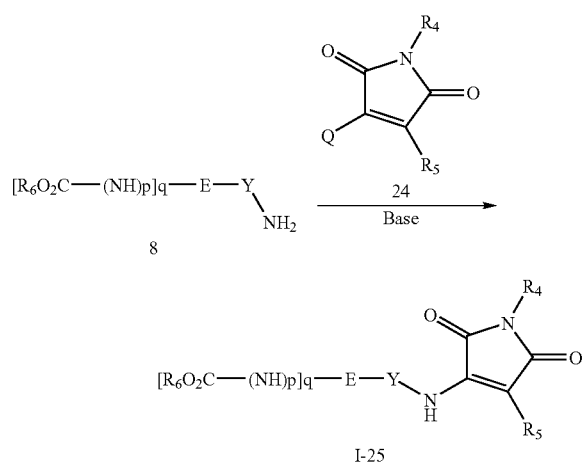

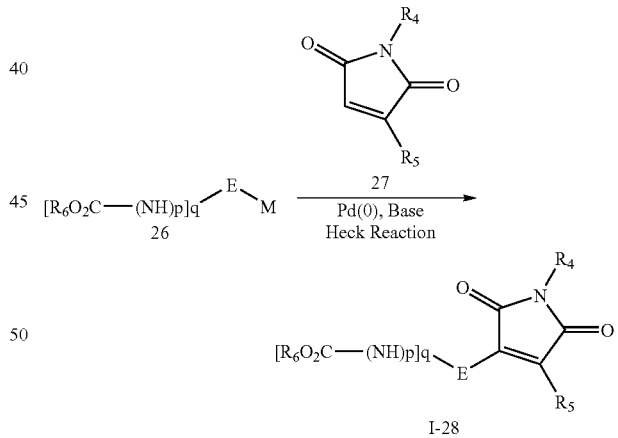

Compounds of Formula I wherein Q is Q-8 and Y is alkylene are prepared as shown in Scheme 5, according to methods reported by M. Tremblay et al, *Journal of Combinatorial Chemistry* (2002) 4:429. Reaction of polymer-bound activated ester 29 (polymer linkage is oxime activated-ester) with chlorosulfonylisocyante and t-butanol affords N-BOC sulfonylurea 30. Subjection of 30 to the Mitsunobu reaction with $R_4OH$ gives rise to 31. BOC-group removal with acid, preferably trifluoroacetic acid, and then treatment with base, preferably triethylamine, provides the desired sulfahydantoin I-32. Optionally, intermediate 30 is treated with acid, preferably trifluoroacetic acid, to afford the N-unsubstituted sulfahydantoin I-33.

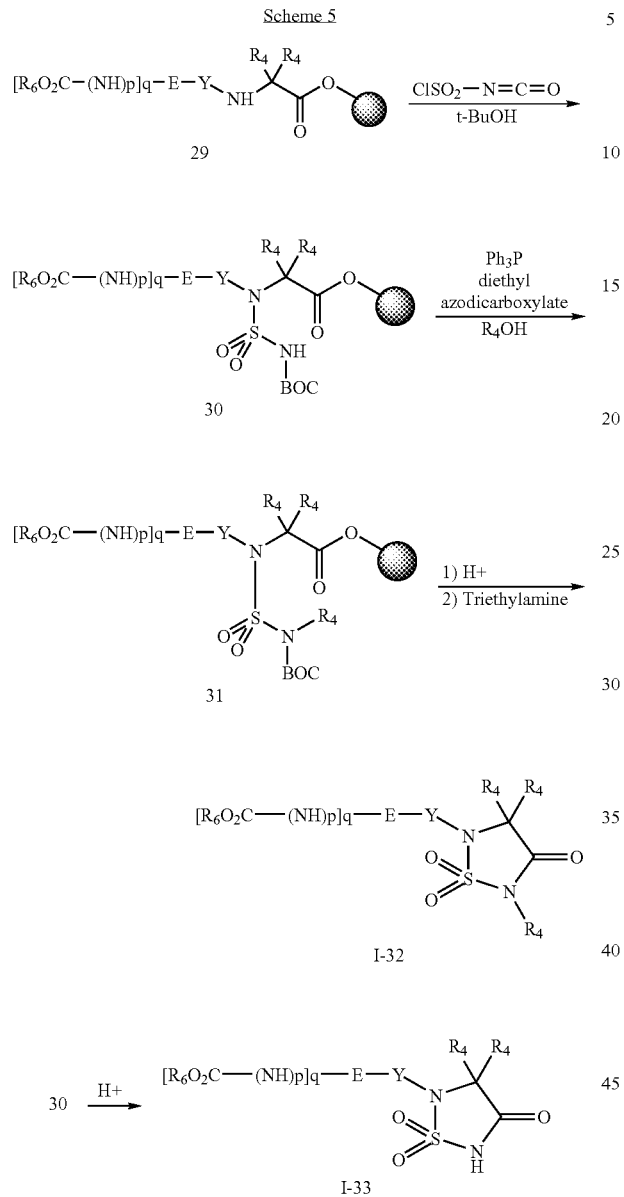

Compounds of Formula I wherein Q is Q-8 and Y is alkylene are also prepared as shown in Scheme 5.1. Amine 8 is condensed with the glyoxal hemiester to yield 31a. Reaction of chlorosulphonyl isocyanate first with benzyl alcohol then 31a yields 31b, which after heating yields I-32.

Compounds of Formula I wherein Q is taken from Q-8', are prepared according to the synthetic route shown in Scheme 5.2. Formation of 31c by the method of Muller and DuBois JOC 1989, 54, 4471 and its deprotonation with NaH/DMF or NaH/DMF and subsequently alkylation wherein M is a suitable leaving group such as chloride, bromide or iodide yields I-32'. Alternatively, I-32' is also available as shown in Scheme 5.3. Mitsunobu reaction of boc-sulfamide amino ethyl ester with alcohol 8b (made by methods analogous to that for amine 8) yields 31c, which after Boc removal with 2N HCl in dioxane is cyclized by the action of NaH on 31d results in I-32'.

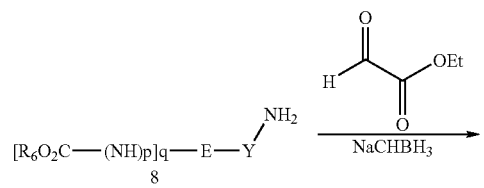

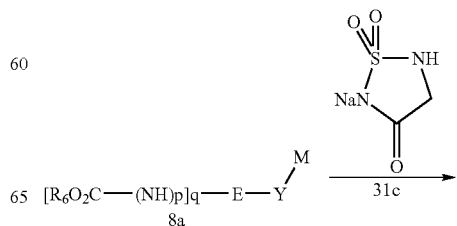

-continued

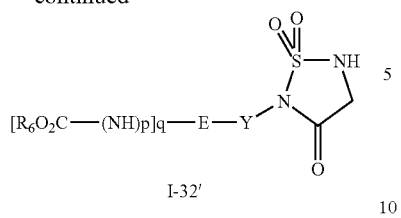

I-32'

Scheme 5.3

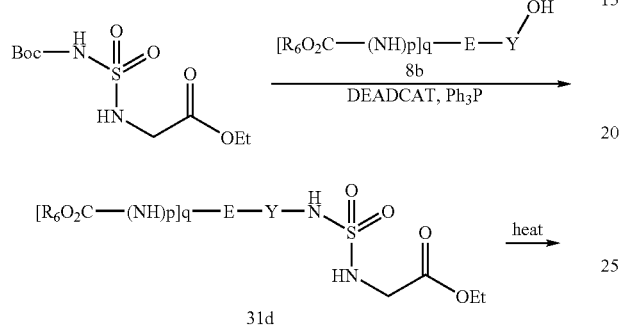

31d

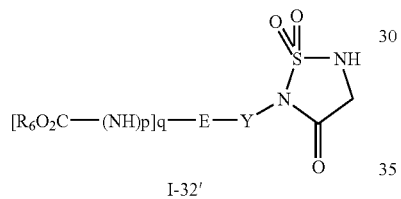

I-32'

Compounds of Formula I wherein Q is Q-9 and Y is alkylene are prepared as shown in Scheme 6. Reaction of polymer-bound amino acid ester 34 with an isocyanate affords intermediate urea 35. Treatment of 35 with base, preferably pyridine or triethylamine, with optional heating, gives rise to compounds of Formula I-36.

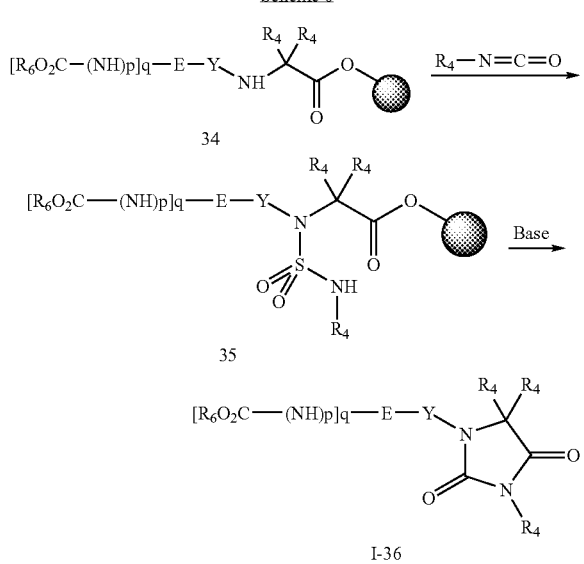

Compounds of Formula I wherein Q is Q-9 and Y is alkylene are also prepared as shown in Scheme 6.1. Reaction of aldehyde 8c (available by methods similar to that shown for 8a by anyone skilled in the art) with the t-butyl ester of glycine under reductive amination conditions yields 35a. Isocyanate 2a is condensed with p-nitrophenol (or the corresponding $R_4NH_2$ amine is condensed with p-nitrophenyl chloroformate) to yield the carbamic acid p-nitrophenyl ester, which when reacted with deprotonated 35a and yields the urea that when deprotected with acid yields 35b. Formula I-36 is directly available from 35b by the action of NaH and heat.

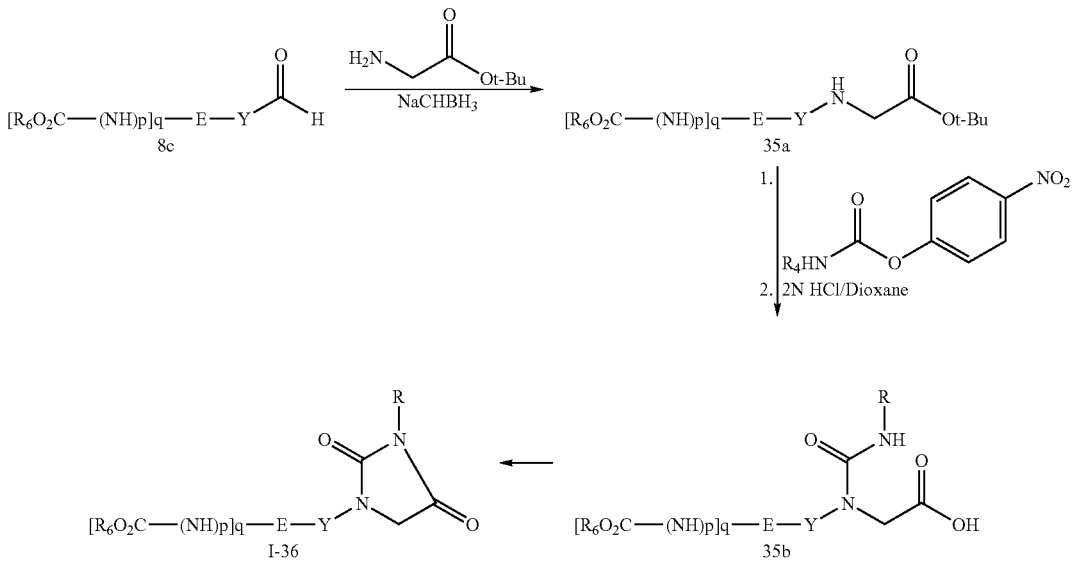

Compounds of Formula I wherein Q is taken from Q-9', are prepared according to the synthetic route shown in Scheme 6.2. Formation of 35c by the method described in JP10007804A2 and Zvilichovsky and Zucker, Israel Journal of Chemistry, 1969, 7(4), 547-54 and its deprotonation with NaH/DMF or NaH/DMF and its subsequent displacement of M, wherein M is a suitable leaving group such as chloride, bromide or iodide, yields I-36'.

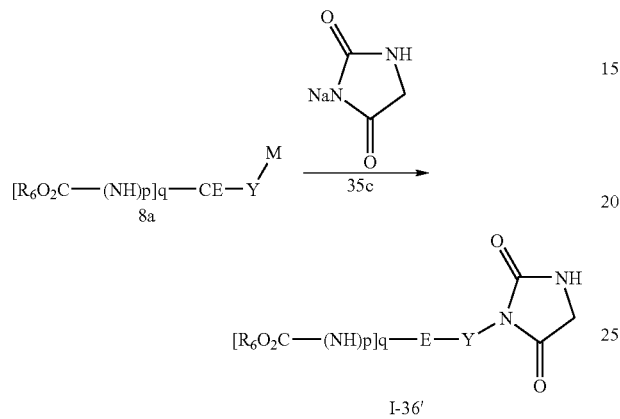

Compounds of Formula I-39 wherein Q is Q-10 or Q-11, and Y is alkylene are prepared as shown in Schemes 7.1 and 7.2, respectively. Treatment of alcohol 37 (Z=O) or amine 37 (Z=NH) with chlorosulfonylisocyanate affords intermediate carbamate or urea of structure 38. Treatment of 38 with an amine of structure $HN(R_4)R_4$ and base, preferably triethylamine or pyridine, gives sulfonylureas of Formula I-39. Reaction of chlorosulonylisocyanate with an alcohol (Z=O) or amine (Z=NR$_4$) 40 affords intermediate 41. Treatment of 41 with an amine 8 and base, preferably triethylamine or pyridine, gives sulfonylureas of Formula I-42.

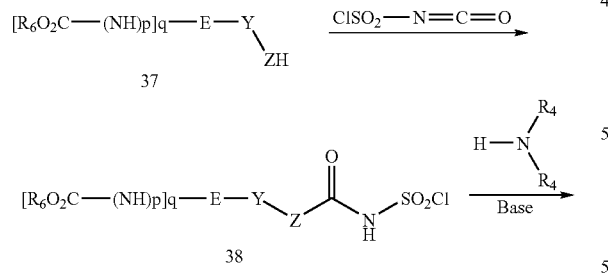

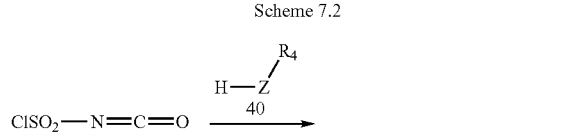

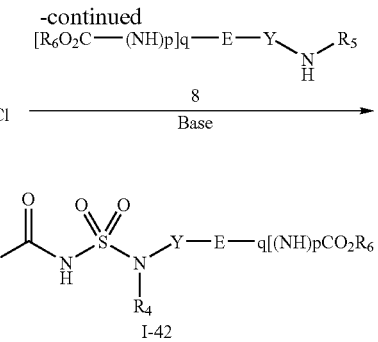

Compounds of Formula I wherein Q is taken from Q-12 are prepared according to the synthetic route shown in Scheme 8. Readily available pyridine 43, wherein TIPS is tri-iso-propylsilyl, is alkylated under standard conditions ($K_2CO_3$, DMF, $R_4$—I or Mitsunobu conditions employing $R_4$—OH) to give pyridine derivative 44 which is reacted with compound 12, wherein M is a suitable leaving group, to afford pyridones of formula I-45.

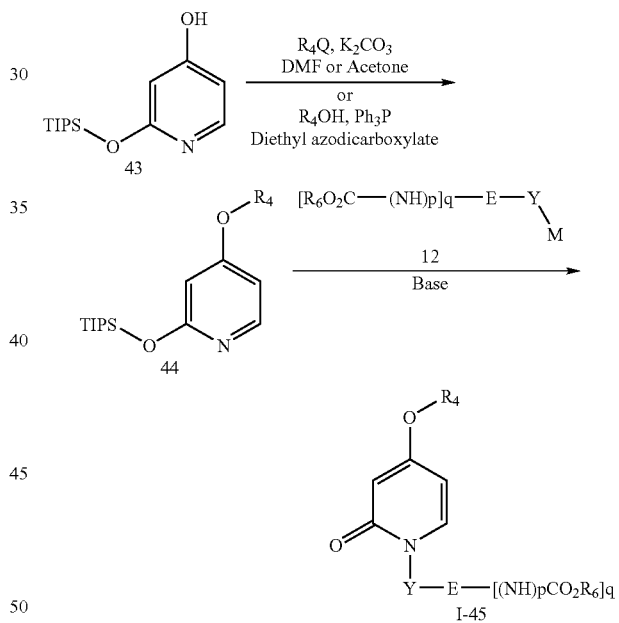

Compounds of Formula I wherein Q is taken from Q-13 are prepared according to the synthetic route shown in Scheme 9. Readily available pyridine 46 is alkylated under standard conditions ($K_2CO_3$, DMF, $R_4$—I or Mitsunobu conditions employing $R_4$—OH) to give pyridine derivative 47. N-alkylation with $K_2CO_3$, DMF, $R_4$—I affords pyridones of formula 48. Intermediate 48 is partitioned to undergo a Heck reaction, giving I-49; a Buchwald amination reaction, giving I-51; or a Buchwald Cu(I) catalyzed O-arylation reaction, to give I-52. The Heck reaction product I-49 may be optionally hydrogenated to afford the saturated compound I-50. Wherein the phenyl ether $R_4$ is methyl, compounds of formula I-49, I-50, I-51, or I-52 are treated with boron tribromide or lithium chloride to afford compounds of Formula I-53, wherein $R_4$ is hydrogen.

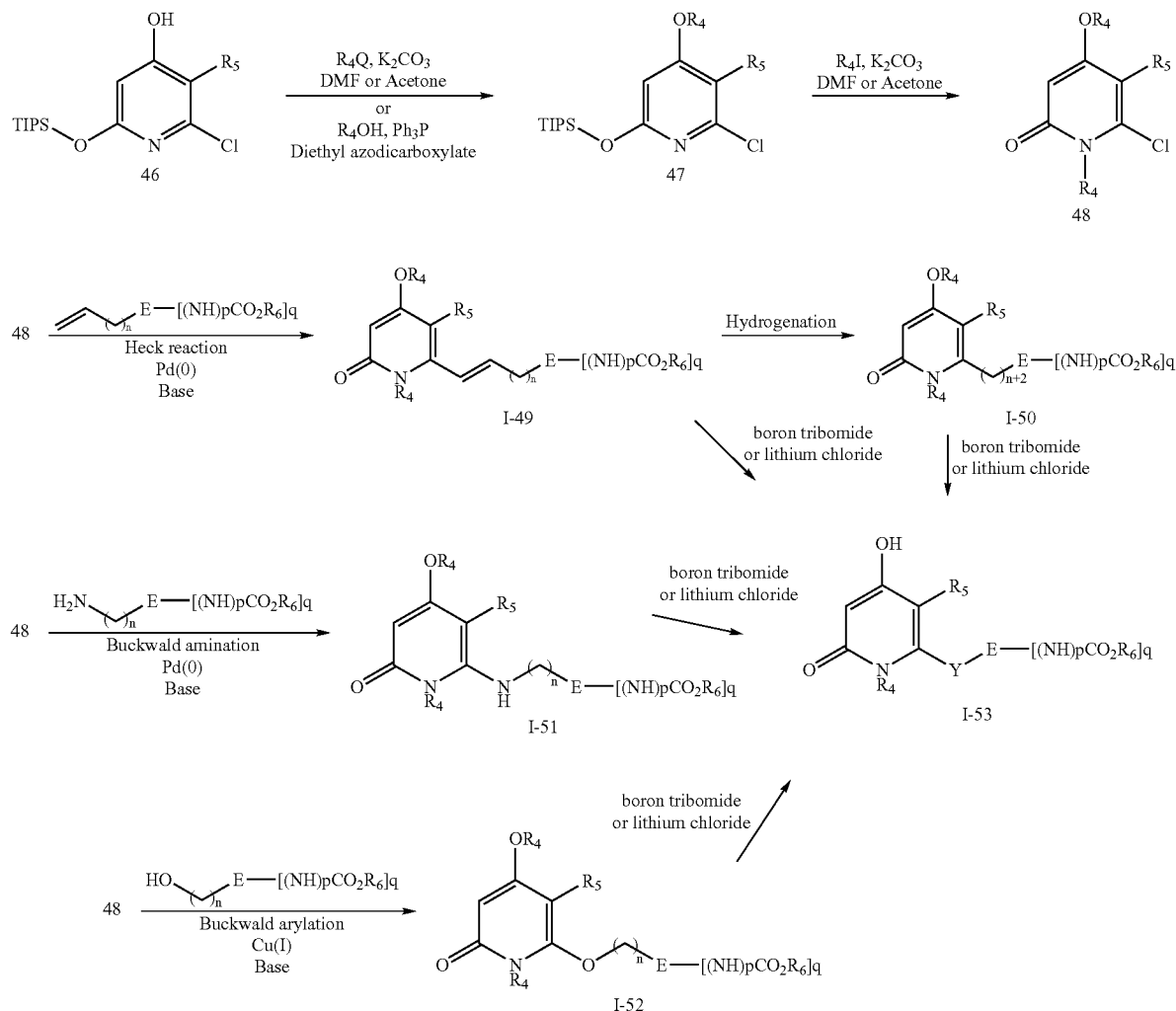

Scheme 9

Compounds of Formula I wherein Q is taken from Q-14 are prepared according to the synthetic route shown in Scheme 10. Starting from readily available pyridine 54 alkylation under standard conditions ($K_2CO_3$, DMF, $R_4$—I or Mitsunobu conditions employing $R_4$—OH) yields pyridine derivative 55. N-alkylation with $K_2CO_3$, DMF, $R_4$—I affords pyridones of formula 56. Intermediate 56, wherein M is a suitable leaving group, preferably bromine or chlorine, is partitioned to undergo a Heck reaction, giving I-57; a Buchwald amination reaction, giving I-59; or a Buchwald Cu(I) catalyzed O-arylation reaction, to give I-60. The Heck reaction product I-57 may be optionally hydrogenated to afford the saturated compound I-58. Wherein the phenyl ether $R_4$ is methyl, compounds of formula I-57, I-58, I-59, or I-60 are treated with boron tribromide or lithium chloride to afford compounds of Formula I-61, wherein $R_4$ is hydrogen.

Scheme 10

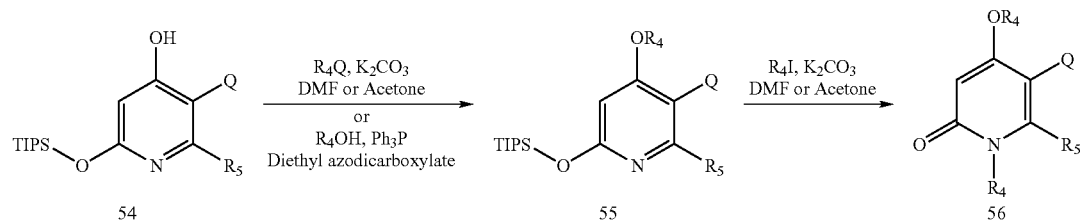

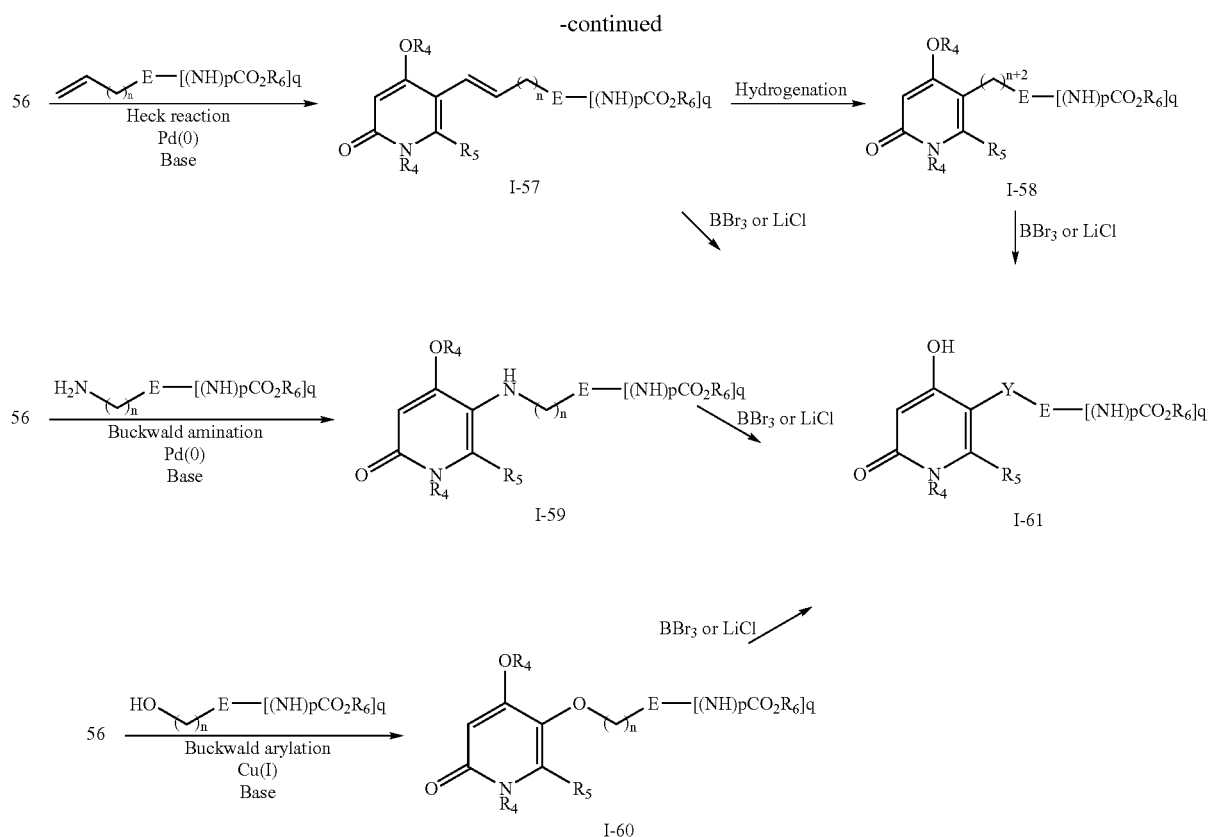

Compounds of Formula I wherein Q is taken from Q-15 are prepared according to the synthetic routes shown in Schemes 11 and 12. Starting esters 62 are available from the corresponding secoacids via TBS-ether and ester formation under standard conditions. Reaction of protected secoester 62 with Meerwin's salt produces the vinyl ether 63 as a pair of regioisomers. Alternatively, reaction of 62 with dimethylamine affords the vinylogous carbamate 64. Formation of the dihydropyrimidinedione 66 proceeds by condensation with urea 65 with azeotropic removal of dimethylamine or methanol. Dihydropyrimidinedione 66 may optionally be further substituted by Mitsunobu reaction with alcohols $R_4OH$ to give rise to compounds 67.

Scheme 12 illustrates the further synthetic elaboration of intermediates 67. Removal of the silyl protecting group (TBS) is accomplished by treatment of 67 with flouride (tetra-n-butylammonium fluoride or cesium fluoride) to give primary alcohols 68. Reaction of 68 with isocyanates 2 gives rise to compounds of Formula I-69. Alternatively, reaction of 68 with $[R_6O_2C(NH)p]q$-E—M, wherein M is a suitable leaving group, affords compounds of Formula I-70. Oxidation of 68 using the Dess-Martin periodinane (D. Dess, J. Martin, *J. Am. Chem. Soc.* (1991) 113:7277) or tetra-n-alkyl peruthenate (W. Griffith, S. Ley, *Aldrichimica Acta* (1990) 23:13) gives the aldehydes 71. Reductive amination of 71 with amines 8 gives rise to compounds of Formula I-72. Alternatively, aldehydes 71 may be reacted with ammonium acetate under reductive alkylation conditions to give rise to the primary amine 73. Reaction of 73 with isocyanates 2 affords compounds of Formula I-74.

Scheme 11

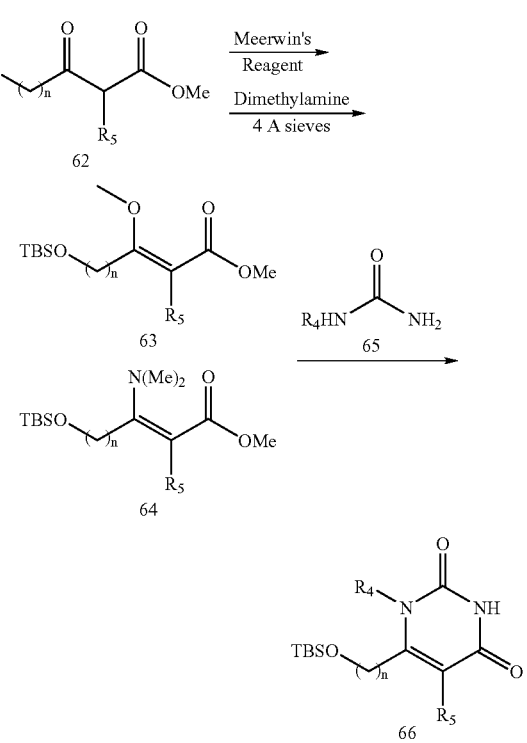

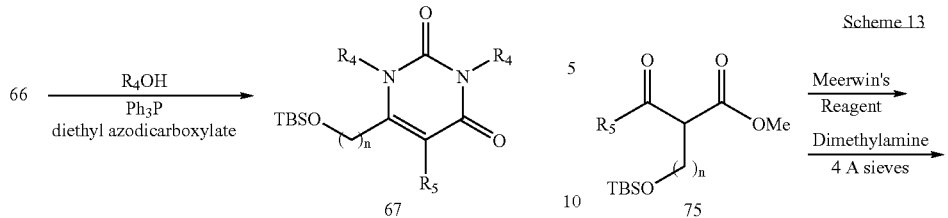

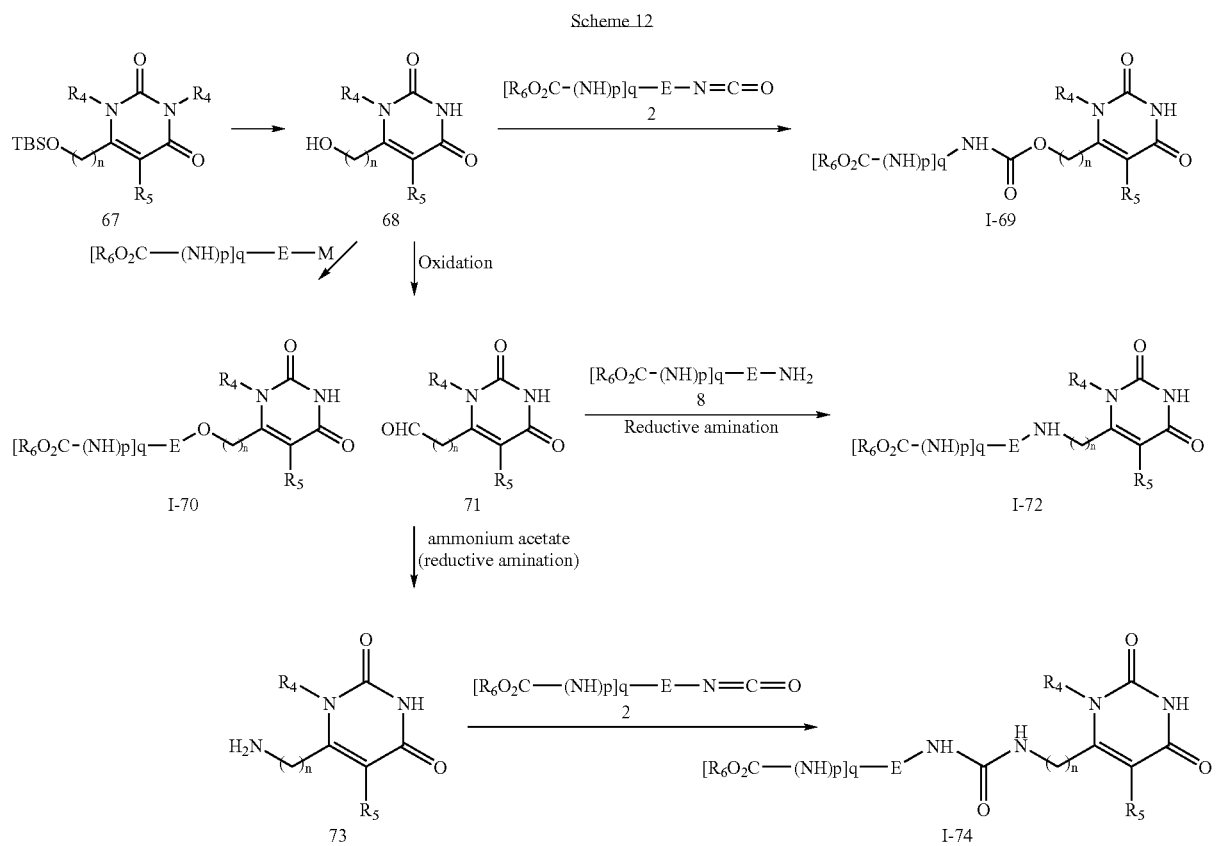

Compounds of Formula I wherein Q is taken from Q-16 are prepared according to the synthetic routes shown in Schemes 13 and 14. Starting esters 75 are available from the corresponding secoacids via TBS-ether and ester formation under standard conditions. Reaction of protected secoester 75-with Meerwin's salt produces the vinyl ether 76 as a pair of regioisomers. Alternatively, reaction of 75 with dimethylamine affords the vinylogous carbamate 77. Formation of the dihydropyrimidinedione 78 proceeds by condensation with urea 65 with azeotropic removal of dimethylamine or methanol. Dihydropyrimidinedione 78 may optionally be further substituted by Mitsunobu reaction with alcohols $R_4OH$ to give rise to compounds 79. Compounds of Formulae I-81, I-82, I-84, and I-86 are prepared as shown in Scheme 14 by analogy to the sequence previously described in Scheme 12.

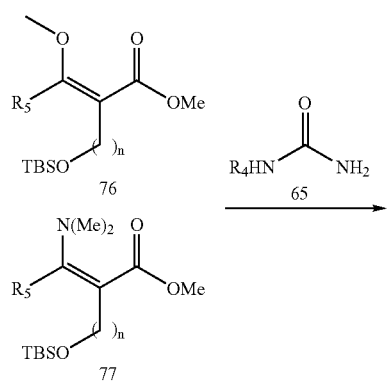

-continued

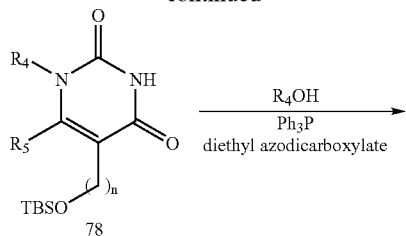

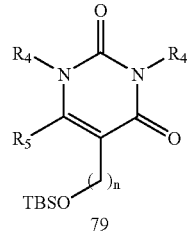

with formaldehyde and TBSCl (n=1) or M—(CH2)n-OTBS (n=2-4) to give rise to compounds 88.

Scheme 15

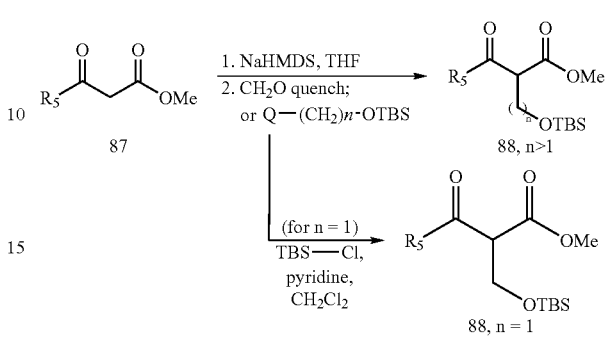

Compounds of Formula I wherein Q is taken from Q-17 are prepared according to the synthetic routes shown in Scheme 14

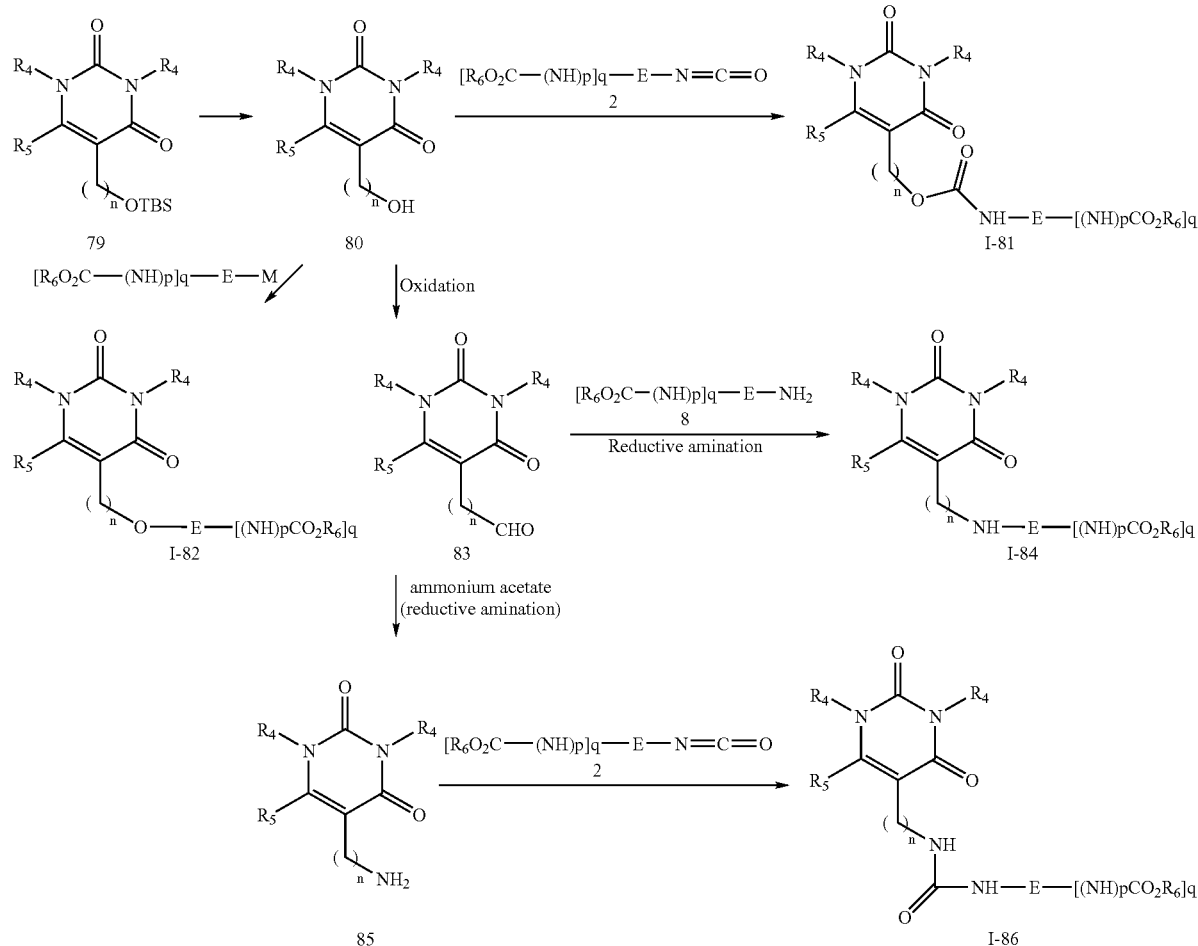

Alkyl acetoacetates 87 are commercially available and are directly converted into the esters 88 as shown in Scheme 15. Treatment of 87 with NaHMDS in THF, followed by quench Schemes 16.1 and 16.2, and starts with the BOC-protected hydrazine 13, which is converted to the 1,2-disubstituted hydrazine 89 by a reductive alkylation with a glyoxal derivative mediated by sodium cyanoborohydride and acidic workup. Condensation of 89 with diethyl malonate in benzene under reflux yields the heterocycle 90. Oxidation with N₂O₄ in benzene (see Cardillo, Merlini and Boeri *Gazz. Chim. Ital.* (1966) 9:8) to the nitromalonohydrazide 91 and further treatment with P₂O₅ in benzene (see: Cardillo, G. et al, *Gazz. Chim. Ital.* (1966) 9:973-985) yields the tricarbonyl 92. Alternatively, treatment of 90 with Brederick's reagent (t-BuOCH(N(Me₂)₂, gives rise to 93, which is subjected to ozonolysis, with a DMS and methanol workup, to afford the protected tricarbonyl 92. Compound 92 is readily deprotected by the action of CsF in THF to yield the primary alcohol 94. Alcohol 94 is optionally converted into the primary amine 95 by a sequence involving tosylate formation, azide displacement, and hydrogenation.

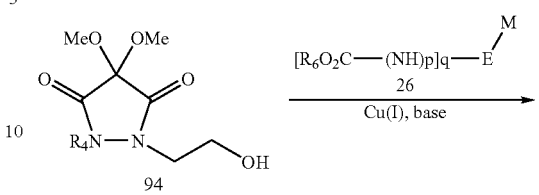

Scheme 16.2

Scheme 16.1

Reaction of 94 with (hetero)aryl halide 26, wherein M is iodo, bromo, or chloro, under copper(I) catalysis affords compounds I-96. Optional deprotection of the di-methyl ketal with aqueous acid gives rise to compounds of Formula I-98. By analogy, reaction of amine 95 with 26 under palladium(0) catalysis affords compounds of Formula I-97. Optional deprotection of the di-methyl ketal with aqueous acid gives rise to compounds of Formula I-99.

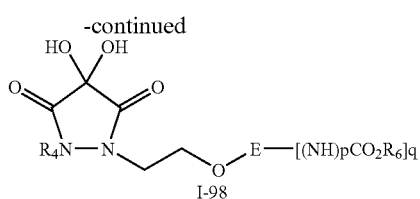

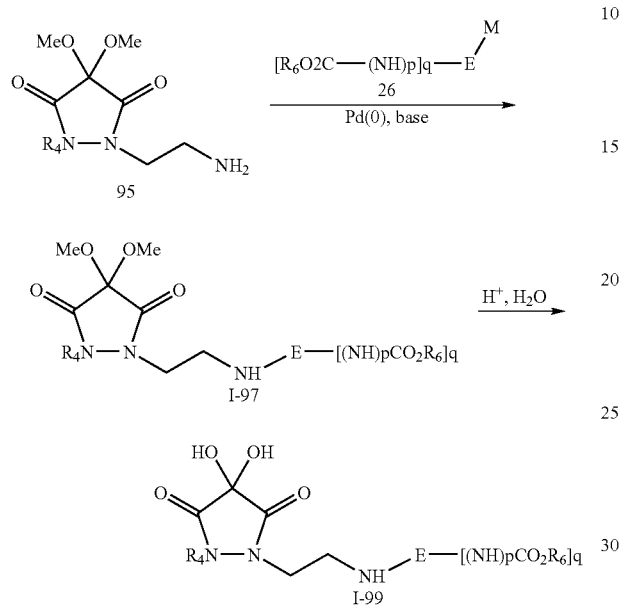

Compounds of Formula I wherein Q is taken from Q-17 are also prepared according to the synthetic route shown in Scheme 16.3. Deprotonation of 4,4-dimethyl-3,5-dioxopyrazolidine (95a, prepared according to the method described in Zinner and Boese, D. *Pharmazie* 1970, 25(5-6), 309-12 and Bausch, M. J. et.al *J. Org. Chem.* 1991, 56(19), 5643) with NaH/DMF or NaH/DMF and with NaH/DMF or NaH/DMF and its subsequent displacement of M, wherein M is a suitable leaving group such as chloride, bromide or iodide yields I-99a.

Scheme 16.3

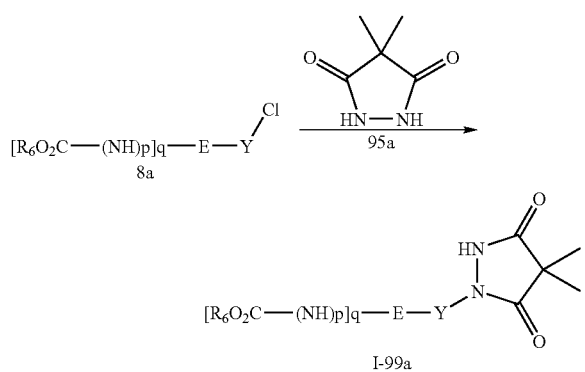

Compounds of Formula I wherein Q is taken from Q-18 are prepared as shown in Schemes 17.1 and 17.2. Aminoesters 100 are subjected to reductive alkylation conditions to give rise to intermediates 101. Condensation of amines 101 with carboxylic acids using an acid activating reagent such as dicyclohexylcarbodiimide (DCC)/hydroxybenzotriazole (HOBt) affords intermediate amides 102. Cyclization of amides 102 to tetramic acids 104 is mediated by Amberlyst A-26 hydroxide resin after trapping of the in situ generated alkoxide 103 and submitting 103 to an acetic acid-mediated resin-release.

Scheme 17.1

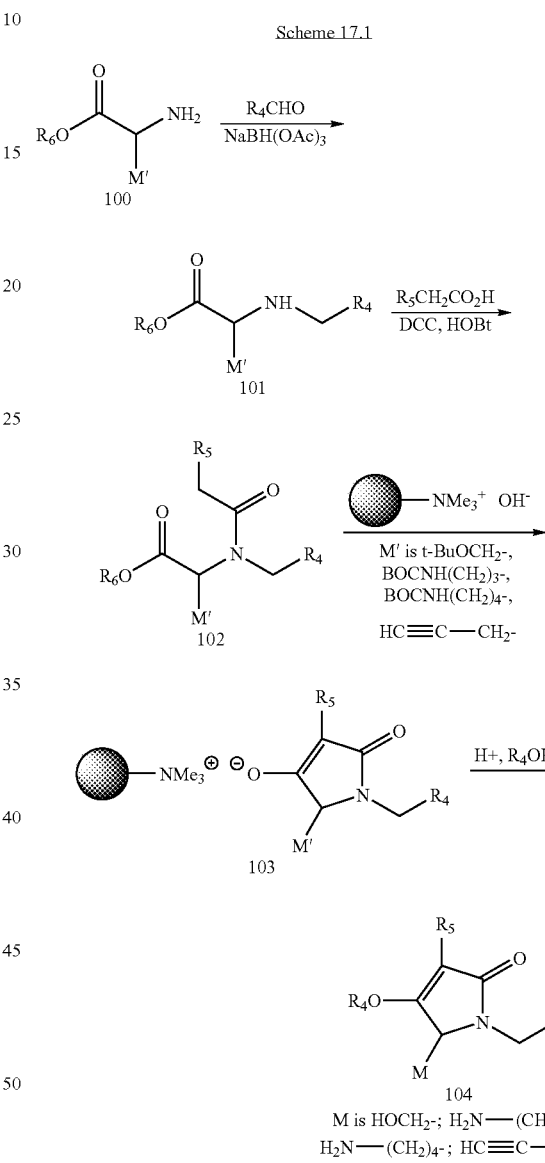

Scheme 17.2 illustrates the synthetic sequences for converting intermediates 104 to compounds of Formula I. Reaction of alcohol 104.1 with aryl or heteroaryl halide 26 (Q=halogen) under copper(I) catalysis gives rise to compounds of Formula I-105.1. Reaction of amines 104.2 and 104.3 with 26 under Buchwald palladium(0) catalyzed amination. conditions affords compounds of Formulae I-105.2 and I-105.3. Reaction of acetylene 104.4 with 26 under Sonogashira coupling conditions affords compounds of Formula I-105.4. Compounds I-105.4 may optionally be reduced to the corresponding saturated analogs I-105.5 by standard hydrogenation.

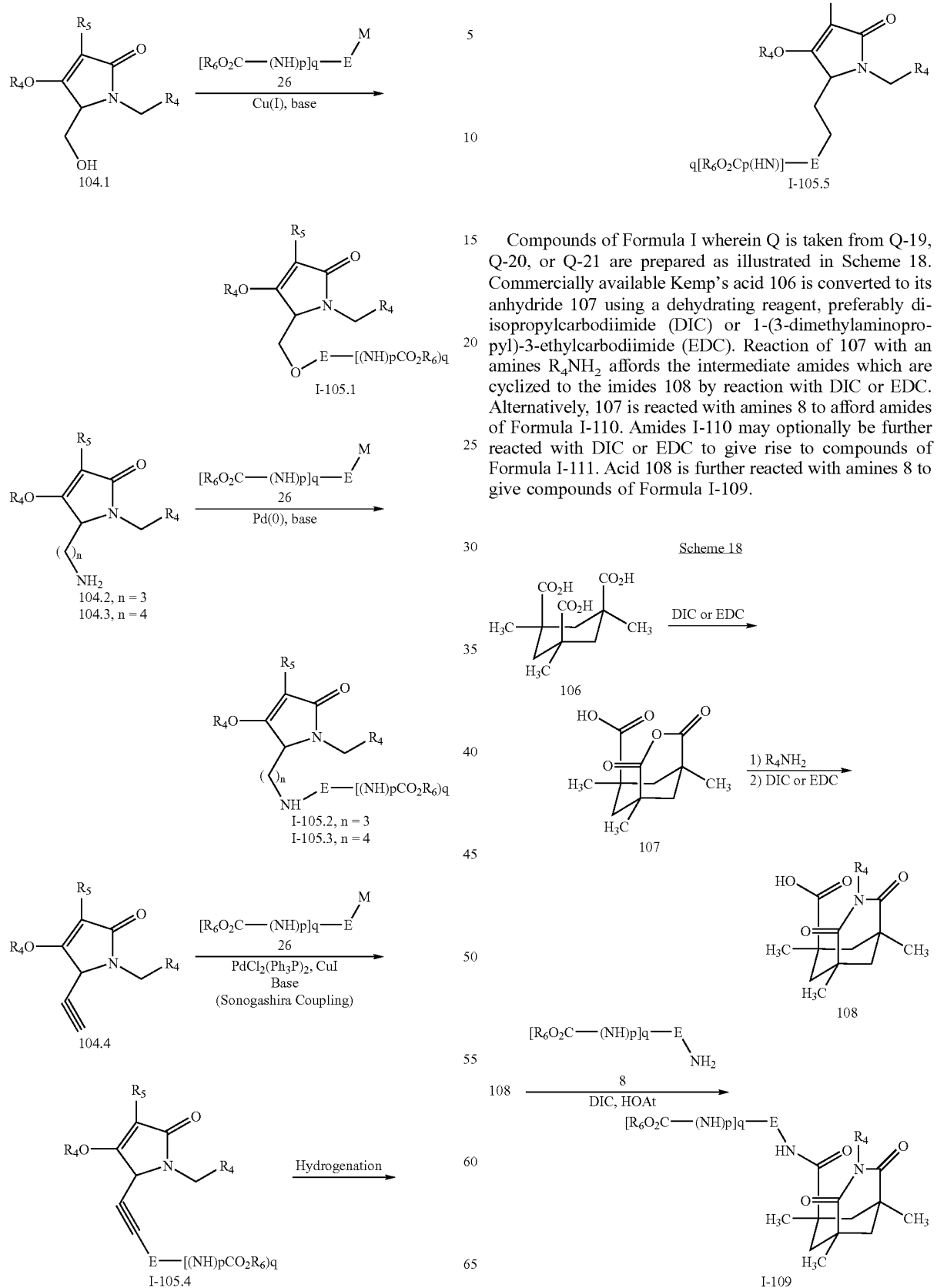

Compounds of Formula I wherein Q is taken from Q-19, Q-20, or Q-21 are prepared as illustrated in Scheme 18. Commercially available Kemp's acid 106 is converted to its anhydride 107 using a dehydrating reagent, preferably diisopropylcarbodiimide (DIC) or 1-(3-dimethylaminopropyl)-3-ethylcarbodiimide (EDC). Reaction of 107 with an amines $R_4NH_2$ affords the intermediate amides which are cyclized to the imides 108 by reaction with DIC or EDC. Alternatively, 107 is reacted with amines 8 to afford amides of Formula I-110. Amides I-110 may optionally be further reacted with DIC or EDC to give rise to compounds of Formula I-111. Acid 108 is further reacted with amines 8 to give compounds of Formula I-109.

-continued

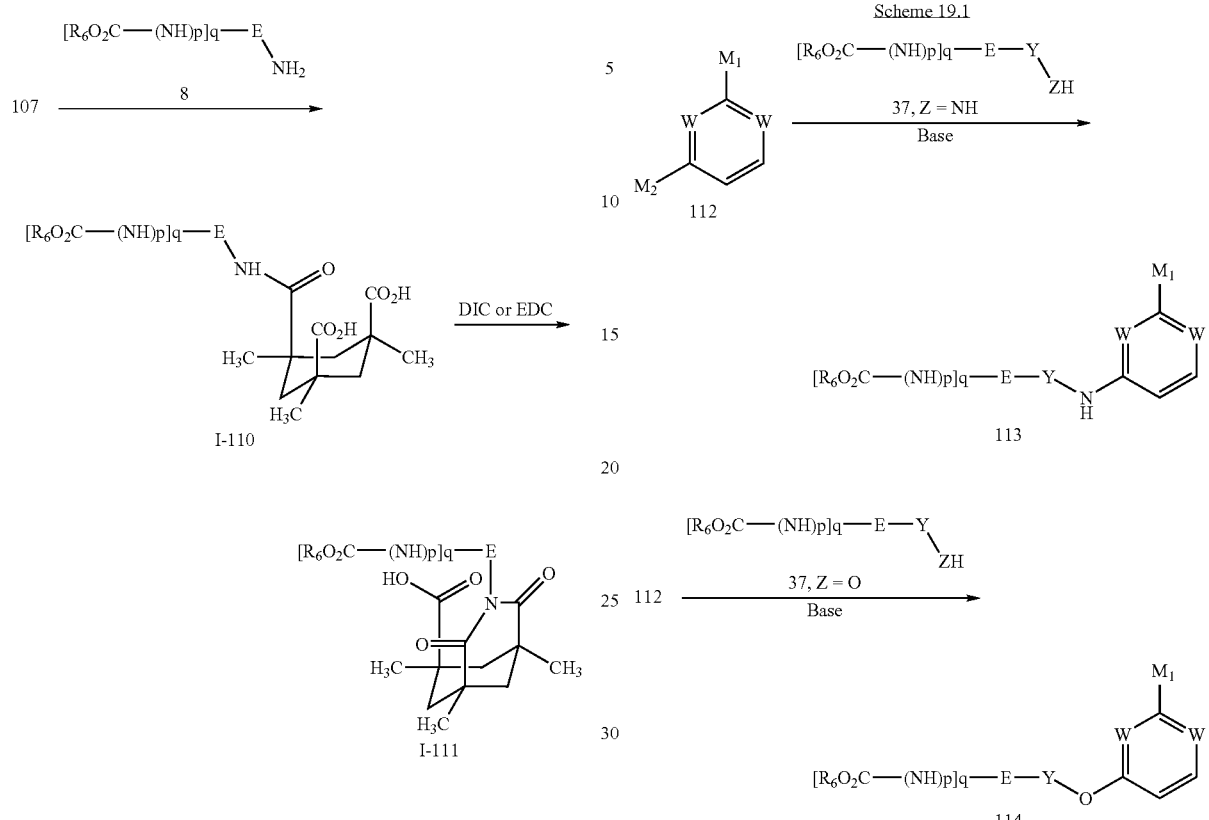

Compounds of Formula I wherein Q is taken from Q-22 or Q-23 are prepared as shown in Schemes 19.1 through 19.3. Preparation of intermediates 113 and 114 are prepared as shown in Scheme 19.1 from di-halo(hetero)aryls 112, wherein $M_2$ is a more robust leaving group than $M_1$. Reaction of 112 with amines 37 (Z=NH) either thermally in the presence of base or by palladium(0) catalysis in the presence of base and phosphine ligand affords compounds 113. Alternatively, reaction of 112 with alcohols 37 (X=O) either thermally in the presence of base or by copper(I) catalysis in the presence of base affords compounds 114.

Scheme 19.2 illustrates the conversion of intermediates 113 into compounds of Formula I-115, I-118, or 117. Treatment of 113 with aqueous copper oxide or an alkaline hydroxide affords compounds of Formula I-115. Alternatively, treatment of 113 with t-butylmercaptan under copper (I) catalysis in the presence of ethylene glycol and potassium carbonate gives rise to 116 (see F. Y. Kwong and S. L. Buchwald, *Organic Letters* (2002) 4:3517. Treatment of the t-butyl sulfide 116 with acid affords the desired thiols of Formula I-118. Alternatively, 113 may be treated with excess ammonia under pressurized conditions to afford compound 117.

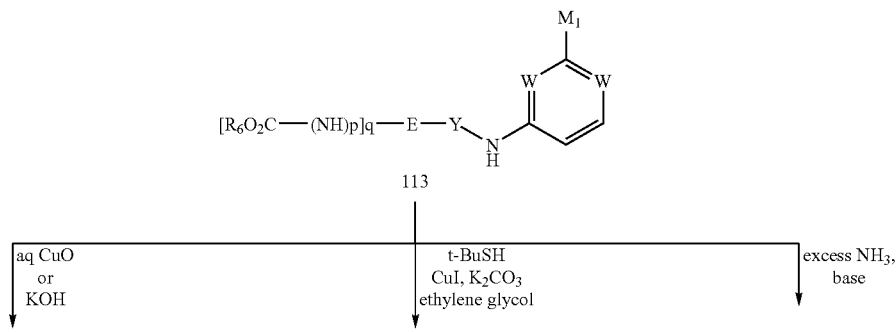

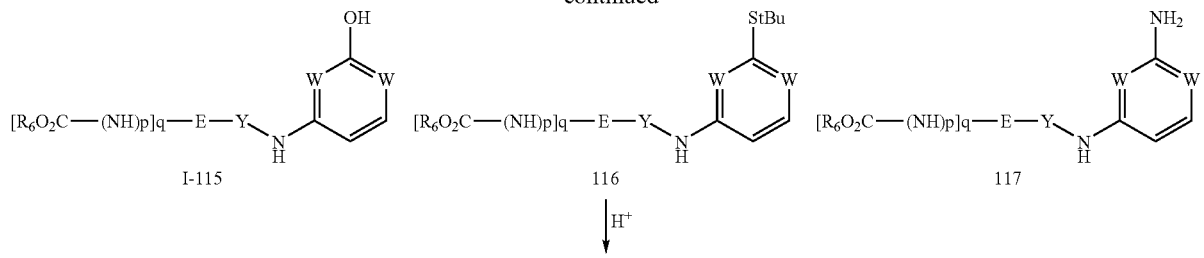
Scheme 19.3 illustrates the conversion of intermediate 114 into compounds of Formula I-119, I-122, and 121, by analogy to the sequence described in Scheme 19.2.
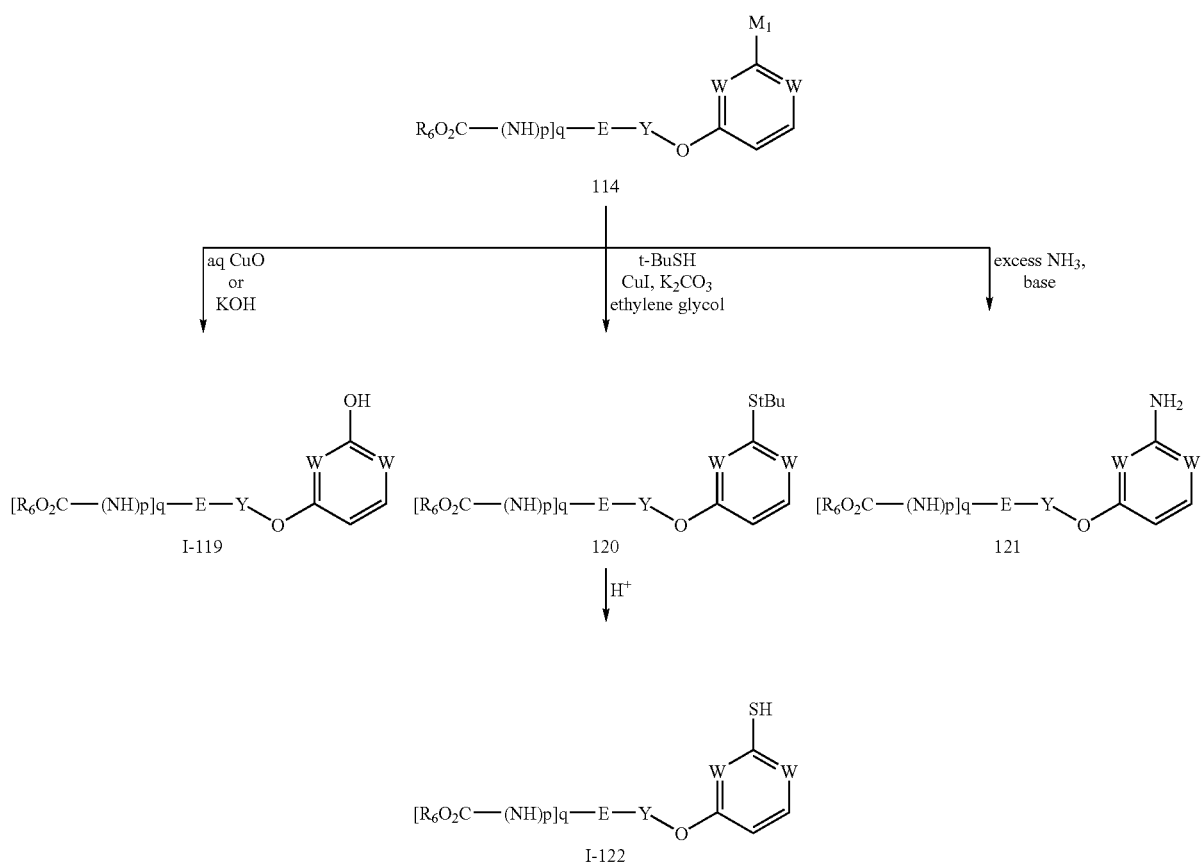

Compounds of Formula I wherein Q is taken from Q-24, Q-25, or Q-26 are prepared as shown in Scheme 20. Reaction of compounds I-115 or I-119 with chlorosulfonylisocyanate, followed by in situ reaction with amines $HN(R_4)_2$ gives rise to compounds of Formulae I-123 or I-124. Reaction of compounds I-118 or I-122 with a peracid, preferably peracetic acid or trifluoroperacetic acid, affords compounds of Formula I-125 or I-126. Reaction of compounds 117 or 121 with chlorosulfonylisocyanate, followed by in situ reaction with amines $HN(R_4)_2$ or alcohols $R_4OH$, affords compounds of Formulae I-127, I-128, I-129, or I-130.

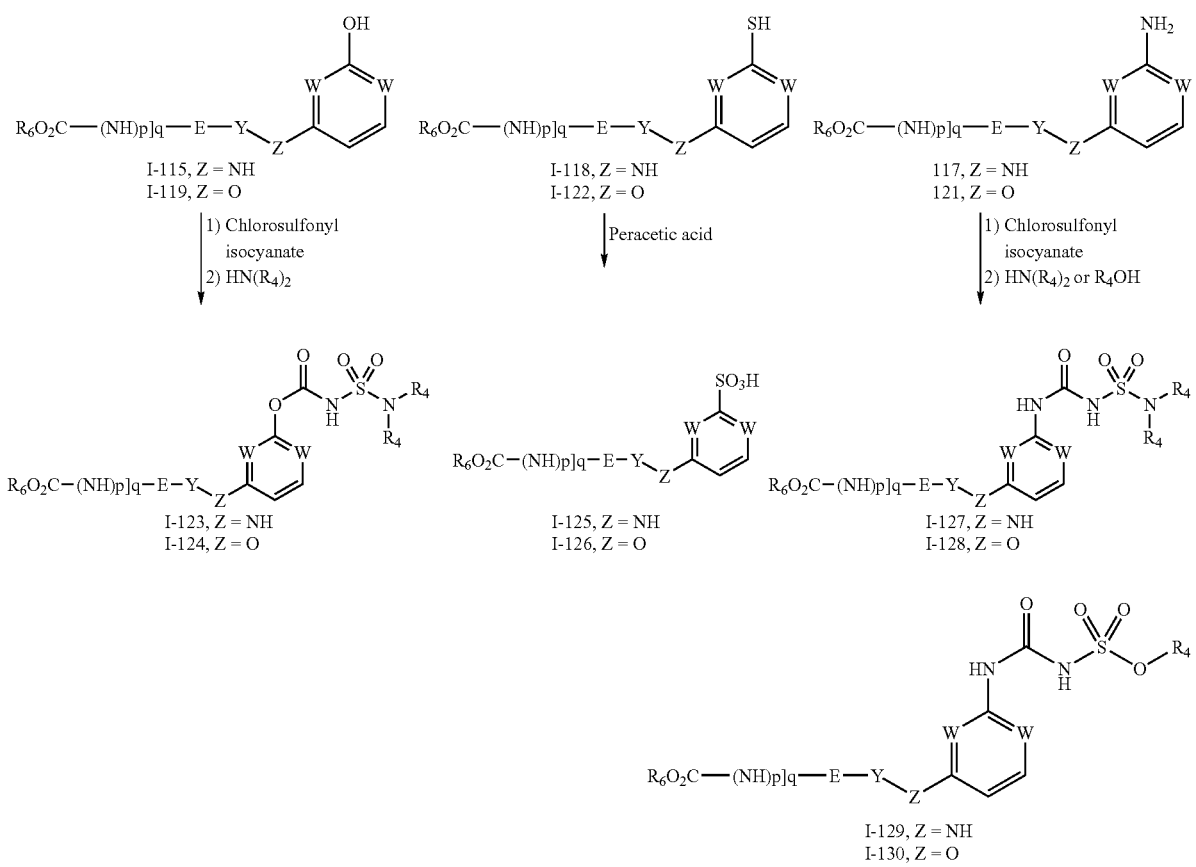

Compounds of Formula I wherein Q is taken from Q-27 are prepared as illustrated in Scheme 21. Reductive alkylation of thiomorpholine with aldehydes 131 affords benzylic amines 132, which are then subjected to peracid oxidation to give rise to the thiomorpholine sulfones 133 (see C. R. Johnson et al, *Tetrahedron* (1969) 25: 5649). Intermediates 133 are reacted with amines 8 ($Z=NH_2$) under Buchwald palladium-catalyzed amination conditions to give rise to compounds of Formula I-134. Alternatively, compounds 133 are reacted with alcohols 8 (Z=OH) under Buchwald copper (I) catalyzed conditions to afford compounds of Formula I-135. Alternatively, intermediates 133 are reacted with alkenes under palladium(0)-catalyzed Heck reaction conditions to give compounds of Formula I-136. Compounds I-136 are optionally reduced to the corresponding saturated analogs I-137 by standard hydrogenation conditions or by the action of diimide.

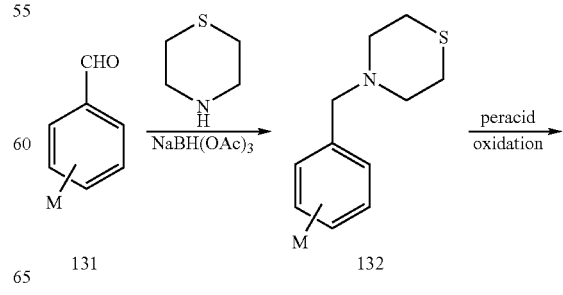

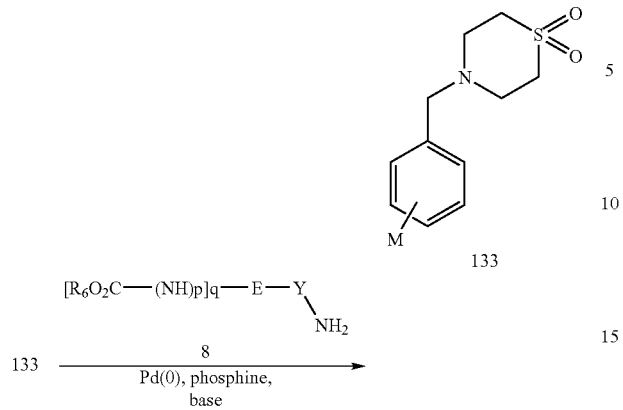

133

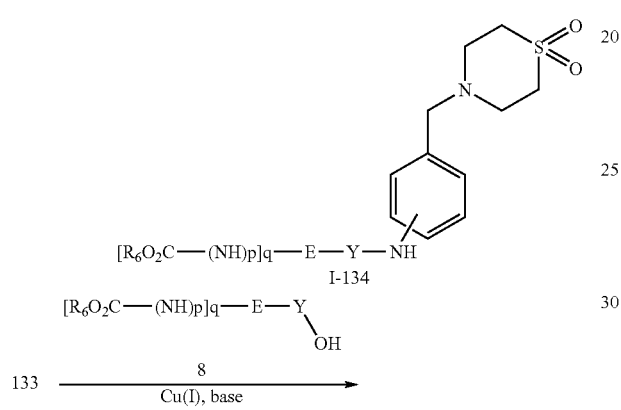

I-134

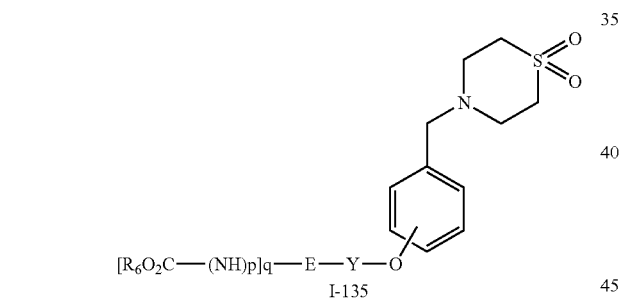

I-135

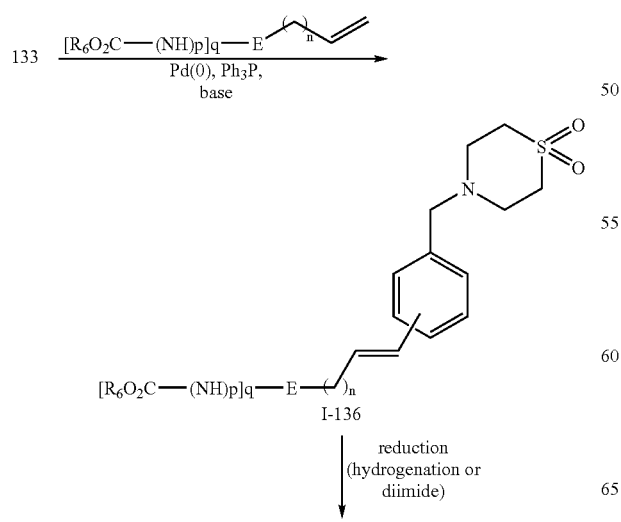

I-136 reduction
(hydrogenation or diimide)

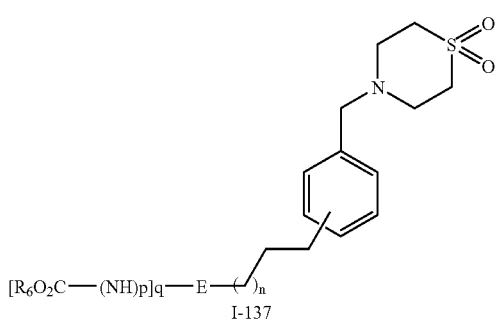

I-137

Compounds of Formula I wherein Q is taken from Q-27 are also prepared as illustrated in Scheme 21.1. Aldehyde 8c is reductively aminated with ammonia, and the resultant amine condensed with divinyl sulphone to yield I-134. Intermediate 134a is also available by reduction of amide 8d under a variety of standard conditions.

Scheme 21.1

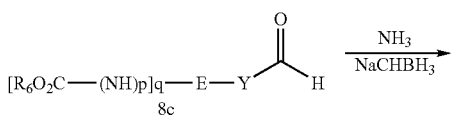

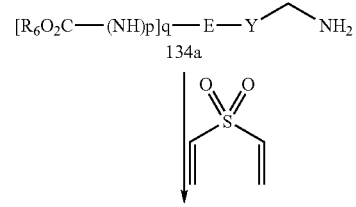

Amide reduction
i.e. LAH

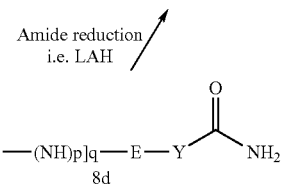

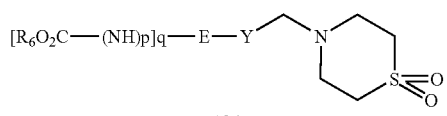

More generally, amines 134c are available via the reduction of amides 134b as shown in Scheme 21.2 The morpholine amide analogues 134d and morpholine analogues 134e are also available as shown in Scheme 21.2

Scheme 21.2

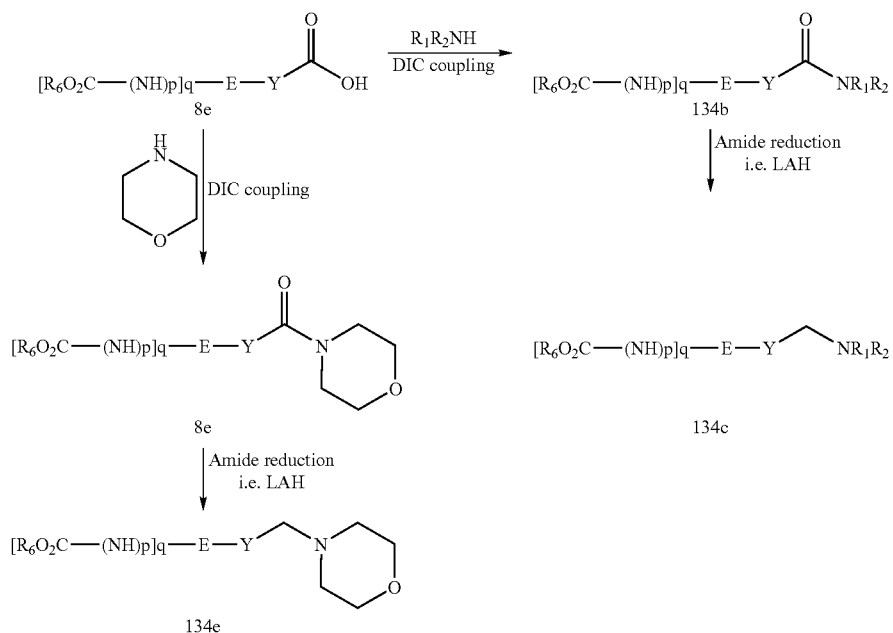

Compounds of Formula I wherein Q is taken from Q-28 or Q-29 are prepared according to the sequences illustrated in Scheme 22. Readily available amides 138 are reacted with chlorosulfonylisocyanate to give intermediates 140, which are reacted in situ with amines HN(R$_4$)$_2$ or alcohols R$_4$OH to afford compounds of Formulae I-141 or I-142, respectively. Alternatively, amides 138 are reacted with sulfonyl chlorides to give compounds of Formula I-139.

Scheme 22

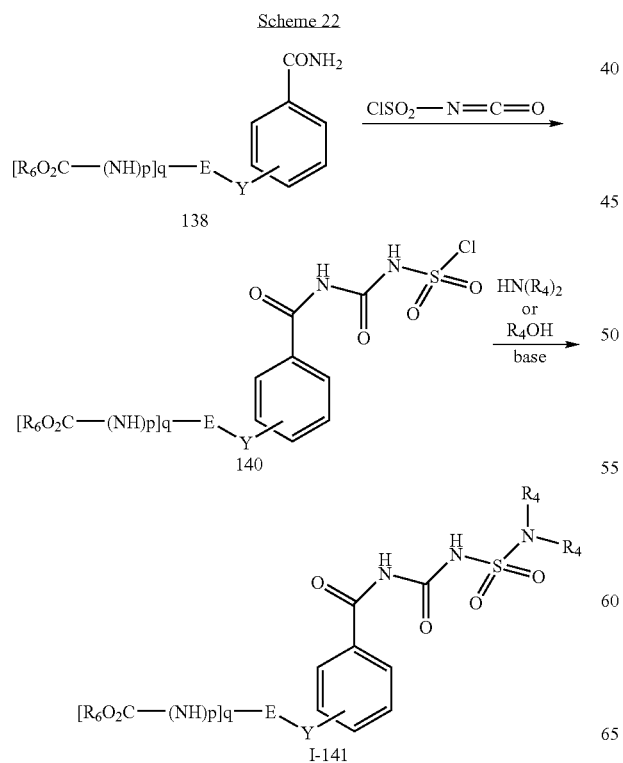

-continued

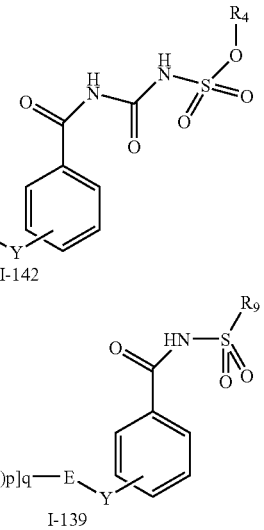

Compounds of Formula I wherein Q is taken from Q-30 are prepared as shown in Scheme 23. Readily available N-BOC anhydride 143 (see S. Chen et al, *J. Am. Chem. Soc.* (1996) 118:2567) is reacted with amines HN(R$_4$)$_2$ or alcohols R$_6$OH to afford acids 144 or 145, respectively. Intermediates 144 or 145 are further reacted with amines HN(R$_4$)$_2$ in the presence of an acid-activating reagent, preferably PyBOP and di-isopropylethylamine, to give diamides 146 or ester-amides 147. Intermediate 145 is converted to the diesters 148 by reaction with an alkyl iodide in the presence of base, preferably potassium carbonate. Intermediates 146-148 are treated with HCl/dioxane to give the secondary amines 149-151, which are then condensed with acids 152 in the presence of PyBOP and di-isopropylethylamine to give compounds of Formula I-153.

Scheme 23

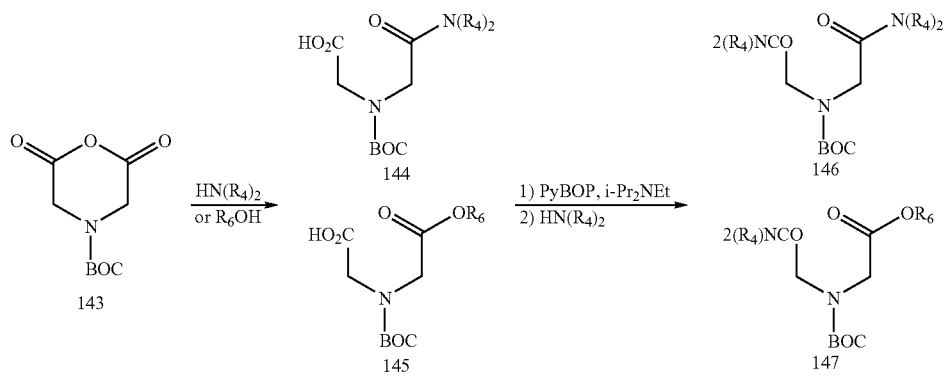

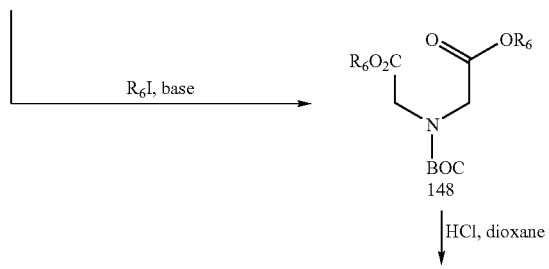

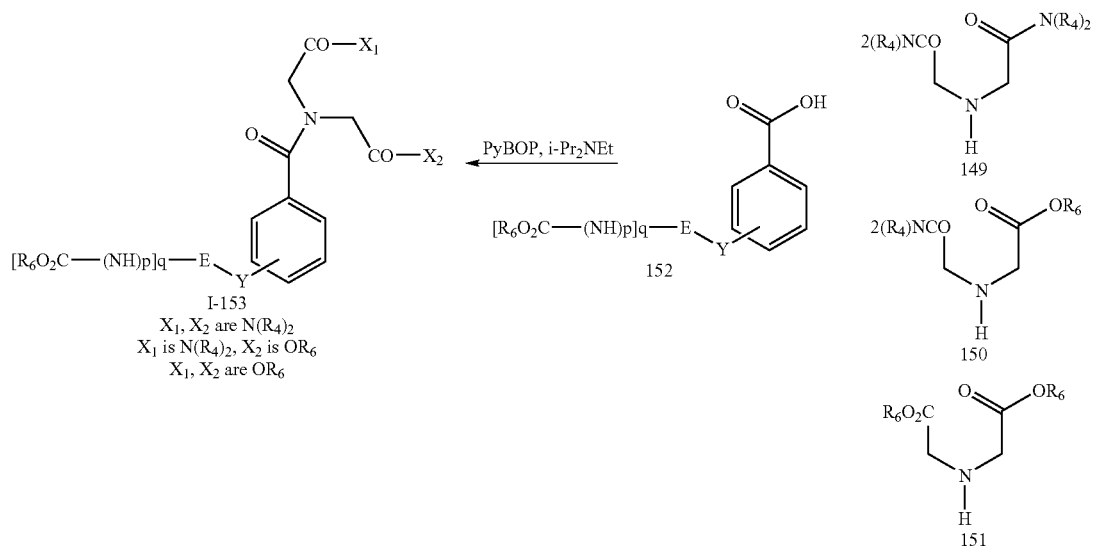

Compounds of Formula I wherein Q is taken from Q-31 or Q-32 are prepared according to the sequences illustrated in Scheme 24. Treatment of readily available sulfenamides 154 with amines 37 (Z=NH), alcohols 37 (Z=O), or alkenes 37 (Z=—CH=CH$_2$), gives rise to compounds of Formula I-155. Treatment of sulfenamides I-155 with iodosobenzene in the presence of alcohols R$_6$OH gives rise to the sulfonimidates of Formula I-157 (see D. Leca et al, Organic Letters (2002) 4:4093). Alternatively, compounds I-155 (Z=—CH=CH) may be optionally reduced to the saturated analogs I-156 (Z=CH$_2$—CH$_2$—), which are converted to the corresponding sulfonimidates I-157.

Treatment of readily available sulfonylchlorides 154.1 with amines HN(R$_4$)$_2$ and base gives rise to compounds of Formula I-154.2.

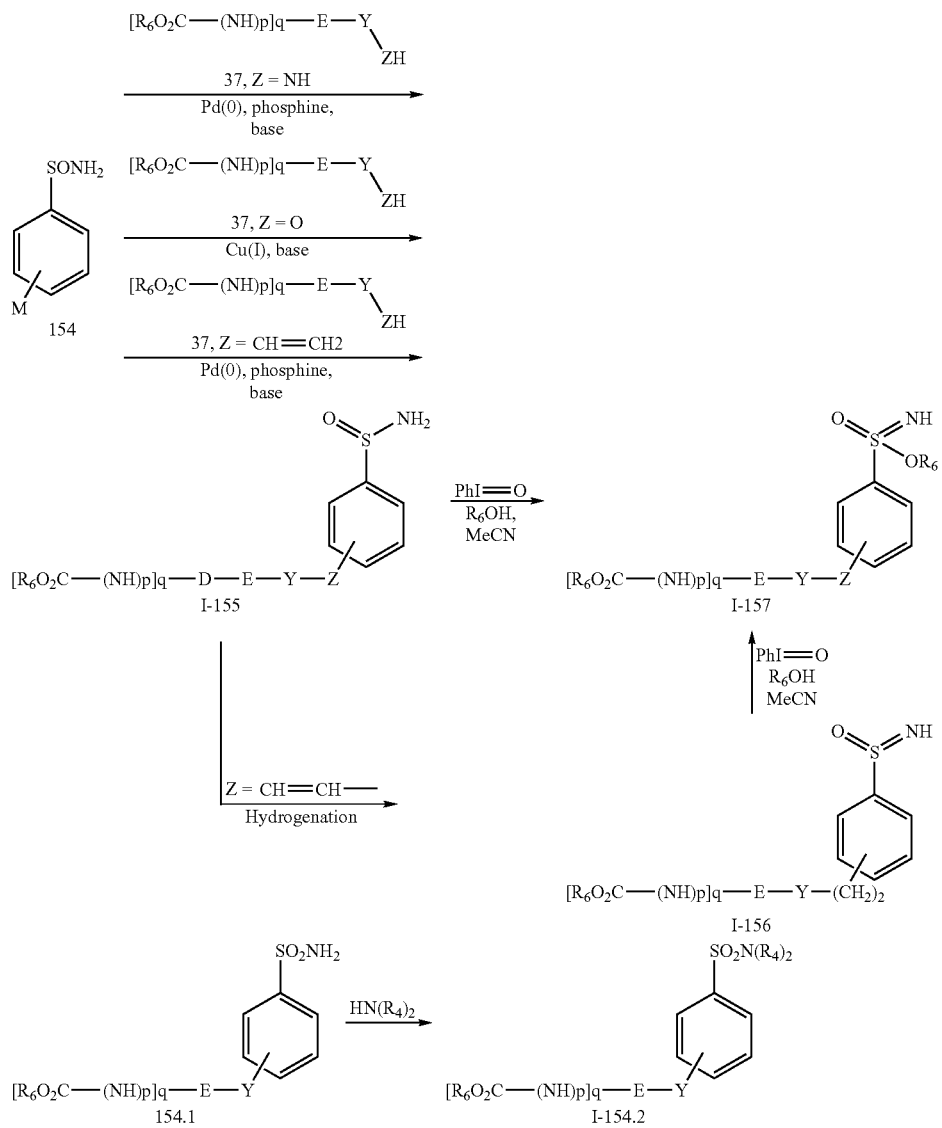

Compounds of Formula I wherein Q is taken from Q-33 are prepared as shown in Scheme 25. Readily available nitriles 158 are reacted with amines 37 (Z=NH), alcohols 37 (Z=O), or alkenes 37 (Z=—CH=CH$_2$) to afford compounds of Formula I-159. Compounds I-159 (wherein Z=CH=CH—) are optionally reduced to their saturated analogs I-160 by standard catalytic hydrogenation conditions. Treatment of compounds I-159 or I-160 with a metal azide (preferably sodium azide or zinc azide) gives rise to tetrazoles of Formula I-161.

Scheme 25

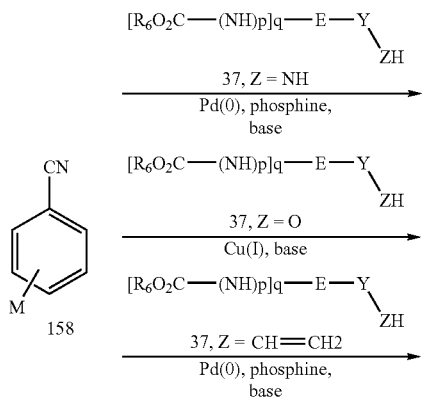

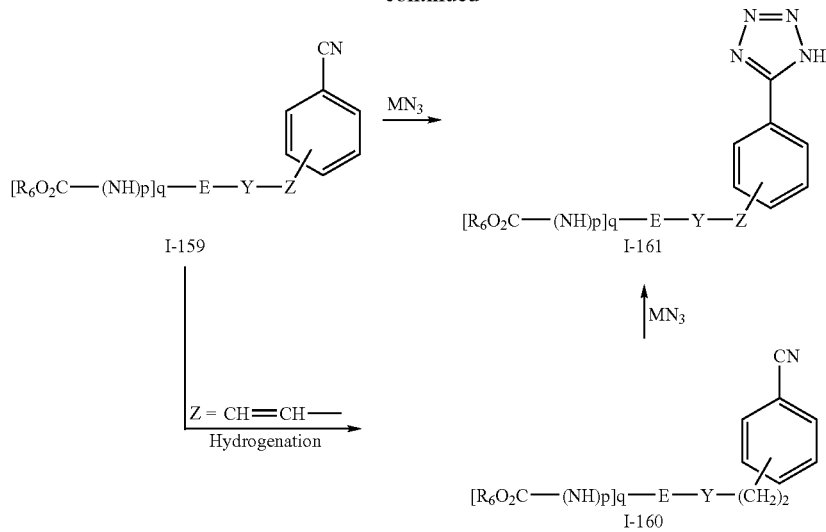

Compounds of Formula I wherein Q is taken from Q-34 are prepared as shown in Scheme 26. Readily available esters 162 are reacted with amines 37 (Z=NH), alcohols 37 (Z=O), or alkenes 37 (Z=—CH=CH$_2$) to afford compounds of Formula I-163. Compounds I-163 (wherein Z is —CH=CH—) are optionally converted to the saturated analogs I-164 by standard hydrogenation conditions. Compounds I-163 or I-164 are converted to the desired phosphonates I-165 by an Arbuzov reaction sequence involving reduction of the esters to benzylic alcohols, conversion of the alcohols to the benzylic bromides, and treatment of the bromides with a tri-alkylphosphite. Optionally, phosphonates I-165 are converted to the fluorinated analogs I-166 by treatment with diethylaminosulfur trifluoride (DAST).

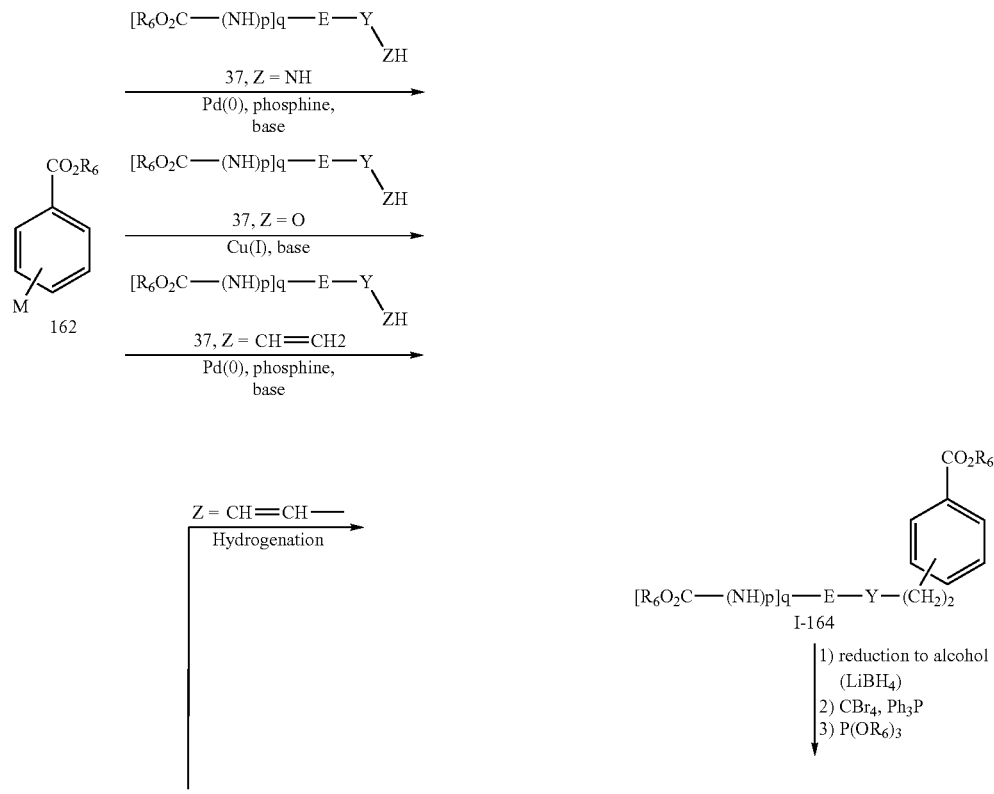

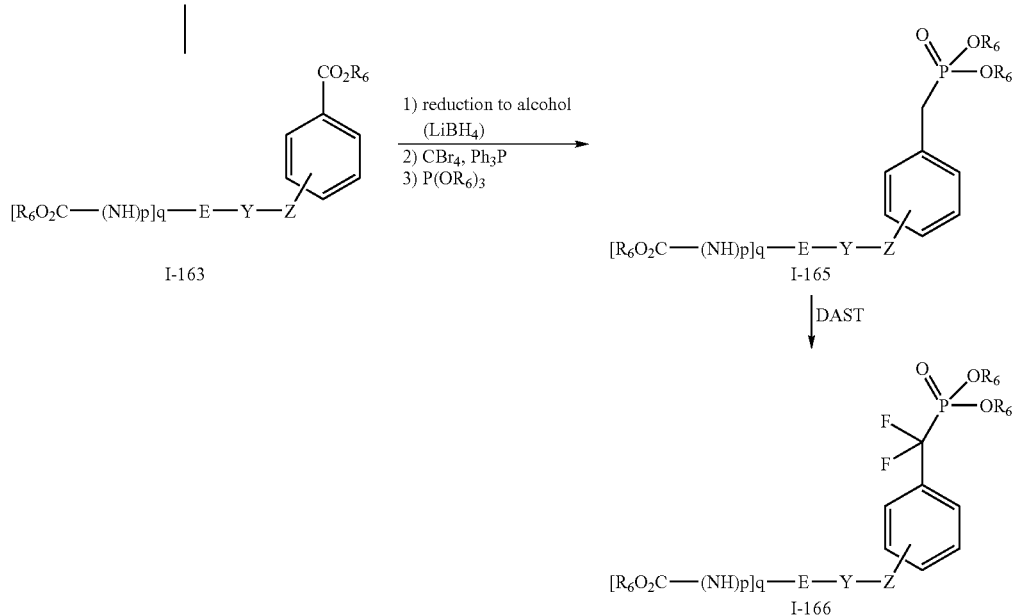

Compounds of Formula I wherein Q is taken from Q-34 are also prepared as illustrated in Scheme 26.1. Intermediate 8a, wherein M is a suitable leaving group such as chloride, bromide or iodide, is refluxed with triethyl phosphite and the resulting phosphoryl intermediate saponified under mild conditions to yield I-165.

Scheme 26

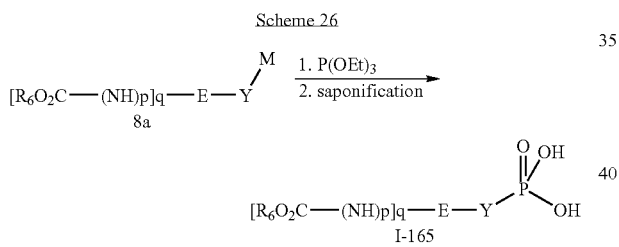

Compounds of Formula I wherein Q is taken from Q-35 are prepared according to Scheme 27. Readily available acid chlorides 167 are reacted with oxazolidones in the presence of base to afford the N-acyl oxazolidinones 168. Intermediate 168 are reacted with amines 37 (Z=NH), alcohols 37 (Z=O), or alkenes 37 (Z=—CH=CH$_2$) to afford the N-acyl oxazolidinones of Formula I-169. Compounds I-169 (wherein Z is —CH=CH—) are optionally converted to the saturated analogs I-170 under standard hydrogenation conditions.

Scheme 27

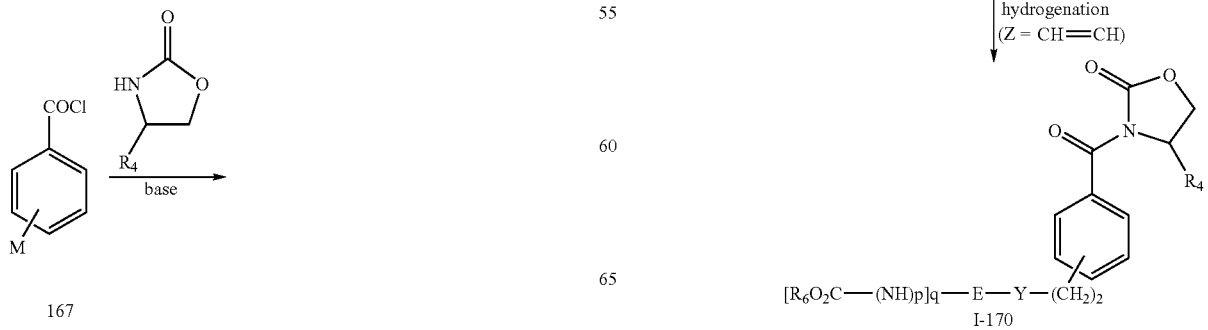

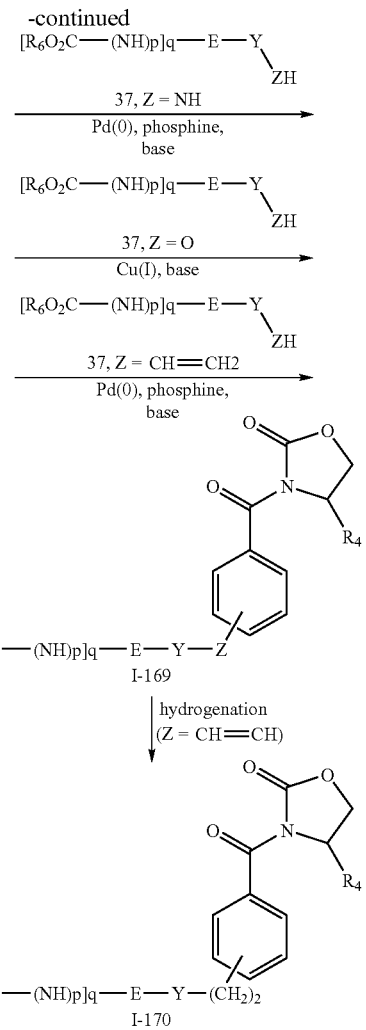

Compounds of Formula I wherein Q is taken from Q-36 are prepared as illustrated in Schemes 28.1 and 28.2. Reductive alkylation of the t-butylsulfide substituted piperazines with the readily available aldehydes 131 gives rise to the benzylic piperazines 171. Intermediates 171 are reacted with amines 37 (Z=NH), alcohols 37 (Z=O), or alkenes 37 (Z=—CH=CH$_2$) to give compounds 172, 173, or 174, respectively. Optionally, intermediates 174 are converted to the saturated analogs 175 under standard hydrogenation conditions.

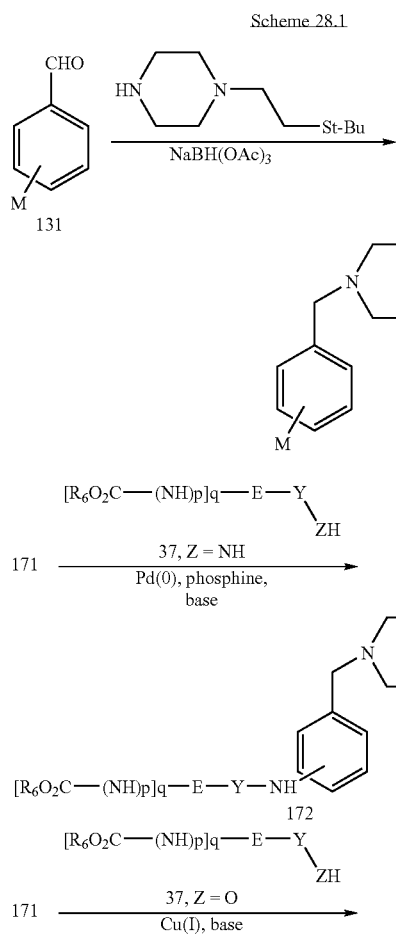

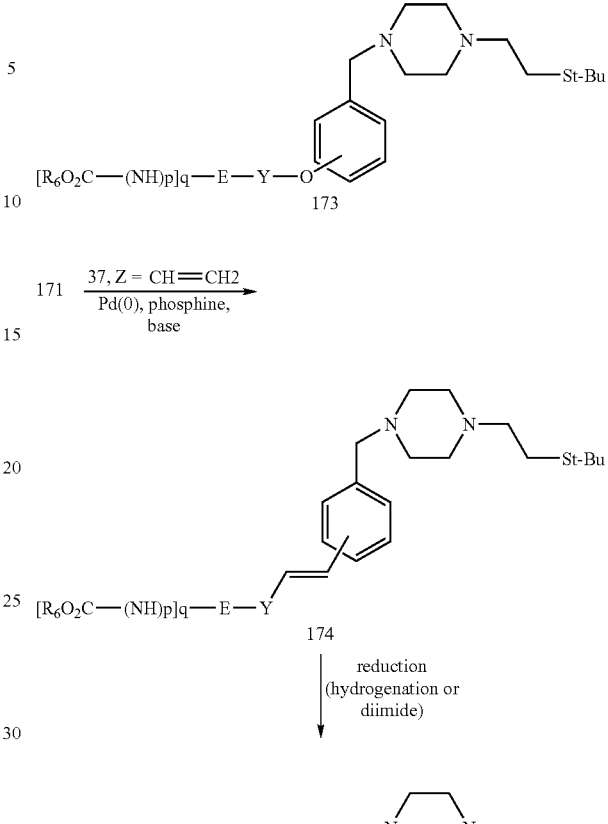

Scheme 28.2 illustrates the conversion of intermediate t-butylsulfides 172-175 to the sulfonic acids, employing a two step process involving acid-catalyzed deprotection of the t-butyl sulfide to the corresponding mercaptans, and subsequent peracid oxidation (preferably with peracetic acid or trifluoroperacetic acid) of the mercaptans to the desired sulfonic acids of Formula I-176.

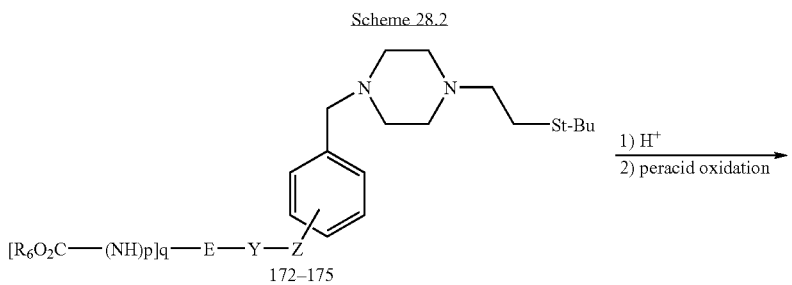

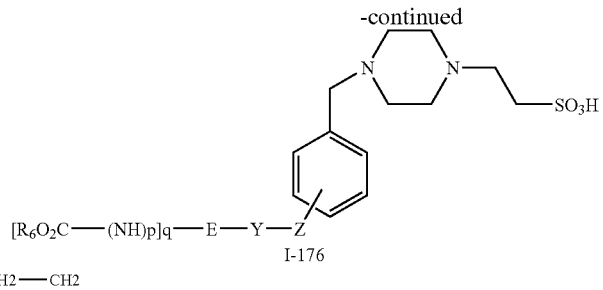

[R$_6$O$_2$C—(NH)p]q—E—Y—Z
I-176

Z = NH, O, CH=CH, CH2—CH2

In some instances a hybrid bcr-abl kinase inhibitor is prepared which also contains an ATP-pocket binding moiety or an allosteric pocket binding moiety R$_1$—X—A—D. The synthesis of moieties R$_1$—X—A—D are conducted as shown in Scheme 29. Readily available intermediates 177, which contain a group M capable of oxidative addition to palladium(0), are reacted with amines 178 (X=NH) Linder Buchwald Pd(0) amination conditions to afford 179. Alternatively amines or alcohols 178 (X=NH or O) are reacted thermally with 177 in the presence of base under nuclear aromatic substitution reaction conditions to afford 179. Alternatively, alcohols 178 (X=O) are reacted with 177 under Buchwald copper(I)-catalyzed conditions to afford 179. In cases where p=1, the carbamate of 179is removed, preferably under acidic conditions when R$_6$ is t-butyl, to afford amines 180. In cases where p=0, the esters 179 are converted to the acids 181 preferably under acidic conditions when R$_6$ is t-butyl.

Scheme 29

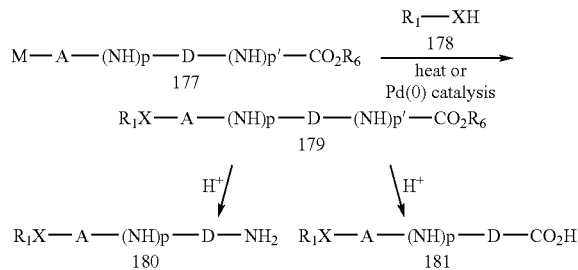

Another sequence for preparing amines or alcohols 180 is illustrated in Scheme 30. Reaction of amines or alcohols 178 with nitro(hetero)arenes 182 wherein M is a leaving group, preferably M is fluoride, or M is a group capable of oxidative insertion into palladium(0), preferably M is bromo, chloro, or iodo, gives intermediates 183. Reduction of the nitro group under standard hydrogenation conditions or treatment with a reducing metal, such as stannous chloride, gives amines 180.

Scheme 30

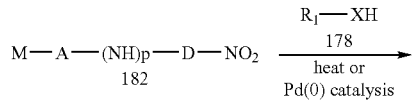

-continued $$R_1X-A-(NH)p-D-NO_2 \xrightarrow{reduction}$$
183
$$R_1X-A-(NH)p-D-NH_2$$
180

In instances when hybrid bcr-abl kinase inhibitors are prepared, compounds of Formula I-184 wherein q is 1 may be converted to amines I-185 (p=1) or acids I-186 (p=0) by analogy to the conditions described in Scheme 29. Compounds of Formula I-184 are prepared as illustrated in previous schemes 1.1, 2.1, 2.2, 3, 4, 5, 6, 7.1, 7.2, 8, 9, 10, 12, 14, 16.2, 17.2, 18, 19.1, 19.2, 19.3, 20, 21, 22, 23, 24, 25, 26, 27, or 28.2.

Scheme 31

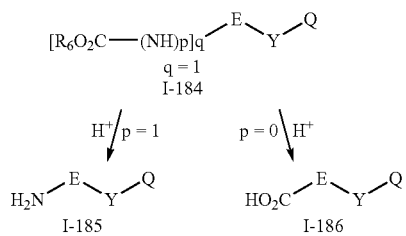

Compounds I-184 are taken from schemes 1.1, 2.1, 2.2, 3, 4, 5, 6, 7.1, 7.2, 8, 9, 10 12, 14, 16.2, 17.2, 18, 19.1, 19.2, 19.3, 20, 21, 22, 23, 24, 25, 26, 27, 28.2

The preparation of inhibitors of Formula I which contain an amide linkage —CO—NH—connecting the oxyanion pocket binding moieties and the R$_1$—X—A—D moieties are shown in Scheme 32. Treatment of acids 181 with an activating agent, preferably PyBOP in the presence of di-iso-propylethylamine, and amines I-185 gives compounds of Formula 1. Alternatively, retroamides of Formula I are formed by treatment of acids I-186 with PyBOP in the presence of di-iso-propylethylamine and amines 180.

Scheme 32

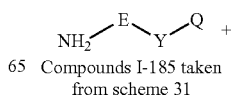

Compounds I-185 taken from scheme 31

-continued

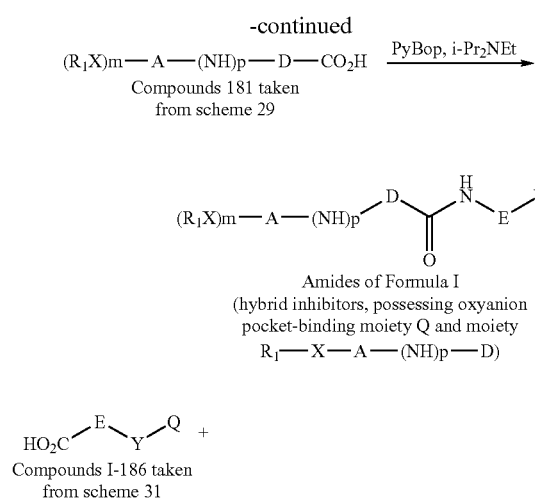

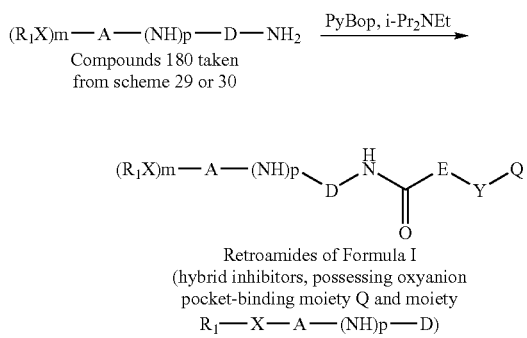

The preparation of inhibitors of Formula I which contain an urea linkage NH—CO—NH—connecting the oxyanion pocket binding moieties and R$_1$—X—A—D moieties are shown in Scheme 33. Treatment of amines I-185 with p-nitrophenyl chloroformate and base affords carbamates 187. Reaction of 187 with amines 180 gives ureas of Formula I.

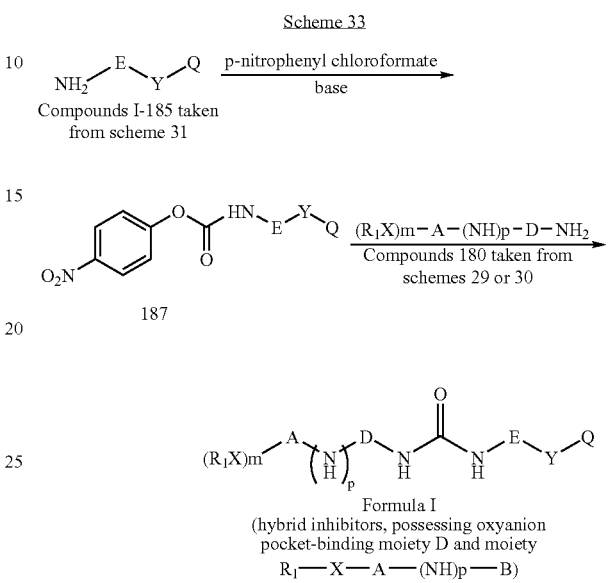

Alternatively, inhibitors of Formula I which contain an urea linkage NH—CO—NH—connecting the oxyanion pocket binding moieties and the R$_1$—X—A—D moieties are prepared as shown in Scheme 34. Treatment of amines 180 with p-nitrophenyl chloroformate and base affords carbamates 188. Reaction of 188 with amines I-185 gives ureas of Formula I.

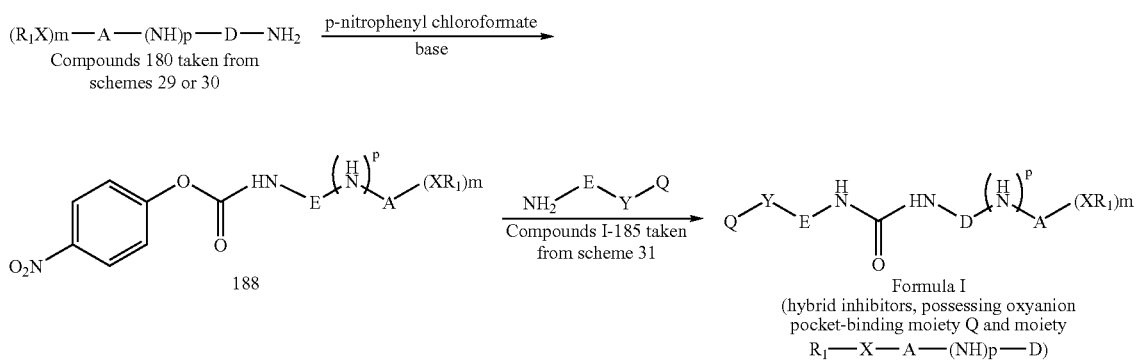

V. Biological Assessment of abl and bcr-abl Kinase Inhibiton

A continuous spectrophotometric kinase assay is used, wherein the production of adenosine diphosphate is coupled to the oxidation of NADH and measured as a reduction in absorbance at 340 nM. For details see: Barker, S. C. et al, *Biochemistry* (1995) 34:14843; and Schindler, T. et al, *Science* (2000) 289:1938.

Abl Kinase Assay

Activity of nonphosphorylated Abl kinase was determined by following the production of ADP from the kinase reaction through coupling with the pyruvate kinase/lactate dehydrogenase system (e.g., Schindler, et al. *Science* (2000) 289, 1938-1942). In this assay, the oxidation of NADH (thus the decrease at $A_{340\ nm}$) was continuous measured spectrophometrically. The reaction mixture (200 μl) contained Abl kinase (3.7 nM. Abl-2 from deCode), peptide substrate (EAIYAAPFAKKK, 0.5 mM), ATP (0.5 mM), $MgCl_2$ (5 mM), pyruvate kinase (16 units), lactate dehydrogenase (26 units), phosphoenol pyruvate (1 mM), and NADH (0.28 mM) in 100 mM Tris buffer, pH 7.5. The reaction was initiated by adding ATP. The absorption at 340 nm was monitored continuously for 3 to 4 hours at 30° C. on Polarstar Optima plate reader (BMG). Under these conditions, a turn over number ($k_{cat}$) of 1.4 $s^{-1}$ was obtained for the preparation of Abl kinase, which is similar to that (1.7 $s^{-1}$) reported for the nonphosphorylated enzyme (Brasher and Van Etten, JBC (2000) 275, 35631-35637). No autophosphorylation of Abl was observed under these conditions since the rate is constant throughout the entire reaction time and presumably because the concentration of the enzyme used is below the critical level (~10 nM) needed for the autophosphorylation (Brasher and Van Etten, JBC (2000) 275, 35631-35637). These results ensure what we monitored was the activity of nonphosphorylated Abl kinase.

Percentage of inhibition in the presence of an inhibitor was obtained by comparison of reaction rate (or slope) with that of a control. $IC_{50}$ value was calculated from a series of % inhibition values determined at a range of concentrations of the inhibitor using Prism. The IC50 values for Gleveec and PD 180970 were found to be 76 and 24 nM, respectively, which are close to that reported (Schindler, et al. Science (2000) 289, 1938-1942).

| Example # | % Inhi @ 10 uM | IC50, uM |
|---|---|---|
| 1 | 10 | |
| 2 | 9 | |
| 3 | 15 | |
| 4 | 24 | |
| 5 | 9 | |
| 6 | 13 | |
| 7 | 9 | |
| 8 | 20 | |
| 9 | 42 | |
| 10 | 16 | |
| 11 | 19 | |
| 12 | 52 | |
| 13 | 31 | |
| 15 | 7 | |
| 16 | 9 | |
| 17 | 18 | |
| 18 | 70 | 3 |
| 19 | 75 | 4 |
| 20 | 77 | 3 |
| 21 | 12 | |
| 23 | 10 | |
| 29 | 12 | |
| 35 | 1 | |
| 36 | 20 | |
| 37 | 10 | |
| 38 | 21 | |
| 39 | 13 | |
| 40 | 16 | |
| 42 | 33 | |
| 43 | 28 | |

EXAMPLES

The following examples set forth preferred methods in accordance with the invention. It is to be understood, however, that these examples are provided by way of illustration and nothing therein should be taken as a limitation upon the overall scope of the invention.

Reagents 6-methyl-$N^1$-(4-phenylpyrimidin-2-yl)benzene-1,3-diamine hydrochloride (Reagent AA) and 6-methyl-$N^1$-(4-phenylpyrimidin-2-yl)benzene-1,3-diamine hydrochloride (Reagent BB), N-Methyl-2-(methylcarbamoylmethylamino)-acetamide (Reagent CC), terephthalic acid monobenzyl ester (Reagent DD), 4-formyl-benzoic acid methyl ester (Reagent EE), 4-methyl-N-3-(4-(3-pyridyl)-pyrimidin-2-yl)-benzene-1,3-diamine hydrochloride (Reagent FF), [Boc-sulfamide] aminoester (Reagent GG) and 6-methyl-$N^1$-(4-morpholinopyrimidin-2-yl)benzene-1,3-diamine hydrochloride (Reagent HH) were synthesized according to literature procedures.

REAGENT AA

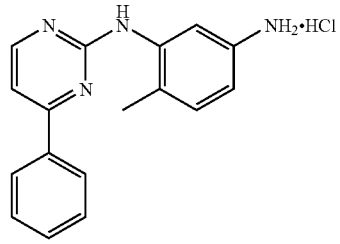

To a solution of N-(3-amino-4-methyl-phenyl)acetamide (5 g, 25 mmol) in DMF (5 ml) was added 2-chloro-4-phenylpyrimidine (4 g, 35 mmol) and KI (0.5 g, 3 mmol), which was stirred at 100° C. overnight, cooled to 10° C. and added to $H_2O$ (100 mL). The resulting mixture was extracted with $CH_2Cl_2$ (2×100 mL), the combined organic layers dried ($Na_2SO_4$) and concentrated in vacuo. The residue was dissolved in conc. HCl (10 mL), stirred at 80° C. for 2 h and concentrated in vacuo to yield 6-methyl-$N^1$-(4-phenylpyrimidin-2-yl)benzene-1,3-diamine hydrochloride (4.5 g, 65%). $^1$H NMR (CDCl3): 7.96 (m, 2H), 7.50-7.47 (m, 1H), 7.47-7.41 (m, 5H), 7.26 (m, 2H), 2.21(s, 3H); MS (ESI) m/e: 277 ($M^+$+1)

REAGENT BB

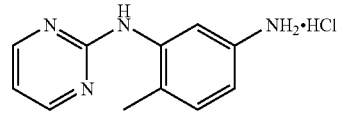

To a solution of N-(3-amino-4-methyl-phenyl) acetamide (5 g, 25 mmol) in DMF (5 mL) was added 2-chloropyrimidine (3.8 g, 33 mmol)-and KI (0.5 g), which was stirred at 100° C. overnight, cooled to 10° C. and added to $H_2O$ (100 mL). The resulting mixture was extracted with $CH_2Cl_2$ (2×100 mL), the combined organic layers dried ($Na_2SO_4$) and concentrated in vacuo. The residue was dissolved in conc. HCl (10 mL), stirred at 80° C. for 2 h and concentrated in vacuo to yield 6-methyl-$N^1$-(4-phenylpyrimidin-2-yl)benzene-1,3-diamine hydrochloride (3.75 g, 75%). $^1$H NMR (CDCl3): 8.36 (dd, J=15.2 & 4.8 Hz, 2H), 7.46 (d, J=2.4 Hz, 1H), 6.97 (d, J=8.0 Hz, 1H), 7.26 (s, 1H), 6.67 (t, J=4.8 Hz, 1H), 6.39 (dd, J=8.0, 2.4, Hz, 1H), 2.20 (s, 3H); MS (ESI) m/e: 201 (M⁺+1).

REAGENT CC

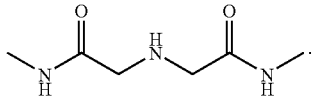

To a solution of benzyl amine (16.5 g, 154 mmol) and ethyl bromoacetate (51.5 g, 308 mmol) in ethanol (500 mL) was added K$_2$CO$_3$ (127.5 g, 924 mmol). The mixture was stirred at RT for 3 h, was filtered, washed with EtOH, concentrated in vacuo and chromatographed to yield benzyl-methoxycarbonylmethyl-amino)-acetic acid ethyl ester (29.02 g, 67%). $^1$H NMR CDCl$_3$) δ 7.39-7.23 (m, 5H), 4.16 (q, J=7.2 Hz, 4H), 3.91 (s, 2H), 3.54 (s, 4H), 1.26 (t, J=7.2 Hz, 6H); MS (ESI): m/e: 280 (M⁺+H).

A solution of (benzyl-methoxycarbonylmethyl-amino)-acetic acid methyl ester (7.70 g, 27.6 mmol) in methylamine alcohol solution (25-30%, 50 mL) was heated to 50° C. in a sealed tube for 3 h, cooled to RT and concentrated in vacuo to yield 2-(benzyl-methylcarbamoylmethyl-amino)N-methyl-acetamide in quantitative yield (7.63 g). $^1$HNMR (CDCl$_3$) δ 7.35-7.28 (m, 5H), 6.75(br s, 2H), 3.71(s, 2H), 3.20 (s, 4H), 2.81(d, J=5.6 Hz, 6H); MS (ESI) m/e 250(M+H⁺)

The mixture of 2-(benzyl-methylcarbamoylmethyl-amino)N-methyl-acetamid (3.09 g, 11.2 mmol) in MeOH (30 mL) was added 10% Pd/C (0.15 g). The mixture was stirred and heated to 40° C. under 40 psi H$_2$ for 10 h, filtered and concentrated in vacuo to yield N-methyl-2-(methylcarbamoylmethyl-amino)-acetamide in quantitative yield (1.76 g). $^1$HNMR(CDCl$_3$) δ 6.95(brs, 2H), 3.23(s, 4H), 2.79(d, J=4.8 Hz, 6H), 2.25(brs, 1H); MS (ESI) m/e 160(M+H⁺)

REAGENT DD

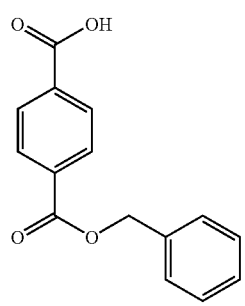

REAGENT EE

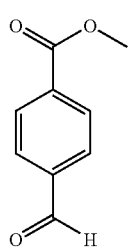

REAGENT FF

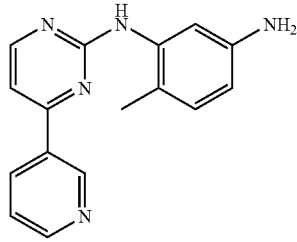

REAGENT HH

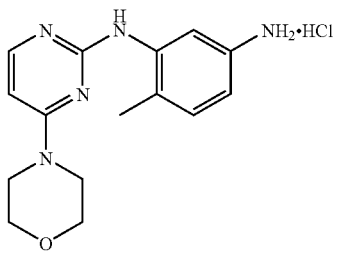

To a solution of N-(3-amino-4-methyl-phenyl) acetamide (5 g, 41 mmol) in DMF (5 ml) was added 4-(2-chloro-pyrimidin-4-yl)-morpholine (8.1 g, 40 mmol) and KI (0.5 g, 3 mmol), which was stirred at 100° C. overnight, cooled to 10° C. and added to H$_2$O (100 mL). The resulting mixture was extracted with CH$_2$Cl$_2$ (2×100 mL), the combined organic layers dried (Na$_2$SO$_4$) and concentrated in vacuo. The residue was dissolved in conc. HCl (10 mL), stirred at 80° C. for 2 h and concentrated in vacuo to yield 6-methyl-N$^1$-(4-morpholinopyrimidin-2-yl)benzene-1,3-diamine hydrochloride (5.0 g, 65%). $^1$H NMR (DMSO-d6): 8.00 (d, J=7.2 Hz, 1H), 7.57 (brs, 1H), 7.36 (d, J=8.4 Hz, 1H), 7.14 (dd, J=8.4, 1.6 Hz, 1H), 6.65 (d, J=7.2 Hz, 1H), 3.69 (s, 4H), 3.66 (s, 4H), 2.25 (s, 3H). MS (ESI) m/e: 286 (M⁺+1).

Example A

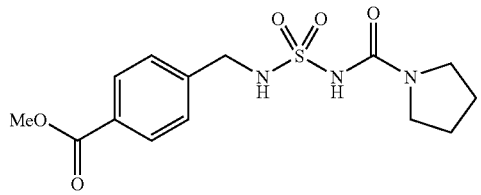

To a stirred solution of chlorosulfonyl isocyanate (3 g, 21 mmol) in of CH$_2$Cl$_2$ (50 mL) at 0° C. was slowly added pyrrolidine (1.5 g, 21 mmol) while the reaction temperature was controlled between 0-5° C. After being stirred for 1.5 h, a solution of 4-Aminomethyl-benzoic acid methyl ester hydrochloride (4.7 g, 23 mmol) and triethylamine (6.4 g, 63 mmol) in CH$_2$Cl$_2$ (120 mL) was slowly added while the reaction temperature was controlled between 0-5° C. When the addition was completed, the reaction solution was awarded to RT, stirred overnight, then poured into of 10% HCl (130 mL) saturated with NaCl. The organic layer was separated and the aqueous layer was extracted with Et$_2$O (3×80 mL). The combined organic layers were dried (Na$_2$SO$_4$) and concentrated in vacuo to yield the crude product, which was purified by column chromatography on a silica gel to yield pure pyrolidine carboxamide, N-[(4- carbomethoxybenzyl)amino]sulfonyl (3 g, 43% yield). ¹H NMR (DMSO-d6) δ7.70 (d, J=2.1 Hz, 2H), 7.28 (d, J=2.1 Hz, 2H), 4.84 (s, 2H), 3.83 (s, 3H), 3.15 (m, 4H), 1.67 (m, 4H); MS (ESI) m/e: 342 (M⁺+1).

Example B

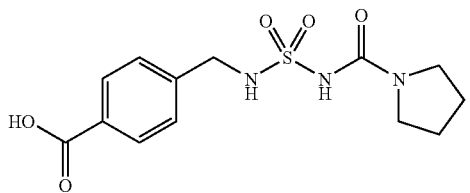

A solution of Example A (60 mg, 0.18 mmol) in THF (10 mL) was added to 3N LiOH (10 mL) at RT, stirred overnight, acidified with 1 N HCl, and extracted with EtOAc. The organic layer was dried (Na₂SO₄) and concentrated to yield pyrolidine carboxamide, N-[(4-carboxybenzyl)amino]sulfonyl (40 mg, 70% yield). ¹H NMR (DMSO-d6) δ12.87 (s, 1H), 10.01 (s, 1H), 7.88 (d, J=2.0 Hz, 2H), 7.33 (d, J=2.0 Hz, 2H), 6.90 (m, 1H ), 4.28 (s, 2H), 3.28 (m, 4H), 1.75 (m, 4H); MS (ESI) m/e: 327 (M⁺+1).

Example 1

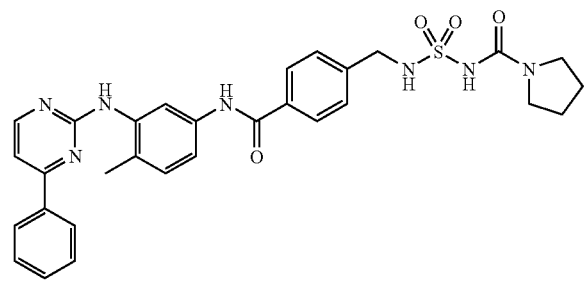

To a solution of Reagent AA (14 mg, 0.048 mmol) in anhydrous DMF (1 mL) was added Et₃N (26 μL, 0.18 mmol) at RT. The reaction mixture was stirred for 5 min, followed by addition of Example B (12 mg, 0.038 mmol), EDCI (14 mg, 0.055 mmol) and HOBt (7.4 mg, 0.055 mml). The reaction mixture was stirred over night at RT. Removal of solvent in vacuo followed by preparative HPLC yielded pure Example 1 (16 mg, 76%). ¹H NMR (CD₃OD) δ 8.32 (d, J=5.6 Hz, 1H), 8.24 (d, J=7.2 Hz, 2H), 8.09 (d, J=2.0 Hz, 1H), 7.92 (d, J=8.0 Hz, 2H), 7.60-7.40 (m, 5H), 7.44 (d, J=8.4 Hz, 2H), 7.36 (d, J=8.4 Hz, 1H), 4.43 (s, 2H), 3.41 (m, 4H), 2.34 (s, 3H), 1.89 (m 4H); MS (ESI) m/e: 586 (M⁺+1).

Example 2

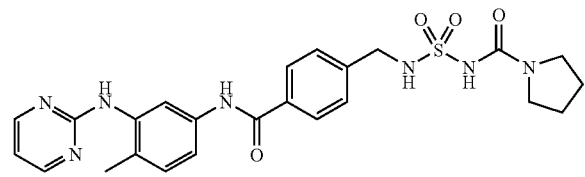

The title compound was synthesized following the procedure for the preparation of Example 1, utilizing Example B and Reagent BB. ¹H NMR (CD₃OD) δ 8.46 (d, J=5.2 Hz, 2H), 7.97 (dd, J=8.0, 2.0 Hz, 1H), 7.91 (d, J=8.0 Hz, 2H), 7.50 (dd, J=8.0, 2.0 Hz, 1H), 7.44 (d, J=8.0 Hz, 2H), 7.33 (d, J=8.0 Hz, 1H), 6.92 (t, J=4.2 Hz, 1H), 4.43 (s, 2H), 3.41 (m, 4H), 2.28 (s, 3H), 1.89 (m, 4H); MS (ESI) m/e: 509 (M⁺+1).

Example C

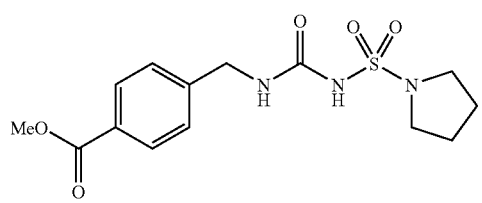

To a stirred solution of chlorosulfonyl isocyanate (3 g, 21 mmol) in 50 mL of CH₂Cl₂ (50 mL) at 0° C. was slowly added a solution of 4-aminomethyl-benzoic acid methyl ester hydrochloride (4.7 g, 23 mmol) and triethylamine (6.4 g, 63 mmol) in CH₂Cl₂ (120 mL) while the reaction temperature was controlled between 0-5° C. After being stirred for 1.5 h, pyrrolidine (1.5 g, 21 mmol) was slowly added while the reaction temperature was controlled between 0-5° C. When the addition was completed, the reaction solution was allowed to warm to RT, stirred overnight, then poured into of 10% HCl (130 mL) saturated with NaCl. The organic layer was separated and the aqueous layer was extracted with Et₂O (3×80 mL). The combined organic layers were dried (Na₂SO₄) and concentrated to yield the crude product, which was purified by column chromatography on a silica gel to yield pure Example C (2.5 g, 35% yield). ¹H NMR (DMSO-d6) δ7.87 (d, J=2.1 Hz, 2 H), 7.28 (d, J=2.1 Hz, 2 H), 4.89 (s, 2 H) 3.82 (s, 3 H), 3.15 (m, 4 H), 1.68 (m, 4 H); MS (ESI) m/e: 342 (M⁺+1).

Example D

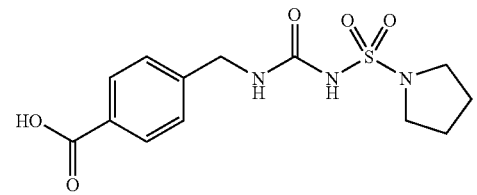

The title compound using synthesized following the procedure for Example B utilizing Example C. ¹H NMR (CD₃OD) δ7.98 (d, J=2.0 Hz, 2 H), 7.38 (d, J=2.0 Hz, 2 H), 4.41 (s, 2 H), 3.39 (m, 4 H), 1.87 (m, 4 H); MS (ESI) m/e: 327 (M⁺+1).

Example 3

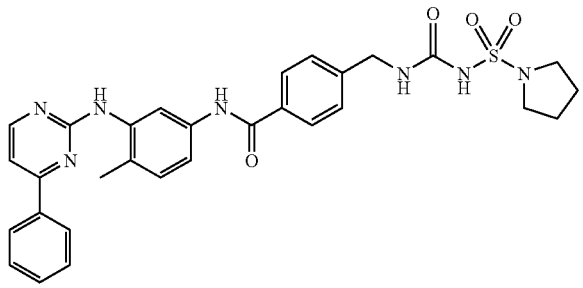

The title compound was synthesized following the procedure for the preparation of Example 1 utilizing Example D and Reagent AA. $^1$H NMR (CD$_3$OD) δ8.31 (m, 1H), 8.23 (d, J=2.1 Hz, 2H), 8.06 (s, 1H), 7.81 (d, J=2.1 Hz, 2H), 7.62 (m, 1H), 7.54 (m, 4H), 7.43 (d, J=2.1 Hz, 2H), 7.37 (d, J=2.1 Hz, 1H ), 4.43 (s, 2H), 3.40 (m, 4 H), 2.33 (s, 3H), 1.89 (m, 4H); MS (ESI) m/e: 586 (M$^+$+1).

Example 4

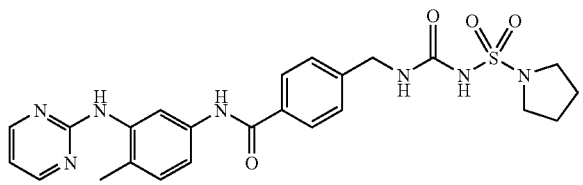

The title compound was synthesized following the procedure of the preparation of Example 1 utilizing Example D and Reagent BB. $^1$H NMR (CD$_3$OD) δ8.45 (br s, 2H), 7.96 (d, J=4.0 Hz, 1H), 7.90 (d, J=8.0 Hz, 2H), 7.50 dd, J=8.0, 2.0 Hz, 1H), 7.62 (m, 1H), 7.43 (d, J=8.4 Hz, 2H), 7.29 (d, J=8.4 Hz, 1H ), 6.87 (t, J=4.8 Hz, 1H), 4.43 (s, 2H), 3.40 (m, 4 H), 2.27 (s, 3H), 1.89 (m, 4H); MS (ESI) m/e: 510 (M$^+$+1).

Example D

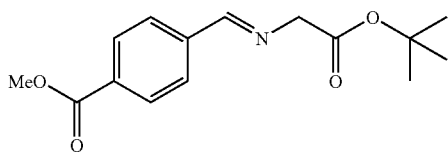

To a suspension of glycine ethyl ester hydrochloride (6.0 g, 34 mmol) in anhydrous CH$_2$Cl$_2$ (34 mL) was added triethylamine (3.4 g, 34 mmol) followed by anhydrous magnesium sulfate (12.2 g, 102 mmol) and Reagent EE (6.0 g, 34 mmol). After refluxing for 2 h , the solid was filtered, washed with brine, dried (MgSO$_4$) and concentrated in vacuo to produce methyl 4-((E)-((t-butoxycarbonyl)methylimino)methyl)benzoate which was used without further purification (8.2 g, 97% yield). $^1$H NMR (CDCl$_3$) δ 8.30 (s, 1H), 8.07 (d, J=8.4 Hz, 2H) 7.84 (d, J=8.4 Hz, 2H) 4.34 (s, 2H) 3.91 (s, 3H) 1.49 (s, 9H).

Example E

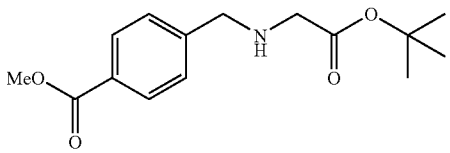

To a solution of Example D (8.5 g, 30 mmol) in MeOH (80 mL) was slowly added solid NaBH$_4$ (3.42 g, 90 mmol) while the reaction temperature was controlled below 20° C. After stirring for 2 h, the reaction was quenched with H$_2$O, extracted with EtOAc (3×100 mL) and the combined organic layers were washed with brine, dried (Na$_2$SO$_4$), concentrated in vacuo. The residue was purified via flash column chromatography to yield methyl 4-(((t-butoxycarbonyl)methylamino)methyl)benzoate (6.55 g, 77% yield). $^1$H NMR (CDCl$_3$) δ 7.98 (d, J=8.4 Hz, 2H), 7.40 (d, J=8.4 Hz, 2H), 3.90 (s, 3H,) 3.84 (s, 2H) 3.29 (s, 2H) 1.46 (s, 9H).

Example F

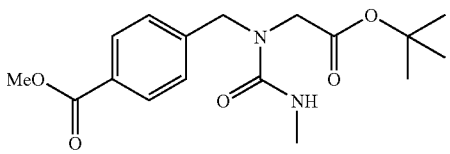

To a solution of Example E (5.1 g, 18 mmol) in THF (80 mL) was added K$_2$CO$_3$ (4.2 g, 30 mmol) and methylcarbamic acid 4-nitro-phenyl ester (3.6 g, 18 mmol). After being stirred overnight, the resulting solid was filtered. After adding H$_2$O and EtOAc to the filtrate, the organic layer was separated and the aqueous layer was extracted with EtOAc (3×100 mL). The combined organic layers were washed with brine, dried (Na$_2$SO$_4$), concentrated in vacuo and purified by flash chromatography to yield Example F (4.4 g, 73%). $^1$H NMR (CDCl$_3$) 8.01 (d, J=8.4 Hz, 2H) 7.35 (d, J=8.4 Hz, 2H) 4.59 (m, 1H) 4.57 (s, 2H) 3.91 (s, 3H) 3.90 (s, 2H) 2.79 (d, J=4.4 Hz, 3H) 1.43 (s, 9H).

Example G

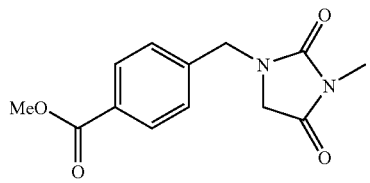

To a suspension of NaH (0.28 g, 7 mmol) in THF (80 mL) at RT was slowly added a solution of Example F (1.85 g, 5.5 mmol) in THF (50 mL). After stirring for 2 h, the resulting solid was filtered. After adding water and EtOAc to the filtrate, the organic layer was separated and the aqueous layer was extracted with EtOAc (3×100 mL). The combined organic layers were washed with brine, dried (Na$_2$SO$_4$), and concentrated in vacuo to yield methyl 4-((3-methyl-2,4-dioxoimidazolidin-1-yl)methyl)benzoate (1.3 g, 90%). ¹H NMR (CDCl₃) 8.03 (d, J=8.4 Hz, 2H) 7.32 (d, J=8.4 Hz, 2H) 4.62 (s, 2H) 3.90 (s, 3H) 3.73 (s, 2H) 3.08 (s, 3H).

Example H

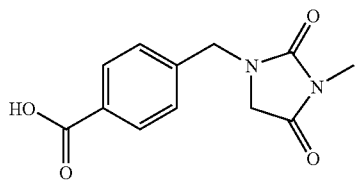

To the solution of Example G (900 mg, 3.44 mmol) in MeOH (30 mL) was added conc. HCl (10 mL). The resulting solution was heated to reflux for 1 h, quenched with saturated Na₂CO₃ (100 mL), and extracted with CH₂Cl₂ (100 mL). After separation, the organic layer was washed with brine, dried (Na₂SO₄), and concentrated in vacuo to yield 4-((3-methyl-2,4-dioxoimidazolidin-1-yl)methyl)benzoic acid as a yellow solid. The crude product was used without further purification.

Example 5

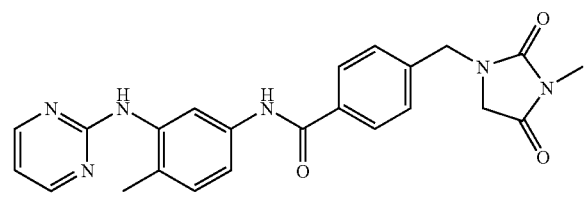

To a solution of Example H (200 mg, 0.81 mmol) in DMF (10 mL) were added EDCI (200 mg, 1.0 mmol), HOBt (150 mg, 1.5 mmol), NMM (0.5 mL) and Reagent BB (300 mg, 1.5 mmol). After being stirred at RT overnight, the solvent was removed under vacuum. The resulting residue was purified by preparative HPLC to yield pure 4-((3-methyl-2,4-dioxoimidazolidin-1-yl)methyl)-N-(4-methyl-3-(pyrimidin-2-ylamino)phenyl)benzamide (20 mg). ¹H NMR (DMSO-d) δ:10.14 (s, 1H), 8.87 (s, 1H),8.35 (d, J=4.8 Hz, 2H), 7.91 (d, J=8 Hz, 2 H), 7.84 (d, J=1.6 Hz, 1H), 7.45 (dd, J=8.4, 2.0 Hz, 1H), 7.41 (d, J=7.7 Hz, 2H), 7.15 (d, J=8.0 Hz, 1H), 6.75 (t, J=4.8 Hz, 1H), 4.56 (s, 2H), 3.89 (s, 2H), 2.87 (s, 3H), 2.15 (s, 3H); MS (ESI) m/e: 431 (M⁺+1).

Example 6

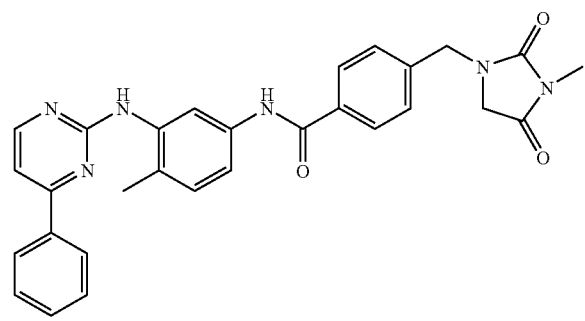

The title compound was synthesized following the procedure for the preparation of Example 5 utilizing Example H and Reagent AA to yield N-(3-(4-phenylpyrimidin-2-ylamino)-4-methylphenyl)-4-((3-methyl-2,4-dioxoimidazolidin-1-yl)methyl)benzamide. ¹H NMR (CDCl₃-d) δ:8.45 (s, 1H), 8.39 (d, J=5.6 Hz, 2H), 8.19 (s, 1H), 8.08 (dd, J=7.2 Hz, 2H), 7.84 (d, J=8.4 Hz, 2H), 7.32-7.46 (m, 5 H), 7.25-7.29 (m, 2H), 7.13-7.17 (m, 2H), 4.56 (s, 2H), 3.70 (s, 2H), 3.03 (s, 3H), 2.30 (s, 3H). Ms (ESI) m/e: 507 (M⁺+1).

Example I

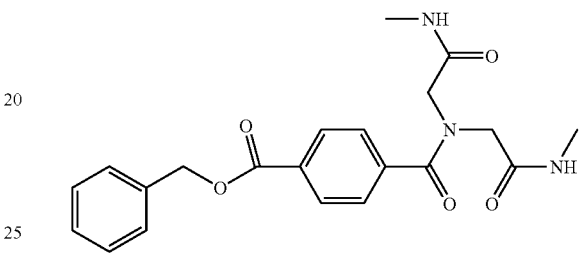

To a solution of Reagent CC (0.68 g, 4.30 mmol) in dry CH₂Cl₂ (20 mL) under N₂ were added NMM (2.70 g, 27.2 mmol), HOBt (0:91 g, 6.7 mmol), EDCI (1.26 g, 6.6 mmol) and reagent DD (1.5 g, 5.90 mmol). After being stirred at RT overnight, the solvent was removed under reduced pressure. The residual was washed with H₂O, saturated aqueous K₂CO₃ and H₂O to yield the white solid, which was dried in vacuo to yield benzyl 4-(bis((methylcarbamoyl)methyl)carbamoyl)benzoate (0.72 g, 42% yield). ¹H NMR(CDCl₃) δ8.74 (s, 1H), 8.10 (d, J=8.4 Hz, 2H), 7.50 (d, J=8.4 Hz, 2H), 7.46 (m, 5H), 6.35 (s, 1H), 5.37 (s, 2H), 3.94 (d, J=10.8 Hz, 4H) 2.89 (m, 6H); MS (ESI) m/e: 398 (M⁺+1).

Example J

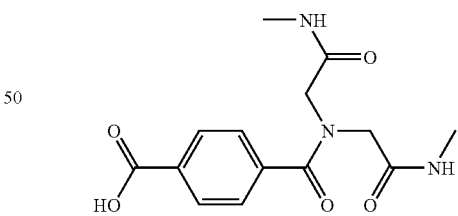

To a solution of Example I (0.73 g, 1.84 mmol) in MeOH (30 mL) was added 10% Pd/C (200 mg). The reaction mixture was then stirred at ambient temperature under 1 atmosphere of H₂ for 45 min. The reaction mixture was filtered, the solid washed with EtOH, and the combined organics concentrated in vacuo to yield 4-(bis((methylcarbamoyl)methyl)carbamoyl)benzoic acid (0.52 g, 92% yield). ¹H NMR (CDCl₃) δ9.16 (s, 1H), 8.05 (d, J=8.4 Hz, 2H), 7.49 (d, J=8.4 Hz, 2H), 4.04 (d, J=6 Hz, 4H), 2.94 (m, 6H); MS (ESI) m/e: 308 (M⁺+1).

Example 7

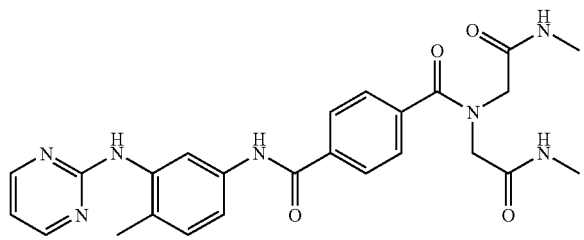

The title compound was synthesized following the procedure for the preparation of Example 1 utilizing Example J and Reagent BB to yield $N^1,N^1$-bis((methylcarbamoyl)methyl)-$N^4$-(4-methyl-3-(pyrimidin-2-ylamino)phenyl)terephthalamide. $^1$H NMR (CD$_3$OD) δ 8.43 (d, J=5.2 Hz, 2H), 7.98 (d, J=8.4 Hz, 1H), 7.97 (s, 1H), 7.58 (d, J=8.4 Hz, 2H), 7.50 (dd, J=8.0, 2.0 Hz, 1H), 7.30 (d, J=8.4 Hz, 1H), 6.86 (t, J=5.2 Hz, 1H), 4.18 (s, 2H), 4.04 (s, 2H), 2.81 (s, 3H), 2.73 (s, 3H), 2.28 (s, 3H). MS (ESI) m/e: 490 (M$^+$+1).

Example 8

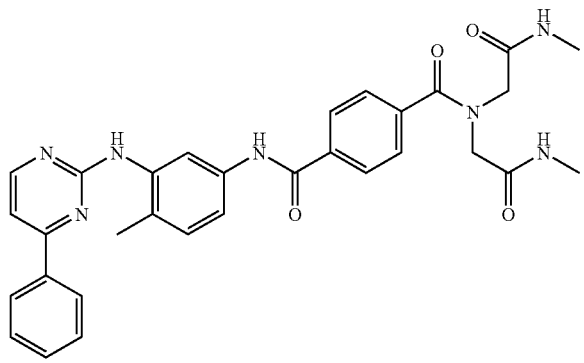

The title compound was synthesized following the procedure for the preparation of Example 1 utilizing Example J and Reagent AA to yield $N^1,N^1$-bis((methylcarbamoyl)methyl)-$N^4$-(3-(4-phenylpyrimidin-2-ylamino)4-methylphenyl)terephthalamide. $^1$H NMR (DMSO-d$_6$) δ 10.26 (br s, 1H), 8.85 (br s, 1H), 8.44 (d, J=4.8 Hz, 1H), 8.40 (d, J=3.2 Hz, 1H), 8.19 (m, 1H), 8.11 (d, J=5.8 Hz, 1H), 8.06 (s, 1H), 7.97 (d, J=8.4 Hz, 2H), 7.50-7.45 (m, 5H), 7.32 (d, J=5.2 Hz, 1H), 7.18 (d, J=8.0 Hz, 1H), 4.00 (s, 2H), 3.87 (s, 2H), 2.63 (d, J=4.0 Hz, 1H), 2.58 (d, J=4.0 Hz, 1H), 2.21 (s, 3H); MS (ESI) m/e: 566 (M$^+$+1).

Example K

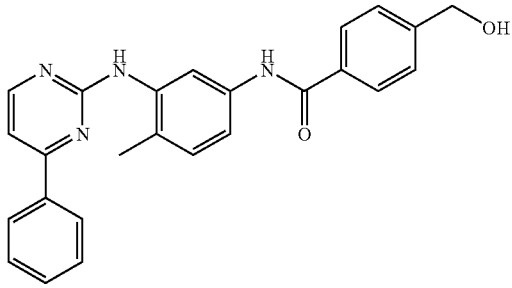

To the solution of Reagent AA (840 mg, 2.72 mmol) and 4-hydroxymethyl-benzoic acid (490 mg, 3.20 mmol) in dry DMF (20 mL) was added EDCl (700 mg, 3.62 mmol), HOBt (500 mg, 3.73 mmol), and NMM (0.5 mL, 3.95 mmol). The resulting mixture was stirred at RT overnight, into H$_2$O and extracted with CH$_2$Cl$_2$. The organic layer was washed with saturated Na$_2$CO$_3$, purified by column chromatography on silica gel yielded N-(3-(4-phenylpyrimidin-2-ylamino)-4-methylphenyl)-4-(hydroxymethyl)benzamide (410 mg, 36.8%). $^1$H NMR (DMSO-d$_6$) δ: 10.12 (s, 1H), 8.84 (s, 1H), 8.44(d, J=5.2 Hz, 1H), 8.11 (d, J=4.0 Hz, 2H), 8.05 (s, 1H), 7.91 (d, J=8.0 Hz, 2H) 7.45 (m, 5H), 7.32(d, J=5.2 Hz, 1H), 7.19 (d, J=7.8 Hz, 1H), 4.56 (d, J=5.6 Hz, 2H), 2.30 (s, 3H); MS (ESI) m/e: 411.20 (M$^+$+1).

Example L

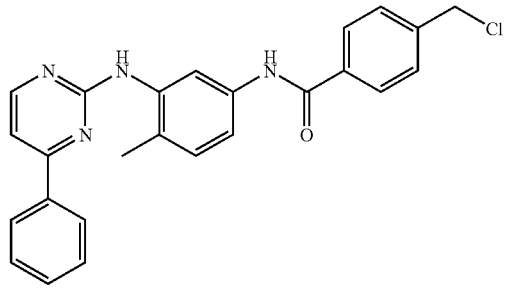

To the solution of Example K (410 mg, 0.99 mmol) in 1,4-dioxane (40 mL) was slowly added SOCl$_2$ (650 mg, 5.50 mmol) at RT. After being stirred at RT for 3 h, the solvent and excessive SOCl$_2$ was removed in vacuo to yield N-(3-(4-phenylpyrimidin-2-ylamino)-4-methylphenyl)-4-(chloromethyl)benzamide as a yellow solid (460 mg), which was used without further purification. $^1$H NMR (CDCl$_3$-d$_6$) δ: 8.42 (s, 1H), 8.22 (d, J=6.0 Hz, 3H), 8.05 (m, 1H), 7.94 (d, J=1.0 Hz, 2H) 7.53-7.62 (m, 5H), 7.26 (s, 2H), 4.63 (d, J=5.4 Hz, 2H), 2.44 (s, 3H); MS (ESI) m/e: 429.20 (M$^+$+1)

Example M

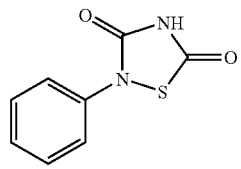

To the solution of phenyl-urea (13.0 g, 95.48 mol) in THF (100 mL) was slowly added chlorocarbonyl sulfenylchloride (13 mL, 148.85 mmol) at RT. The reaction mixture was refluxed overnight, the volatiles removed in vacuo yielded 2-phenyl-1,2,4-thiadiazolidine-3,5-dione as a white solid (4.0 g, yield 20%). $^1$H NMR (DMSO-d$_6$) δ:12.49 (s, 1H), 7.51 (d, J=8.0 Hz, 2H), 7.43 (t, J=7.6 Hz, 2H), 7.27 (t, J=7.2 Hz, 1 H).

Example 9

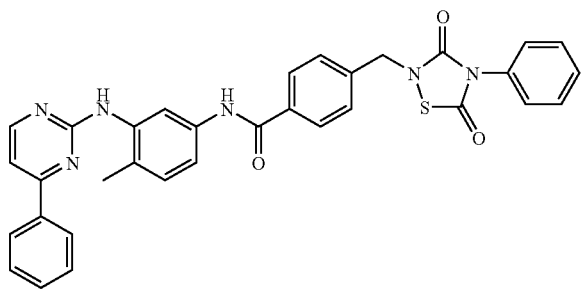

To a solution of Example M (400 mg, 2.06 mmol) in anhydrous DMF and THF (1:1) under $N_2$ at 0° C. was slowly added NaH (165 mg, 4.24 mmol). After stirring at 0° C. for 0.5 h, Example L (300 mg, 0.70 mmol) was added. The solution was heated to 40° C., stirred for 3 h and quenched with AcOH (0.5 mL). Removal of the solvent followed by purification via preparative HPLC yielded N-(3-(4-phenylpyrimidin-2-ylamino)-4-methylphenyl)-4-((3,5-dioxo-4-phenyl-1,2,4-thiadiazolidin-2-yl)methyl)benzamide (50 mg, yield 12%). $^1$HNMR (DMSO-$d_6$) δ: 10.18 (s, 1 H), 8.88 (s, 1 H), 8.43 (d, J=5.2 Hz, 1H), 8.12(dd, J=7.6 1.6 Hz, 2H), 8.05 (s, 1 H), 7.92 (d, J=8.4 Hz, 2H), 7.58 (d, J=9.2 1.6 Hz, 2H), 7.44-7.34 (t, J=6.0 Hz, 2H), 7.18 (d, J=8.8 Hz, 1H), 4.91 (s, 2 H), 2.20(s, 3 H); MS (ESI) (m/e): 587.18 ($M^+$+1).

Example N

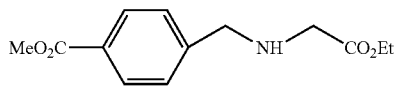

Glycine ethyl ester hydrochloride (11.1 g, 79 mmol), and Reagent EE (10 g, 61 mmol) were dissolved in absolute EtOH (300 mL). NaCNBH$_3$ (8.4 g, 134 mmol) was added in 4 portions and the reaction mixture was stirred at RT overnight. The solvent was removed under reduced pressure and the residue was dissolved in EtOAc. The organic layer was washed with 1N HCl solution, saturated NaHCO$_3$ and brine, and dried and concentrated in vacuo to yield methyl 4-(((ethoxycarbonyl)methylamino)methyl)benzoate (8 g). $^1$H-NMR (CDCl$_3$): 7.97 (d, J=6.8 Hz, 2H), 7.39 (d, J=8.8 Hz, 2H), 4.16 (q, J=7.2 Hz, 2H), 3.88 (s, 3H), 3.84 (s, 2H), 3.37 (s, 2H), 1.94 (s, 1H), 1.24 (t, J=7.2 Hz, 3H).

Example O

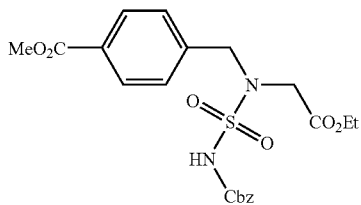

To a stirred solution of chlorosulfonyl isocyanate (2.2 g, 15.2 mmol) in CH$_2$Cl$_2$ (40 mL) was added benzyl alcohol (1.64 g, 15.2 mmol) at 0° C. And the reaction temperature was kept not to rise above 5° C. After stirred for 1 h, a solution of Example N (4.2 g, 16.7 mmol) and triethylamine (6 mL, 4.3 g, 42.6 mmol) in CH$_2$Cl$_2$ (40 mL) was added at a rate to keep the reaction temperature not to rise above 5° C. When the addition was completed, the reaction solution was allowed to warm to RT and stirred overnight. The reaction mixture was poured into 1N HCl saturated with NaCl (300 mL). The organic layer was separated and the aqueous layer was extracted with CH$_2$Cl$_2$ (2×100 mL). The combined organic layers were dried with Na$_2$SO$_4$, and concentrated. The crude product was recrystallized from CH$_2$Cl$_2$/n-hexane to afford desired Example O (5.9 g, 76.6% yield). $^1$H-NMR (CDCl$_3$): 8.00 (d, J=8.4 Hz, 2H), 7.87 (s, 1H), 7.36 (m, 5H), 5.29 (s, 2H), 4.65 (s, 2H), 4.15 (q, J=7.2 Hz, 2H), 3.98 (s, 2H), 3.92 (s, 3H), 1.24 (t, 3H).

Example P

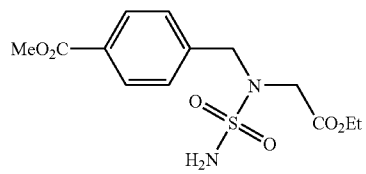

To a solution of Example O (5.5 g, 118 mmol) in solvent of MeOH (50 mL) and EtOAc (50 mL) was added 10% Pd/C (0.8 g) under $N_2$. Then the resulting mixture was stirred at RT under H$_2$ (60 psi) overnight. The solvent was removed to afford white solid Example P (3.4 g, 85% yield). $^1$H-NMR (CDCl$_3$): 8.02 (d, J=8.4 Hz, 2H), 7.41 (d, J=8.4 Hz, 2H), 5.20 (s, 2H), 4.44 (s, 2H), 4.19 (q, J=7.2 Hz, 2H), 3.91 (s, 3H), 3.90 (s, 2H), 1.25 (t, J=7.2 Hz, 3H)

Example Q

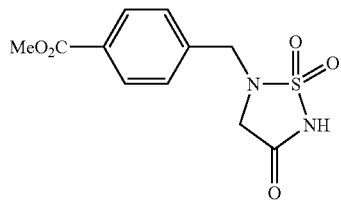

A NaOMe solution was prepared by adding NaH (60%, dispersion in mineral oil, 43.5 mg, 1.1 mmol) to MeOH (30 mL). Example P (300 mg, 0.9 mmol) was added to the NaOMe-MeOH solution and the reaction was stirred at RT overnight. The solution was concentrated in vacuo and the residue was dissolved in H$_2$O (30 mL). The aqueous solution was acidified with 3N HCl and the precipitate was filtered and collected to yield methyl 4-(1,4-trioxo-[1,2,5]thiadiazolidin-2-ylmethyl)-benzoate (120 mg, 40% yield). $^1$H-NMR (DMSO-d): 7.92 (d, J=8.4 Hz, 2H), 7.49 (d, J=8 Hz, 2H), 4.35 (s, 2H), 3.99 (s, 2H), 3.83 (s, 3H).

Example R

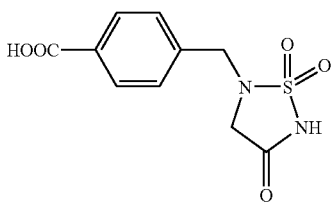

Example Q (100 mg, 0.35 mmol) in THF (4 mL) and 1.5 mL of 2N aq. LiOH solution was stirred at RT for 3 h. The solvent was removed under reduced pressure and the residue was dissolved in $H_2O$ (20 mL) and acidified with aqueous 3N HCl. The precipitate was filtered and collected to yield 4-(1,1,4-trioxo-[1,2,5]thiadiazolidin-2-ylmethyl)-benzoic acid (85 mg). $^1$H-NMR (DMSO-d): 7.90 (d, J=8 Hz, 2H), 7.46 (d, J=8.4 Hz, 2H), 4.27-4.22 (br, 2H).

Example 10

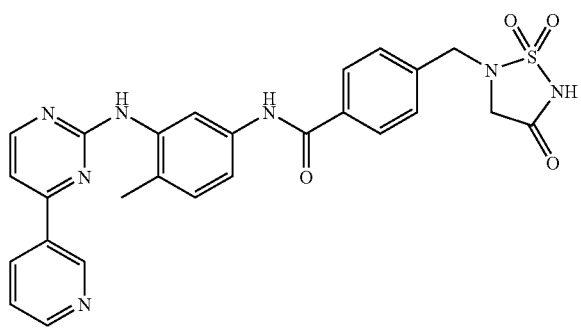

The title compound was prepared following the procedure of Example 1 utilizing Example R and Reagent FF to yield N-[4-methyl-3-(4-phenyl-pyrimidin-2-ylamino)-phenyl]-4-(1,1,4-trioxo-[1,2,5]thiadiazolidin-2-ylmethyl)-benzamide (48% yield). $^1$H-NMR (DMSO) δ10.19 (s, 1H), 9.30 (s, 1H), 9.00 (d, 1H), 8.72 (d, J=5.2 Hz, 2H), 8.59 (d, J=9.2 Hz, 1H), 8.52 (d, J=5.2 Hz, 2H), 8.08 (s, 1H), 7.92 (d, J=8.4 Hz, 1H), 7.62 (m, 1H), 7.50-7.43 (m, 4H), 7.19(d, J=8.4 Hz, 2H), 4.27(s, 2H), 3.86 (s, 2H), 2.20 (s, 3H). MS (ESI) m/e: 530.1(M+1).

Example 11

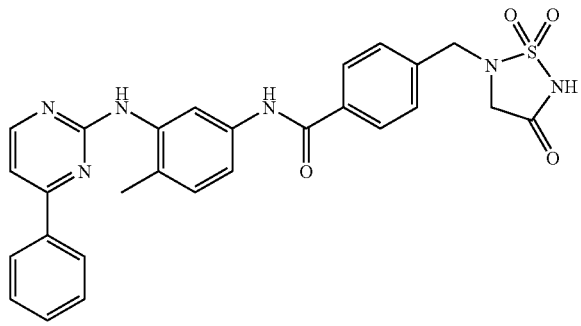

The title compound was prepared following the procedure of Example 1 utilizing Example R and Reagent AA to yield N-[4-methyl-3-(4-phenyl-pyrimidin-2-ylamino)-phenyl]-4-(1,1,4-trioxo-[1,2,5]thiadiazolidin-2-ylmethyl)-benzamide (56% yield). $^1$H-NMR (DMSO-d): 10.18 (s, 1H), 8 89 (s, 1H), 8.44 (d, J=4.8 Hz 1H), 8.12 (d, J=7.6 Hz, 2H), 8.05 (s, 1H), 7.92 (d, J=8.0 Hz, 2H), 7.50-7.44 (m, 6H), 7.33 (d, J=5.2 Hz, 1H), 7.18 (d, J=8.4 Hz, 1H), 4.28 (s, 2H), 3.81 (s, 2H), 2.20 (s, 3H). MS (ESI) m/e: 529.1 (M+1).

Example S

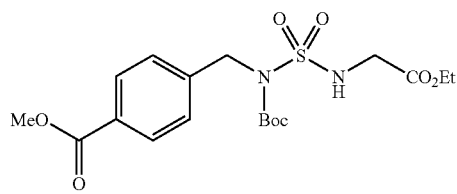

A solution of Reagent GG (10 g, 35.4 m mol) and diisopropyl azodicarboxylate (7.2 g, 35.4 mmol) in THF (60 mL) was added dropwise (15 min, 5° C.) to a solution of equal molar quantities of triphenylphosphine (9.3 g, 35.4 mmol) and 4-hydroxymethyl-benzoic acid methyl ester (6 g, 35.4 m mol) in THF (50 mL). The resulting mixture was stirred under $N_2$ atmosphere for 2 h. The solvent was removed and the residual was chromatographed to yield ethyl-[N-(N'-tert-butyloxycarbonyl,N'-benzoic methyl ester)-sulfamoyl]-glycinate as a white powder (8 g, 53.3% yield). $^1$H-NMR (CDCl$_3$): 7.99 (d, J=8.4 Hz, 2H), 7.42 (d, J=8.0 Hz, 2H), 5.80 (t, J=5.6 Hz, 1H), 4.85 (s, 2H), 4,12 (q, J=7.2 Hz, 2H), 3.90(s, 3H), 3.65 (d, J=5.6 Hz, 2H), 1.49 (s, 9H), 1.24 (t, 3H).

Example T

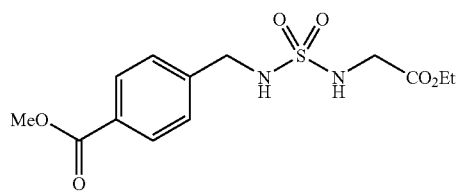

The solution of Example S (3 g, 7 m mol) in 2N HCl/dioxane 1,4-dioxane (60 mL) was heated to 50° C. for 15 min. Then the solvent was removed under reduced pressure to yield ethyl-[N-(N'-benzonic methyl ester)-sulfamoyl]-glycinate as a white solid (2 g, 86.9% yield).

$^1$H-NMR (CDCl$_3$): 8.01 (d, J=8.4, 2H), 7.41 (d, J=8.4, 2H), 4.86 (t, J=4.8 Hz, 1H), 4.70 (t, J=5.6 Hz, 1H), 4.32 (d, J=6.4 Hz, 2H), 4.21 (q, J=7.2 Hz, 2H), 3.91 (s, 3H), 3.82 (d, J=5.6 Hz, 2H), 1.28 (t, 3H).

Example U

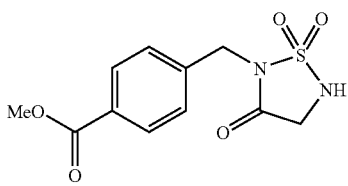

A solution of Example T (1 g, 30.3 mmol) and NaH (0.32 g, 78.7m mol) in THF (120 mL) was heated to reflux for 8 h. The mixture was cooled to RT, then quenched with 1N aq. HCl (100 mL) and extracted with CH$_2$Cl$_2$ (3×100 mL). The combined organic layers were dried (Na$_2$SO$_4$), and concentrated in vacuo and purified by flash chromatography to yield 4-(1,1,3-trioxo-[1,2,5]thiadiazolidin-2-ylmethyl)-benzoic acid methyl ester as a white powder (200 mg, 23% yield). $^1$H-NMR (CDCl$_3$) 8.02 (d, J=8.4, 2H), 7.48 (d, J=8.0 Hz, 2H), 5.02 (br s, 1H), 4.77 (s, 2H), 4.10 (d, J=7.2 Hz, 2H), 3.90 (s, 3H)

Example V

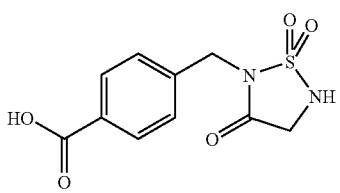

Example U (200 mg, 0.8 m mol) in THF (3 mL) and 2N aq. LiOH (1.5 mL) was stirred at RT for 3 h. The solvent was removed under reduced pressure, and the aqueous layer was acidified with 3N aq. HCl solution to yield 4-(1,1,3-trioxo6-[1,2,5]thiadiazolidin-2-ylmethyl)-benzoic acid a white powder (120 mg, 63%). $^1$H-NMR (DMSO-d): 7.90 (d, J=8.4 Hz, 2H), 7.43 (m, 2H), 4.10 (d, J=6.0 Hz, 2H), 3.56 (d, J=6.0 Hz, 2H).

Example 11

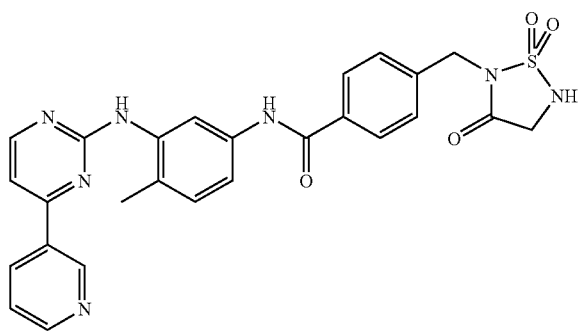

The title compound was prepared following the procedure of Example 1 utilizing Example V and Reagent FF to yield N-[4-methyl-3-(4-pyridin-3-yl-pyrimidin-2-ylamino)-phenyl]-4-(1,1,3-trioxo-[1,2,5]thiadiazolidin-2-ylmethyl)-benzamide (65% yield). $^1$H-NMR (DMSO-d): 10.19 (s, 1H), 9.27 (s, 1H), 8.97 (s, 1H), 8.69 (d, J=4.8 Hz, 2H), 8.60 (d, J=6.4 Hz, 2H), 8.52 (m, 1H), 8.06 (s, 1H), 7.89 (d, J=7.6 Hz, 5H), 7.55 (d, 1H), 7.47-7.41 (m, 4H), 7.18 (d, J=7.4 Hz, 2H), 4.76 (s, 2H), 4.15 (d, J=6.4 Hz, 2H), 2.20 (s, 3H); MS (ESI) m/e: 530.1 (M+1).

Example 12

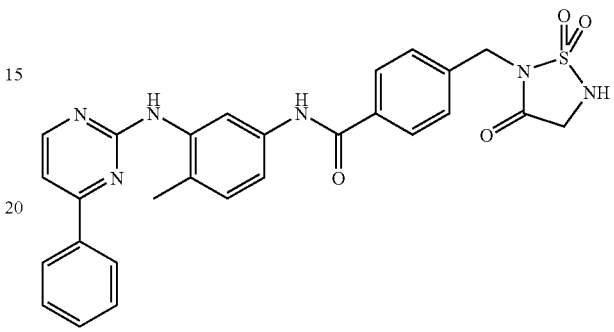

The title compound was prepared following the procedure of Example 1 utilizing Example V and Reagent AA to yield N-[4-Methyl-3-(4-phenyl-pyrimidin-2-ylamino)-phenyl]-4-(1,1,3-trioxo-[1,2,5]thiadiazolidin-2-ylmethyl)-benzamide (67% yield). $^1$H-NMR (DMSO): 10.18 (s, 1H), 8.85 (s, 1H), 8.61 (m, 1H), 8.43 (d, J=5.2 Hz, 2H), 8.10 (d, J=6.2 Hz, 2H), 8.04 (s, 1H), 7.90 (d, J=8.0 Hz, 2H), 7.4 (m, 5H), 7.32 (d, J=5.2 Hz, 1H), 7.18 (d, J=8 Hz, 1H), 7.05 (s, 1H), 6.93 (s, 1H), 4.76 (s, 2H), 4.16 (d, J=6.4 Hz, 2H); Ms (ESI) m/e: 529.1 (M+1)

Example W

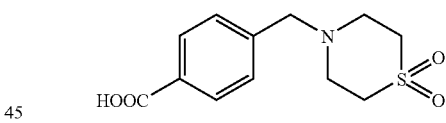

To a solution of 4-bromomethyl-benzic acid methyl ester (5.0 g, 0.02 mol) and 4-thiomorpholine (2.02 g, 0.02 mol) in acetonitrile (50 mL) was added K$_2$CO$_3$ (5.52 g, 0.04 mol). The mixture was stirred under reflux for two days. After filtration of inorganic salt and removal of solvent, the residue was added to colic. HCl. The mixture was stirred at RT for 30 min, concentrated, dissolved in acetic acid (30 mL) and 30% hydrogen peroxide (10 mL), stirred at 100° C. for overnight and then cooled to 0° C. Zinc powder (1.5 g) was added to the reaction solution. After being stirred for 30 min, the resulting mixture was filtered and solid was washed with MeOH. The filtrate was concentrated. The residue was neutralized by 2N solution of K$_2$CO$_3$ and adjust to PH=8-9. The solution was extracted with CH$_2$Cl$_2$ twice. The combined organic layers were dried over Mg$_2$SO$_4$, and concentrated. The residue was added conc. HCl (10 mL). The resulted solution was stirred at 80° C. for 2 h and concentrated to yield 4-(4,4-dioxothiomorpholinomethyl)benzoic acid (1.02 g, 18%). $^1$H NMR (D$_2$O) δ7.98 (d, J=8.0 Hz, 2H), 7.52 (d, J=8.0 Hz, 2H), 4.45 (s, 2H), 3.79 (s, 4H), 3.53 (s, 4H); MS (ESI) m/e: 270 (M$^+$+1).

Example 13

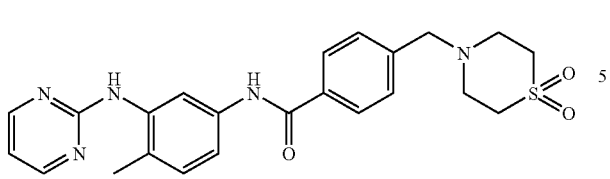

To a solution of Reagent BB (100 mg, 0.5 mmol) in the anhydrous DMF (3 mL) at RT was added Example W (200 mg, 0.77 mmol) followed by EDCI (200 mg, 1.20 mmol), HOBt (200 mg, 1.15 mmol) and NMM (0.5 mL). After being stirred at RT overnight, the mixture was added to $H_2O$ (100 mL) and extracted with $CH_2Cl_2$ (2×100 mL). The combined organic layers were washed with brine, dried ($Na_2SO_4$) and concentrated. The residue was purified by preparative HPLC to yield 4-(((4,4-dioxothiomorpholinomethyl)1)methyl)-N-(4-methyl-3-(pyrimidin-2-ylamino)phenyl)benzamide (100 mg, 44%). $^1H$ NMR (DMSO-d6): 8.43 (d, J=4.8 Hz, 2H), 8.29 (s, 1H), 7.86 (d, J=8.4 Hz, 2H), 7.81 (s, 1H), 7.46 (d, J=7.6 Hz, 3H), 7.21 (d, J=8.4 Hz, 2H), 6.75 (t, J=4.8 Hz, 1H), 3.72 (s, 2H), 3.10 (s, 4H), 3.03 (s, 4H), 2.32 (s, 3H); MS (ESI) m/e: 452 ($M^++1$).

Example 14

E-21

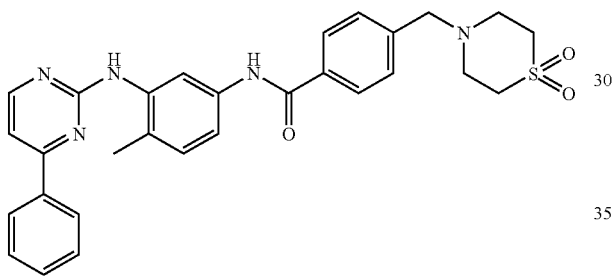

The title compound was prepared following the procedure of Example 13 utilizing Example W and Example AA to yield 4-(((4,4-dioxothiomorpholinomethyl)1)methyl)-N-(4-methyl-3-(4-phenylpyrimidin-2-ylamino)phenyl)benzamide. $^1H$ NMR (CDCl3): 8.54-8.52 (m, 2H), 8.49-8.11 (m, 2H), 7.88-7.83 (m, 2H), 7.80 (s, 1H), 7.50-7.39 (m, 6H), 7.23-7.15 (m, 2H), 7.02 (s, 1H), 3.73 (s, 2H), 3.12 (s, 4H), 3.01 (s, 4H), 2.38 (s, 3H); MS (ESI) m/e: 528 ($M^++1$).

Example 15

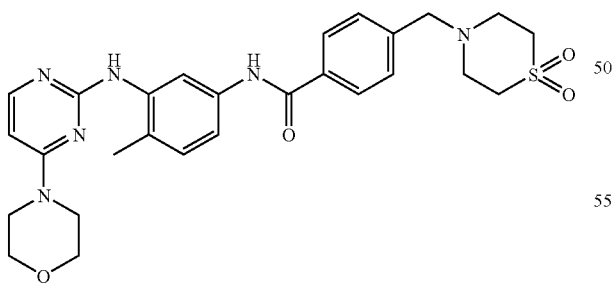

The title compound was prepared following the procedure of Example 13 utilizing Example W and Example HH to yield 4-(((4,4-dioxothiomorpholinomethyl)1)methyl)-N-(4-methyl-3-(4-morpholinopyrimidin-2-ylamino)phenyl)benzamide. $^1H$ NMR (CDCl3): 8.63 (s, 1H), 8.00 (d, J=6.0 Hz, 1H), 7.82 (d, J=8.0 Hz, 2H), 7.77 (s, 1H), 7.43 (d, J=8.4 Hz, 2H), 7.16-7.09 (m, 2H), 6.72 (s, 1H), 6.02 (d, J=6.4 Hz, 1H), 3.80-3.77 (m, 4H), 3.66 (s, 2H), 3.58 (s, 4H), 3.07 (s, 4H), 3.00-2.88 (m, 4H), 2.30 (s, 3H); MS (ESI) m/e: 537 ($M^++1$).

Example X

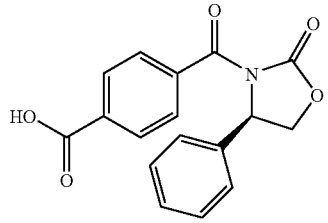

To a solution of D-4-phenyl-oxazolidin-2-one (1 g, 6 mmol) in anhydrous THF (40 mL) under nitrogen protection at −78° C. was added BuLi (2.5 M in hexane, 1.8 mL, 4.5 mmol). After one hour, the mixture was transferred to a solution of terephthalic acid chloride monobenzyl ester (prepared from Reagent DD (1.2 g, 4.5 mmol) and thionyl chloride (10 mL) at reflux for 2 h), in anhydrous THF. After being stirred at −78° C. for 30 min, the reaction mixture was warmed to RT for 2 h. After being quenched by adding saturate solution of ammonium chloride (1 mL), the reaction solution was extracted with $CH_2Cl_2$ (3×50 mL). The combined organic layers were dried ($Na_2SO_4$) and concentrated. The residue was dissolved in MeOH (20 mL) and 5% Pd/C (0.1 g) and stirred under 1 atm $H_2$ for 5 h. The suspension was filtered and filtrate was concentrated to yield D-4-(2-oxo-4-phenyl-oxazolidine-3-carbonyl)-benzoic acid (0.65 g, 46%). $^1H$ NMR (CDCl3): 8.15-8.11 (m, 2H), 7.70 (dd, J=6.8, 1.6 Hz, 2H), 7.44-7.33 (m, 5H), 5.63 (dd, J=8.8, 6.8 Hz, 1H), 4.78 (dd, J=18, 9.2 Hz, 1H), 4.36 (dd, J=9.2, 6.8 Hz, 1H); MS (ESI) m/e: 312 ($M^++1$).

Example Y

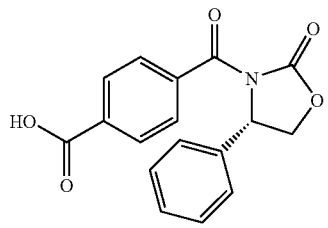

The title compound was prepared following the procedure of Example X utilizing L-4-phenyl-oxazolidin-2-one to yield L-4-(2-oxo4-phenyl-oxazolidine-3-carbonyl)-benzoic acid (0.65 g, 46%). $^1H$ NMR (CDCl3): 8.15-8.11 (m, 2H), 7.70 (dd, J=6.8, 1.6 Hz, 2H), 7.44-7.33 (m, 5H), 5.63 (dd, J=8.8, 6.8 Hz, 1H), 4.78 (dd, J=18, 9.2 Hz, 1H), 4.36 (dd, J=9.2, 6.8 Hz, 1H); MS (ESI) m/e: 312 ($M^++1$).

Example 16

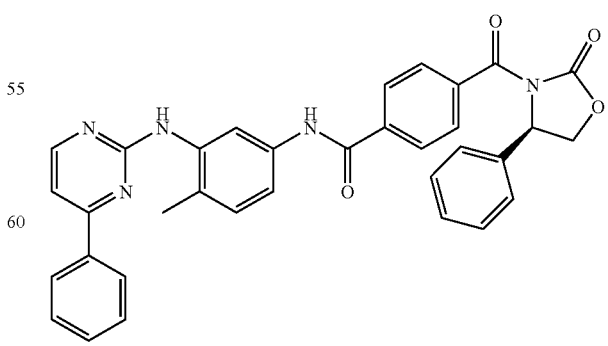

The title compound was prepared following the procedure of Example 13 utilizing Example X and Reagent AA to yield D-4-(2-oxo-4-phenyl-oxazolidine-3-carbonyl)-N-(4-methyl-3-(4-phenylpyrimidin-2-ylamino)phenyl)benzamide.
$^1$H NMR (DMSO-d6): 10.34 (s, 1H), 8.87 (s, 1H), 8.44 (d, J=5.2 Hz, 1H), 8.12-8.10 (m, 2H), 7.96 (d, J=8.4 Hz, 2H), 7.84 (d, J=8.4 Hz, 2H), 7.54-7.30 (m, 8H), 7.19 (d, J=8.4 Hz, 1H), 5.63 (dd, J=8.0 & 8.0, 1H), 4.84 (t, J=8.0, 1H), 4.23 (dd, J=8.0 & 8.0, 1H), 2.21 (s. 3H). MS (ESI) m/e: 570 (M$^+$+1)

Example 17

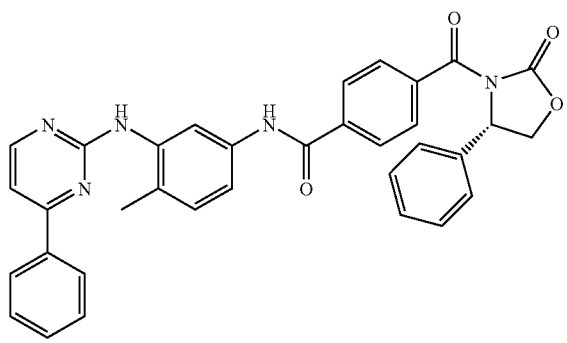

The title compound was prepared following the procedure of Example 13 utilizing Example Y and Reagent AA to yield L-4-(2-oxo-4-phenyl-oxazolidine-3-carbonyl)-N-(4-methyl-3-(4-phenylpyrimidin-2-ylamino)phenyl)benzamide. $^1$H NMR (DMSO-d6): 10.34 (s, 1H), 8.87 (s, 1H), 8.44 (d, J=5.2 Hz, 1H), 8.12-8.10 (m, 2H), 7.96 (d, J=8.4 Hz, 2H), 7.84 (d, J=8.4 Hz, 2H), 7.54-7.30 (m, 8H), 7.19 (d, J=8.4 Hz, 1H), 5.63 (dd, J=8.0 & 8.0, 1H), 4.84 (t, J=8.0, 1H), 4.23 (dd, J=8.0 & 8.0, 1H), 2.21 (s. 3H). MS (ESI) m/e: 570 (M$^+$+1)

Example 18

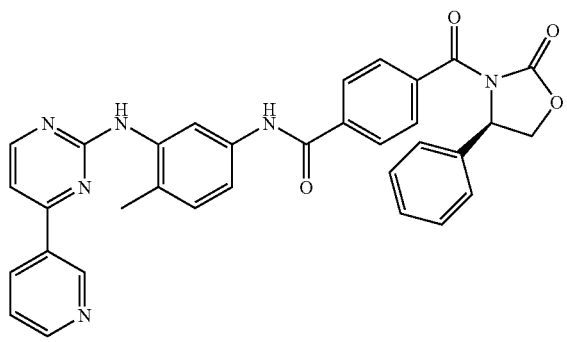

The title compound was prepared following the procedure of Example 13 utilizing Example X and Reagent FF to yield D-4-(2-oxo-4-phenyl-oxazolidine-3-carbonyl)-N-[4-methyl-3-(4-pyridin-3-yl-pyrimidin-2-ylamino)-phenyl]benzamide. $^1$H NMR (DMSO-d$_6$): 10.34 (s, 1H), 8.95 (s, 1H), 8.66 (m, 1H), 8.48 (m, 2H), 8.07 (s, 1H), 7.96 (d, J=8.4 Hz, 2H), 7.84 (d, J=8.0 Hz, 2H), 7.58-7.42 (m, 4H), 7.41-7.36 (m, 3H), 7.32 (d, J=6.8 Hz, 1H), 7.20 (d, J=8.4 Hz, 1H), 5.63 (t, J=7.6 Hz, 1H), 4.84 (t, J=7.6 Hz, 1H), 4.23 (t, J=7.6 Hz, 1H), 2.21 (s, 3H).; MS (ESI) m/e: 571 (M$^+$+1).

Example 19

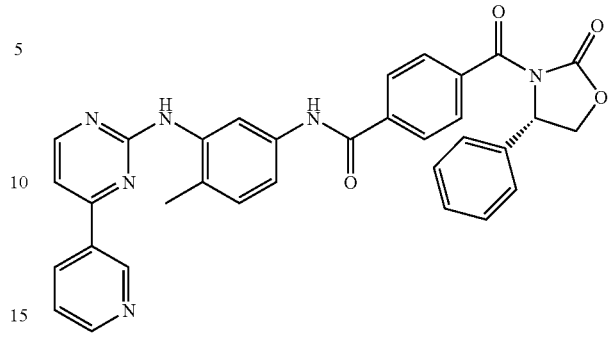

The title compound was prepared following the procedure of Example 13 utilizing Example Y and Reagent FF to yield L-4-(2-oxo-4-phenyl-oxazolidine-3-carbonyl)-N-[4-methyl-3-(4-pyridin-3-yl-pyrimidin-2-ylamino)-phenyl]benzamide.
$^1$H NMR (DMSO-d$_6$): 10.34 (s, 1H), 8.95 (s, 1H), 8.66 (m, 1H), 8.48 (m, 2H), 8.07 (s, 1H), 7.96 (d, J=8.4 Hz, 2H), 7.84 (d, J=8.0 Hz, 2H), 7.58-7.42 (m, 4H), 7.41-7.36 (m, 3H), 7.32 (d, J=6.8 Hz, 1H), 7.20 (d, J=8.4 Hz, 1H), 5.63 (t, J=7.6 Hz, 1H), 4.84 (t, J=7.6 Hz, 1H), 4.22 (t, J=7.6 Hz, 1H), 2.21 (s, 3H).); MS (ESI) m/e: 571 (M$^+$+1).

Example Z

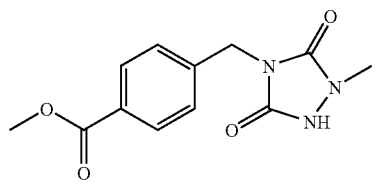

To a solution of 1-methyl-[1,2,4]triazolidine-3,5-dione (1.886 g, 0.0164 mol) and sodium hyhride (200 mg) in DMSO (5 mL) was added 4-chloromethyl-benzoic acid methyl ester (1.0 g, 0.0054 mol). The mixture was stirred at RT for overnight, quenched with H$_2$O (100 mL), and extracted by CH$_2$Cl$_2$. The organic layer was washed with H$_2$O, dried (Na$_2$SO$_4$) and concentrated in vacuo to yield methyl 4-((1-methyl-3,5-dioxo-1,2,4-triazolidin4-yl)methyl)benzoate (1.02 g, 72%). $^1$H NMR (CDCl$_3$): 7.93 (d, J=8.4 Hz, 2H), 7.27 (d, J=8.4 Hz, 2H), 4.68 (s, 2H), 3.83 (s, 3H), 3.27 (s, 3H). MS (ESI) m/e: 264 (M$^+$+1)

Example AA

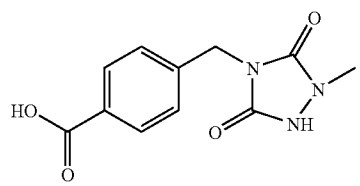

A solution of Example Z (1.0 g, 0.0038 mol) and lithium hydroxide (0.950 g) in MeOH (10 mL) was stirred at RT for overnight. The mixture was acidified by 2N HCl to pH=5-6 and extracted by CH$_2$Cl$_2$ (3×50 mL). The combined organic layers were washed with H$_2$O, dried (MgSO$_4$) and concentrated in vacuo to yield 4-((1-methyl-3,5-dioxo-1,2,4-triazolidin-4-yl)methyl)benzoic acid (0.6 g, 64%). $^1$H NMR (CDCl$_3$): 7.71 (d, J=8.4 Hz, 2H), 7.17 (d, J=8.4 Hz, 2H), 4.68 (s, 2H), 2.90 (s, 3H), 2.6 (s, 3H); MS (ESI) m/e: 249 (M$^+$1).

Example 20

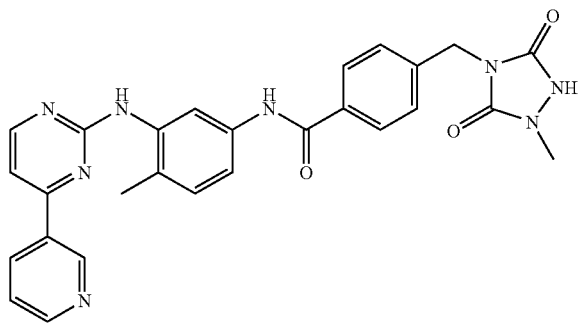

The title temperature was prepared following the procedure of Example 1 utilizing Example AA and Reagent FF to yield N-(3-(4-(pyridin-3-yl)pyrimidin-2-ylamino)-4-methylphenyl)-4-((1-methyl-3,5-dioxo-1,2,4-triazolidin-4-yl)methyl)benzamide. $^1$H NMR (CD$_{3OD}$) δ 9.44 (s, 1H), 8.79 (d, J=8.0 Hz, 2H), 8.50 (d, J=4.0 Hz, 1H), 8.25 (s, 1H), 7.93 (d, J=8.0 Hz, 2H), 7.73 (s, 1H), 7.46 (d, J=8.0 Hz, 2H), 7.40 (d, J=5.2 Hz, 1H), 7.35 (d, J=8.4 Hz, 1H), 7.25 (d, J=8.4 Hz, 1H), 4.87 (s, 2H), 3.07 (s, 3H), 2.31 (s, 3H). MS (ESI) m/e: 509(M$^+$+1).

Example 20

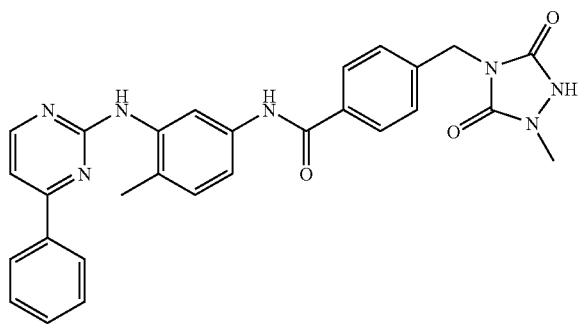

The title temperature was prepared following the procedure of Example 1utilizing Example AA and Reagent AA to yield N-(3-(4-phenylpyrimidin-2-ylamino)-4-methylphenyl)-4-((1-methyl-3,5-dioxo-1,2,4-triazolidin-4-yl)methyl)benzamide. $^1$H NMR (CD$_3$OD): 8.39 (s, 1H), 8.20 (d, J=1.6 Hz, 1H), 8.13 (m, 2H), 7.93 (d, J=8.4 Hz, 2H), 7.47 (m, 6H), 7.27 (m, 2H), 4.59 (s, 2H), 3.08 (s, 3H), 2.31 (s, 3H). MS (ESI) m/e: 508 (M$^+$+1).

Example 21

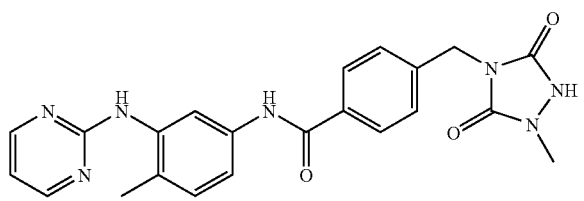

The title temperature was prepared following the procedure of Example 1 utilizing Example AA and Reagent BB to yield 4-((1-methyl-3,5-dioxo-1,2,4-triazolidin-4-yl)methyl)-N-(4-methyl-3-(pyrimidin-2-ylamino)phenyl)benzamide. $^1$H NMR (CDCl$_3$): 11.31 (s, 1H), 10.15 (s, 1H), 8.77 (s, 1H), 8.33 (m, 2H), 7.87 (m, 3H), 7.40 (m, 3H), 7.14 (d, J=8.4 Hz, 1H), 6.71 (m, 1H), 4.73 (s, 2H), 2.97 (s, 3H), 2.14 (s, 3H); MS (ESI) m/e: 432 (M$^+$+1).

Example BB

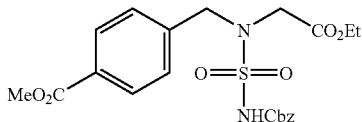

To a stirred solution of chlorosulfonyl isocyanate (2.2 g, 15.2 mmol) in CH$_2$Cl$_2$ (40 mL) was added benzyl alcohol (1.64 g, 15.2 mmol) at 0° C. After being stirred for 1 h, a solution of Example N (4.2 g, 16.7 mmol) and triethylamine (6 mL, 4. 3 g, 42.6 mmol) in CH2Cl2 (40 mL) was added at a rate so that the reaction temperature did not rise above 5° C. When the addition was completed, the reaction solution was allowed to warm to RT and stirred overnight. The reaction mixture was then poured into 1 N HCl saturated with NaCl (300 mL). The organic layer was separated and the aqueous layer extracted with CH$_2$Cl$_2$. The combined organic layers were dried over Na$_2$SO$_4$, and concentrated to yield the crude compound. Recrystallization from CH$_2$Cl$_2$/n-hexane yielded Example BB (5.9 g, 76.6% yield). $^1$H-NMR (CDCl3) δ 8.00 (d, J=8.4 Hz, 2H), 7.87 (s, 1H), 7.36 (m, 5H), 5.29 (s, 2H), 4.65 (s, 2H), 4.15 (q, J=7.2 Hz, 2H), 3.98 (s, 2H), 3.92 (s, 3H), 1.24 (t, 3H).

Example CC

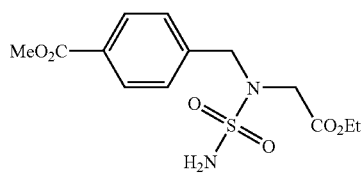

To a solution of Example BB (5.5 g, 118 mmol) in MeOH (50 mL) and EtOAc (50 mL) was added 10% Pd/C (0.8 g ) under nitrogen atmosphere. Then the result mixture was stirred at ambient temperature under H$_2$ (60 psi) overnight. The solvent was removed to yield Example CC (3.4 g, 85%) as a white solid. $^1$H-NMR (CDCl$_3$, δ) 8.02 (d, J=8.4 Hz, 2H), 7.41 (d, J=8.4 Hz, 2H), 5.20 (s, 2H), 4.44 (s, 2H), 4.19 (q, J=7.2 Hz, 2H), 3.91 (s, 3H), 3.90 (s, 2H), 1.25 (t, J=7.2 Hz, 3H)

Example DD

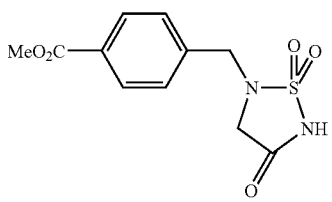

A NaOMe solution was first prepared by adding NaH (60%, dispersion in mineral oil, 43.5 mg, 1.1 mmol) to MeOH (30 mL). Example CC (300 mg, 0.9 mmol) was added to the NaOMe-MeOH solution and the reaction was stirred at RT overnight. The solution was concentrated to dryness in vacuum and the residue was dissolved in $H_2O$ (30 mL). The aqueous solution was acidified with 3 N HCl (aq.) and the result precipitate was filtered and collected to yield Example DD (120 mg, 40% yield). $^1$H-NMR (DMSO-$d_6$) 7.92 (d, J=8.4 Hz, 2H), 7.49 (d, J=8.4 Hz, 2H), 4.35 (s, 2H), 3.99 (s, 2H), 3.83 (s, 3H).

Example EE

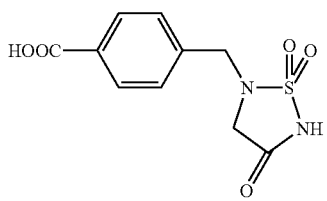

The solution of Example DD (100 mg, 0.35 mmol) in THF (4 mL) and 1.5 mL of 2 N aq. LiOH solution was stirred at RT for 3 h. Then the solvent was removed under reduced pressure and the residue was dissolved in water (20 mL) and acidified with aqueous 3 N HCl. The result precipitate was filtered to yield Example EE (85 mg). $^1$H-NMR (DMSO-d) δ 7.90 (d, J=8 Hz, 2H), 7.46 (d, J=8.4 Hz, 2H), 4.27-4.22 (br, 2H).

Example 22

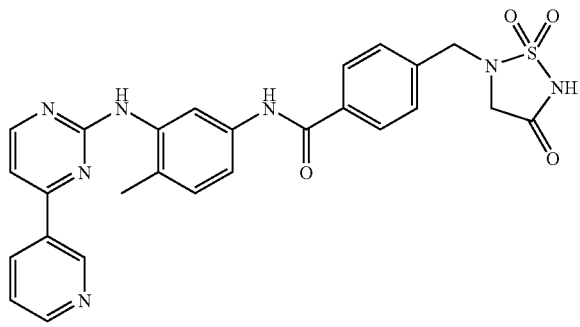

The title compound was prepared following the procedure of Example 1 utilizing Example EE and Reagent FF to yield Example 22. $^1$H-NMR (DMSO-$d_6$) δ10.19 (s, 1H), 9.30 (s, 1H), 9.00 (d, 1H), 8.72 (d, J=5.2 Hz, 2H), 8.59 (d, J=9.2 Hz, 1H), 8.52 (d, J=5.2 Hz, 2H), 8.08 (s, 1H), 7.92 (d, J=8.4 Hz, 1H), 7.62 (m, 1H), 7.50-7.43 (m, 4H), 7.19 (d, J=8.4 Hz, 2H), 4.27 (s, 2H), 3.86 (s, 2H), 2.20 (s, 3H). MS (ESI) m/e: 530 ($M^+$+1).

Example 23

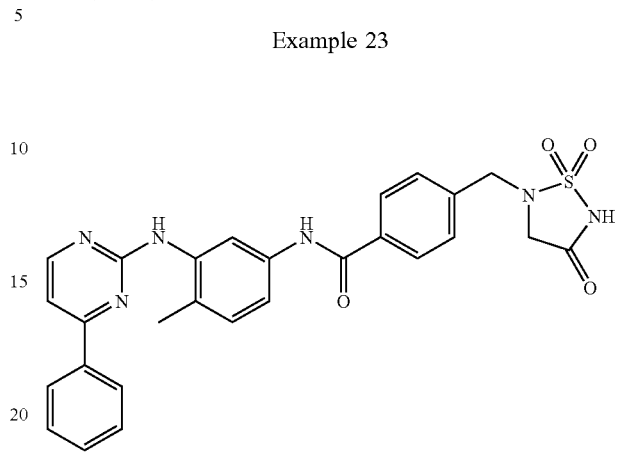

The title compound was prepared following the procedure of Example 1 utilizing Example EE and Reagent AA to yield Example 22. $^1$H NMR (DMSO-$d_6$) δ10.18 (s, 1H), 8 89 (s, 1H), 8.44 (d, J=4.8 Hz 1H), 8.12 (d, J=7.6 Hz, 2H), 8.05 (s, 1H), 7.92 (d, J=8.0 Hz, 2H), 7.50-7.44 (m, 6H), 7.33 (d, J=5.2 Hz, 1H), 7.18 (d, J=8.4 Hz, 1H), 4.28 (s, 2H), 3.81 (s, 2H), 2.20 (s, 3H). MS (ESI) m/e: 529 ($M^+$+1).

Example FF

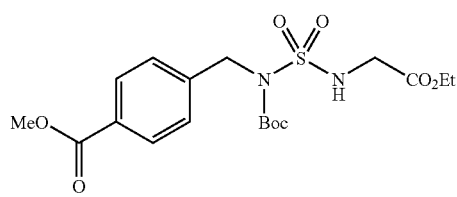

A solution of [Boc-sulfamide] amino ester (10 g, 35.4 m mol) min) to a solution of triphenylphosphine (9.3 g, 35.4 mmol) and 4-hydroxymethyl-benzoic acid methyl ester (6 g, 35.4 m mol) in THF (50 mL) at 0-5° C. The result mixture was stirred under $N_2$ for 2 h. The solvent was removed and the residual was purified by column chromatography to yield Example FF as a white powder (8 g, 53.3% yield). $^1$H-NMR (CDCl$_3$) 7.99 (d, J=8.4 Hz, 2H), 7.42 (d, J=8.0 Hz, 2H), 5.80 (t, J=5.6 Hz, 1H), 4.85 (s, 2H), 4.12 (q, J=7.2 Hz, 2H), 3.90 (s, 3H), 3.65 (d, J=5.6 Hz, 2H), 1.49 (s, 9H), 1.24 (t, 3H).

Example GG

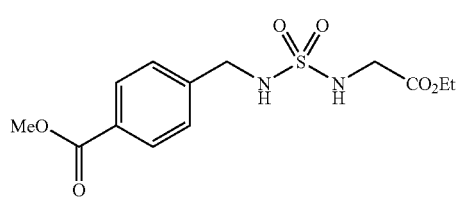

The solution of Example FF (3 g, 7 m mol) in 2N HCl/dioxane 1,4-dioxane (60 mL) was heated to 50° C. for 15 min. The solvent was removed in vacuo to yield Example GG as a white solid (2 g, 86.9% yield). ¹H-NMR (CDCl₃, δ) 8.01 (d, J=8.4, 2H), 7.41 (d, J=8.4, 2H), 4.86 (t, J=4.8 Hz, 1H), 4.70 (t, J=5.6 Hz, 1H), 4.32 (d, J=6.4 Hz, 2H), 4.21 (q, J=7.2 Hz, 2H), 3.91 (s, 3H), 3.82 (d, J=5.6 Hz, 2H), 1.28 (t, 3H).

Example HH

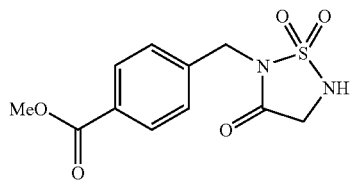

A solution of Example GG (1 g, 30.3 mmol) and NaH (0.32 g, 78.7m mol) in THF (120 mL) was heated to reflux for 8 h. The mixture was cool to RT, quenched with 1N aq. HCl solution (100 mL) and extracted with CH₂Cl₂ (3×100 mL). The combined organic phases were dried (Na₂SO₄), and concentrated in vacuo and purified by flash chromatography to yield Example HH as a white powder (200 mg, 23% yield). ¹H-NMR (CDCl₃, δ) 8.02 (d, J=8.4, 2H), 7.48 (d, J=8.0 Hz, 2H), 5.02 (br s, 1H), 4.77 (s, 2H), 4.10 (d, J=7.2 Hz, 2H), 3.90 (s, 3H)

Example 11

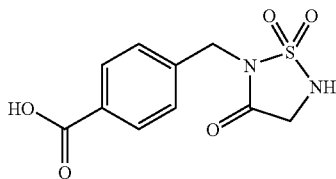

Example HH (200 mg, 0.8 m mol) was dissolved in THF (3 mL), and 1.5 mL solution of 2N aq. LiOH was added to the reaction solution. The mixture was stirred at RT for 3 h. The solvent was removed in vacuo, and the aqueous layer was acidified with 3N aq. HCl solution, and filtered to yield Example 11 as a white powder (120 mg, 63%). ¹H-NMR (DMSO-d) δ7.90 (d, J=8.4 Hz, 2H), 7.43 (m, 2H), 4.10 (d, J=6.0 Hz, 2H), 3.56 (d, J=6.0 Hz, 2H).

Example 24

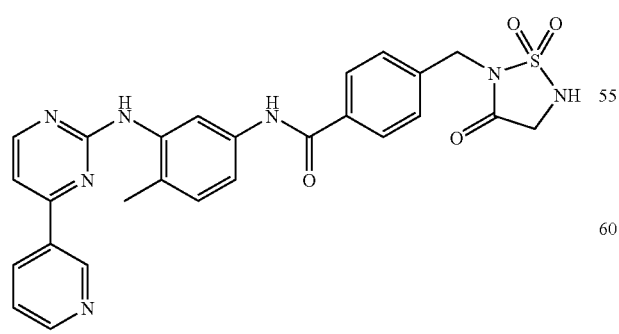

The title compound was prepared following the procedure of Example 1 utilizing Example II and Reagent FF (65% yield). ¹H-NMR (DMSO-d) δ10.19 (s, 1H), 9.27 (s, 1H), 8.97 (s, 1H), 8.69 (d, J=4.8 Hz, 2H), 8.60 (d, J=6.4 Hz, 2H), 8.52 (m, 1H), 8.06 (s, 1H), 7.89 (d, J=7.6 Hz, 5H), 7.55 (d, 1H), 7.47-7.41 (m, 4H), 7.18 (d, J=7.4 Hz, 2H), 4.76 (s, 2H), 4.15 (d, J=6.4 Hz, 2H), 2.20 (s, 3H); MS (ESI) m/e: 530 (M+1).

Example 25

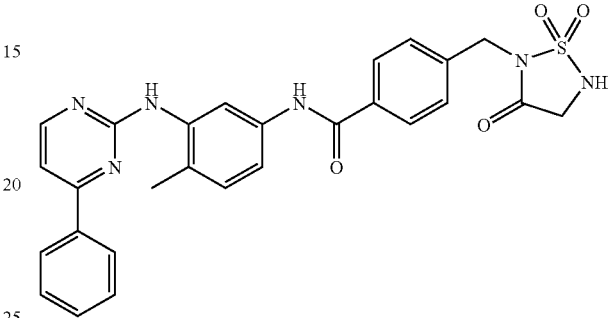

The title temperature was prepared following the procedure of Example 1 utilizing Example II and Reagent AA. (67% yield). ¹H-NMR (DMSO-d), δ10.18 (s, 1H), 8.85 (s, 1H), 8.61 ((m, 1H), 8.43 (d, J=5.2 Hz, 1H), 8.10 (d, J=6.2 Hz, 2H), 8.04 (s, 1H), 7.90 (d, J=8.0 Hz, 2H), 7.4 (m, 5H), 7.32 (d, J=5.2 Hz, 1H), 7.18 (d, J=8 Hz, 1H), 7.05 (s, 1H), 6.93 (s, 1H), 4.76 (s, 2H), 4.16 (d, J=6.4 Hz, 2H); Ms (ESI) m/e: 529 (M+1)

Specific embodiments are additionally illustrated below which are intended to represent more clearly, but without limitation to the generic scope, the present invention:

Example 1

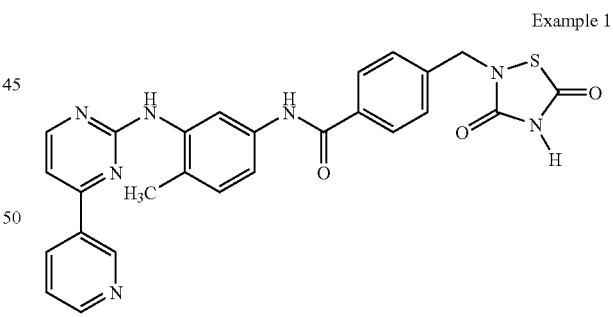

Example 2

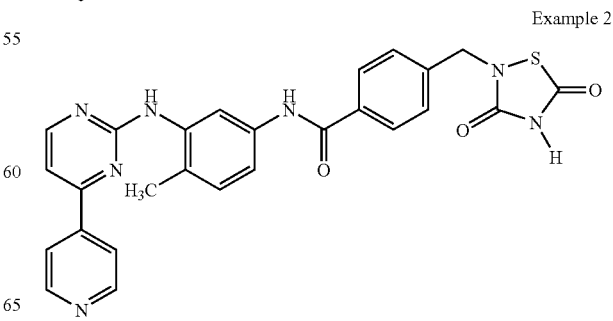

Example 3

Example 4

Example 5

Example 6

Example 7

Example 8

Example 9

Example 10

Example 11

Example 12

-continued
Example 13
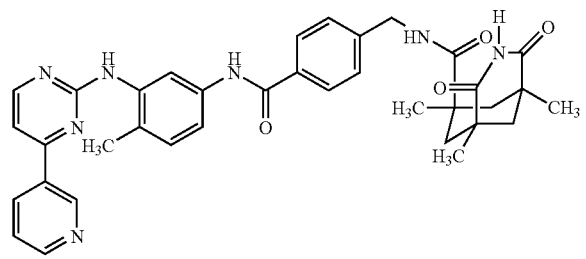
Example 14
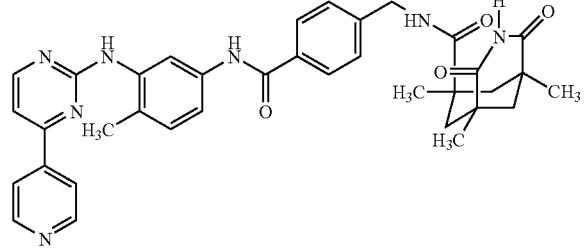
Example 15
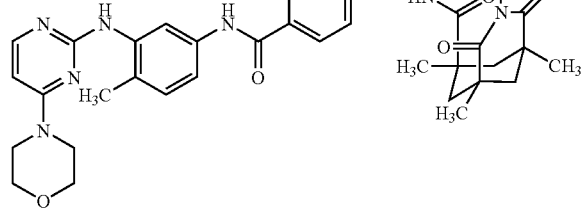
Example 16
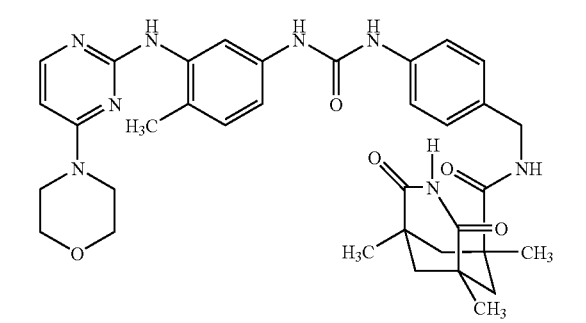
Example 17
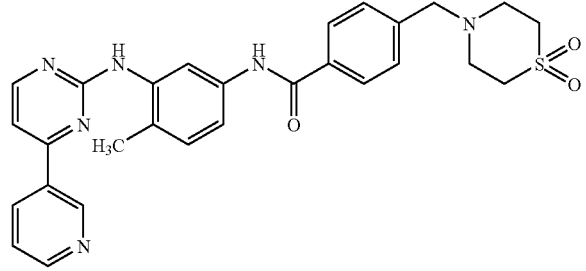
-continued
Example 18
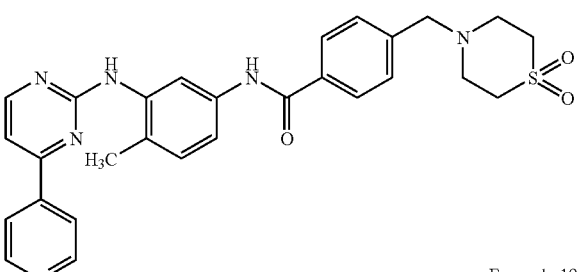
Example 19
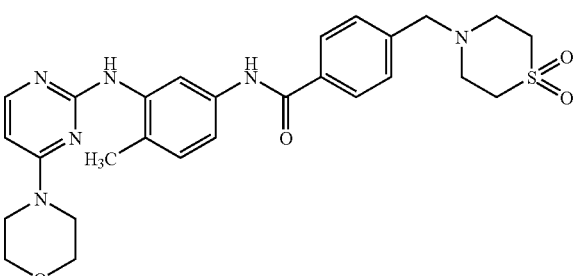
Example 20
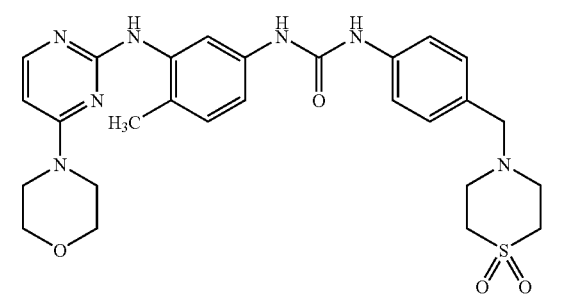
Example 21
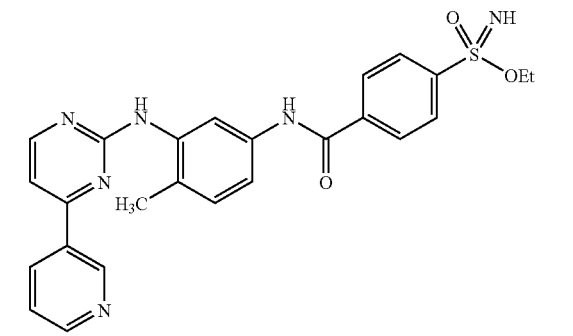
Example 22
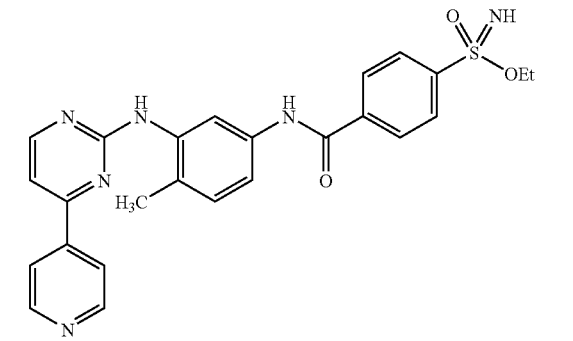

Example 23
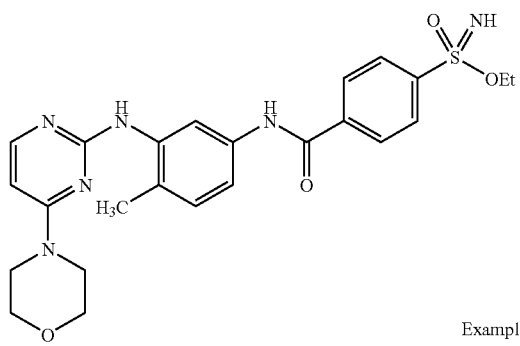
Example 24
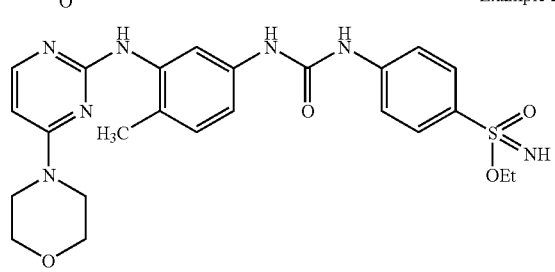
Example 25
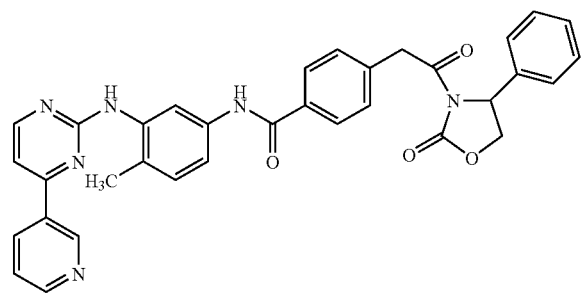
Example 26
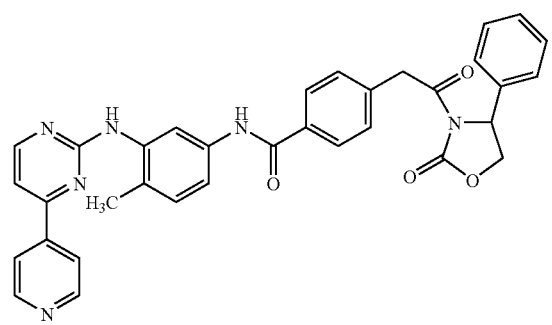
Example 27
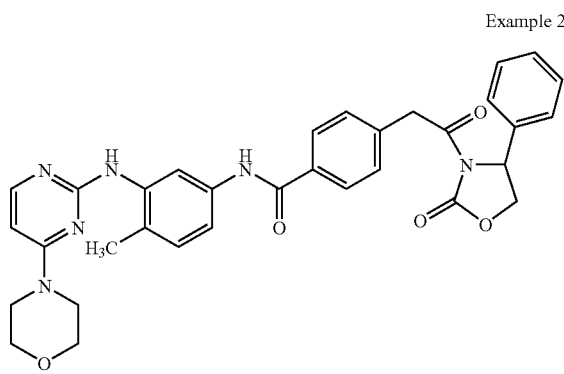
Example 28
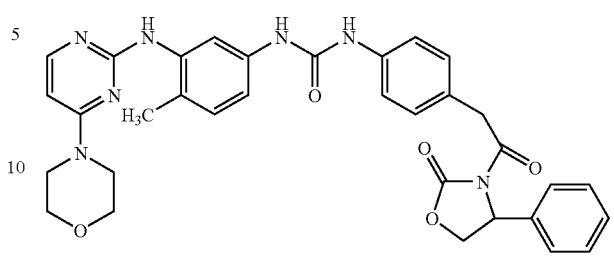
Example 29
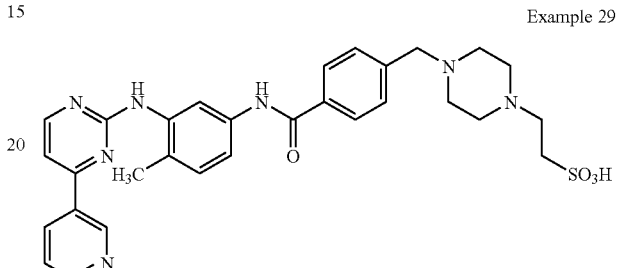
Example 30
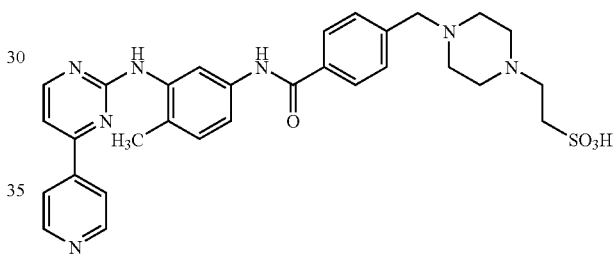
Example 31
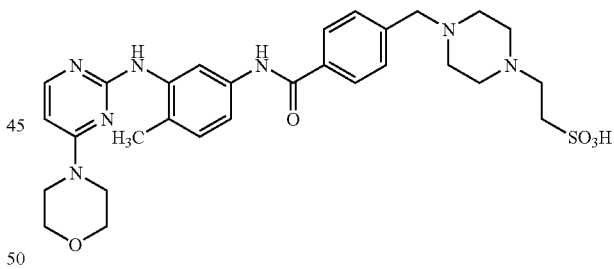
Example 32
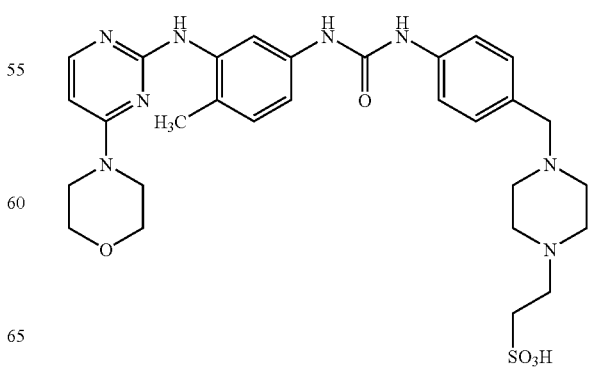

Example 33
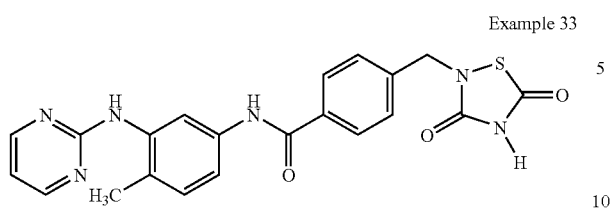
Example 34
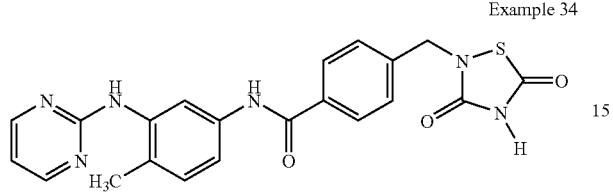
Example 35
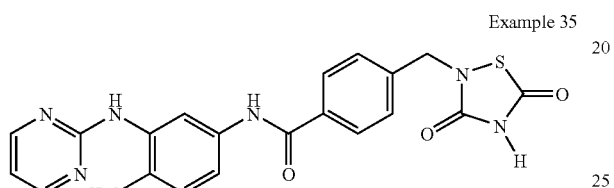
Example 36
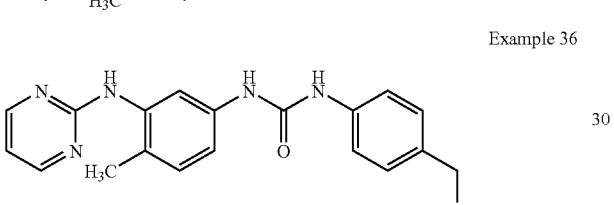
Example 37
Example 38
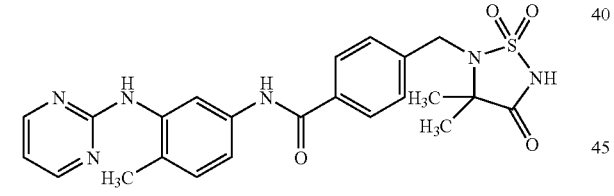
Example 39
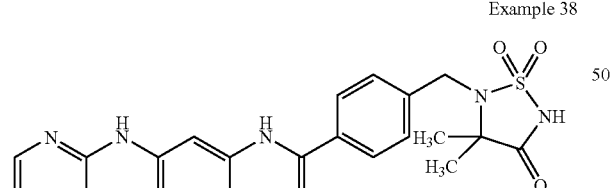
Example 40
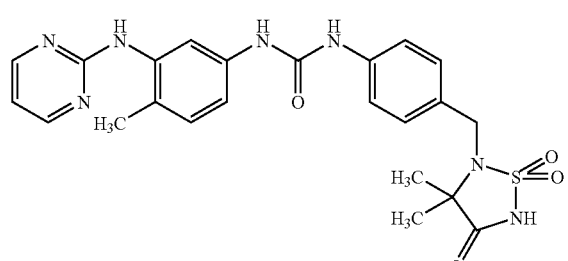
Example 41
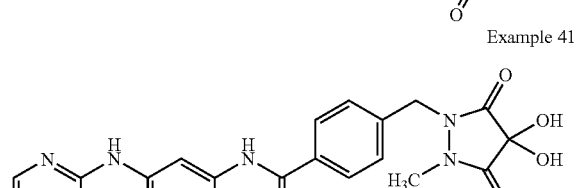
Example 42
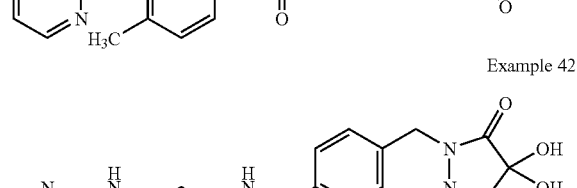
Example 43
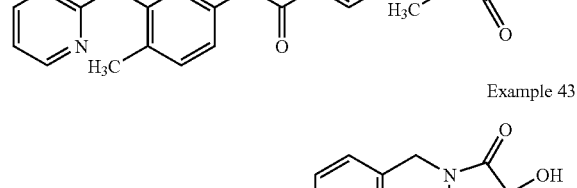
Example 44
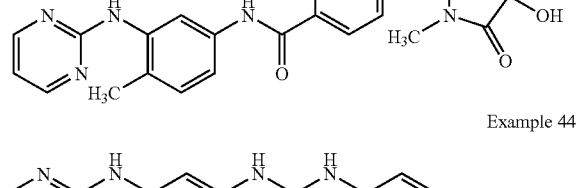
Example 45
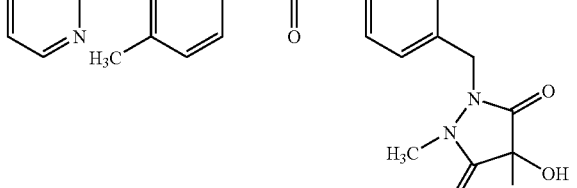
Example 46
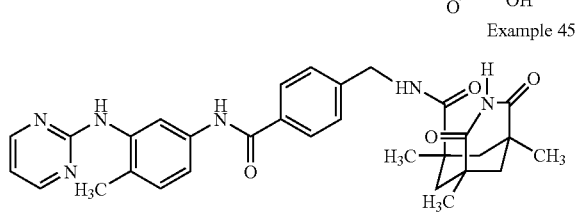

-continued

Example 47
Example 48
Example 49
Example 50
Example 51
Example 52
Example 53
Example 54
Example 55
Example 56
Example 57
Example 58
Example 59

-continued
Example 60
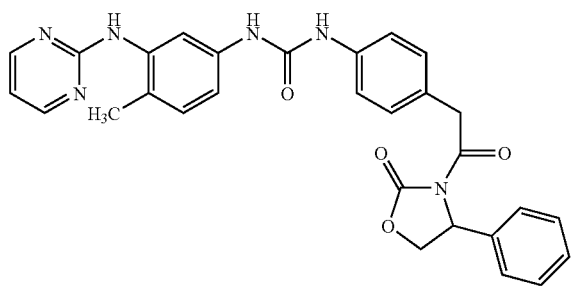
Example 61
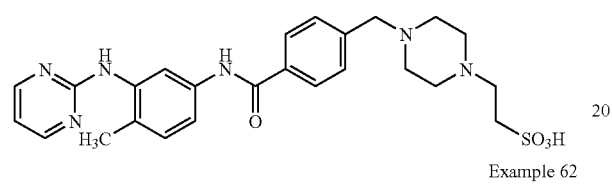
Example 62
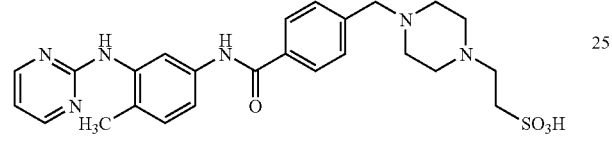
Example 63
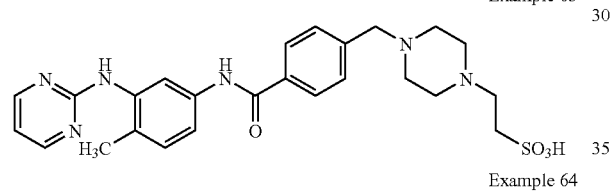
Example 64
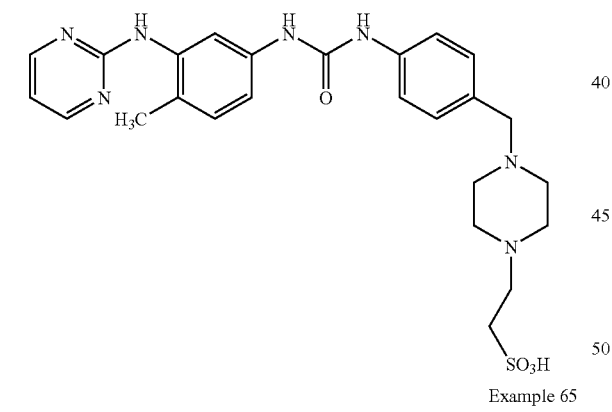
Example 65
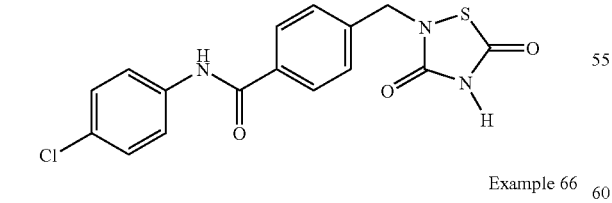
Example 66
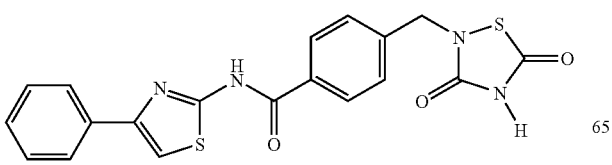
-continued
Example 67
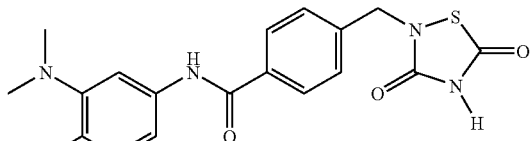
Example 68
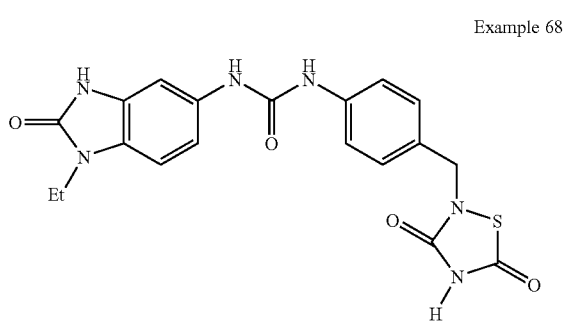
Example 69
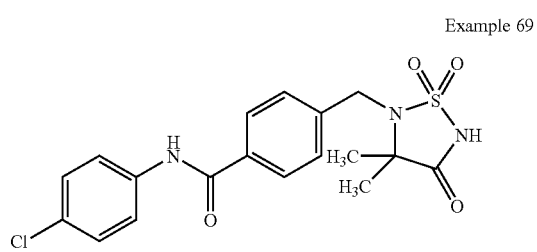
Example 70
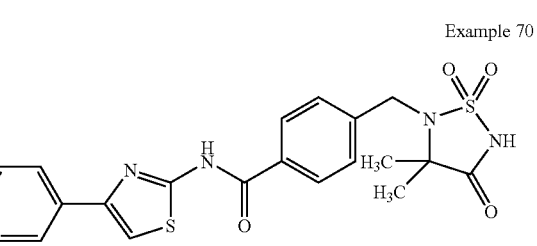
Example 71
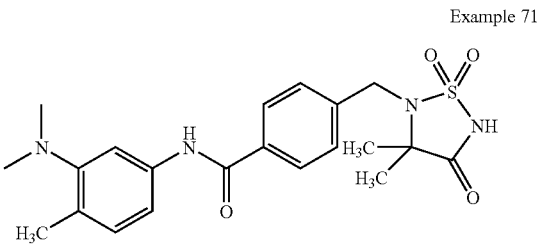
Example 72
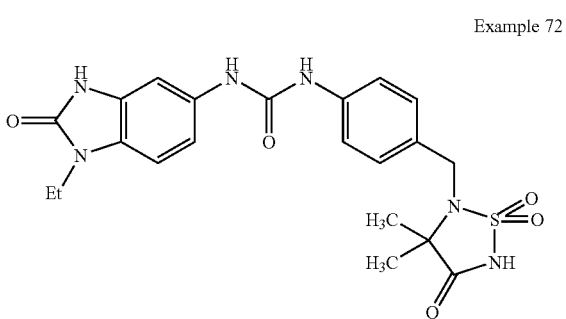

Example 73
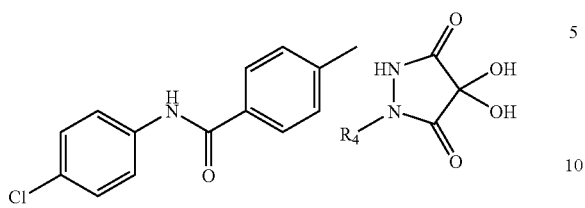
Example 74
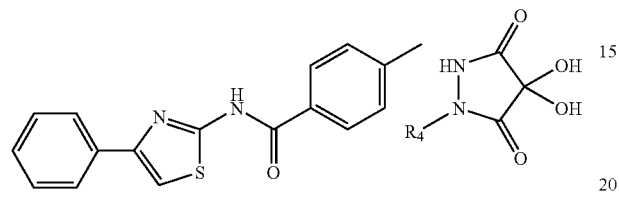
Example 75
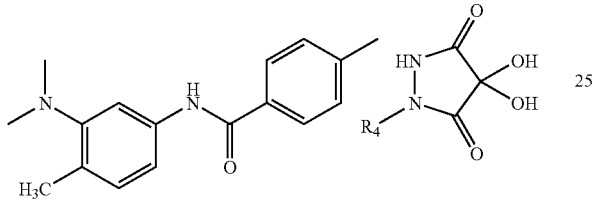
Example 76
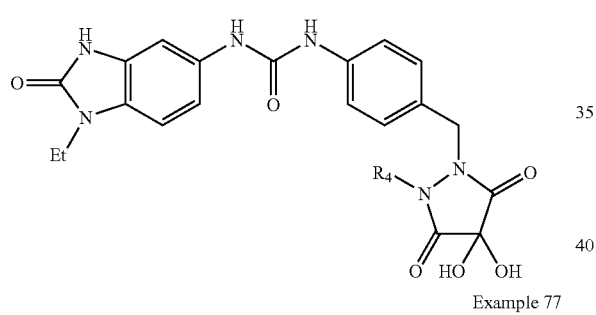
Example 77
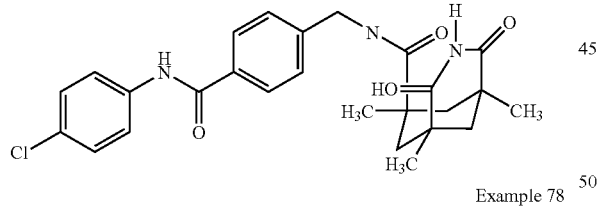
Example 78
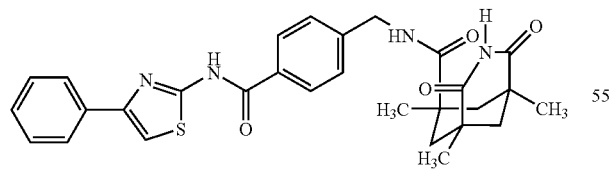
Example 79
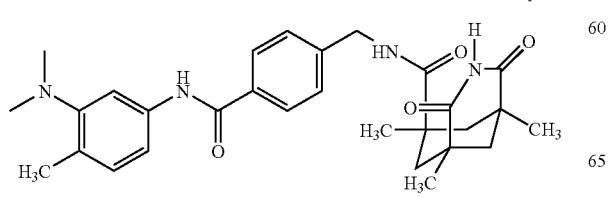
Example 80
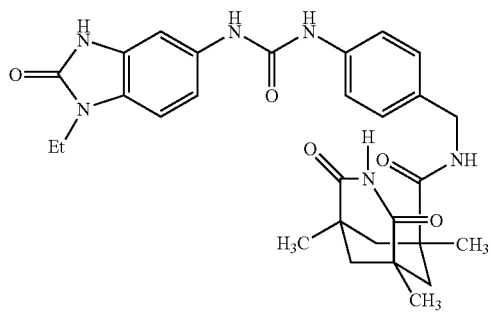
Example 81
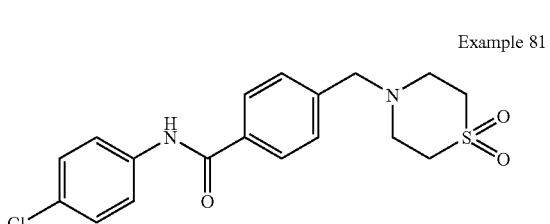
Example 82
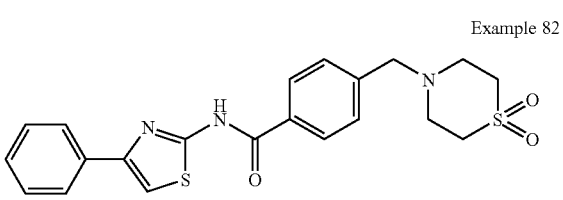
Example 83
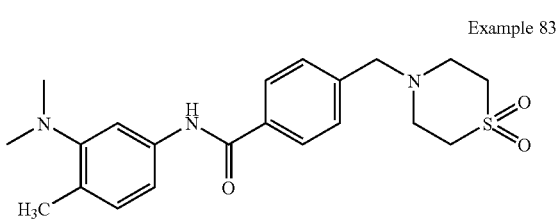
Example 84
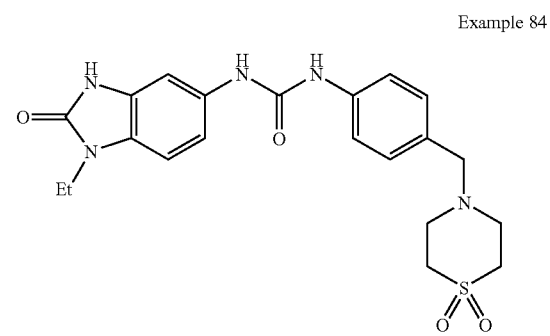
Example 85
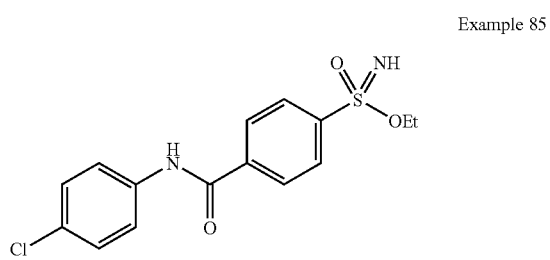

-continued

Example 86
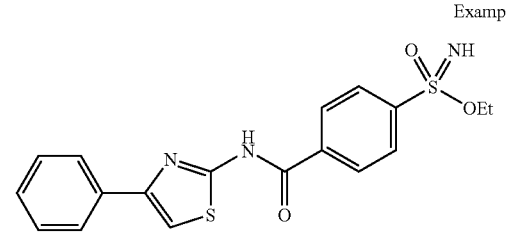

Example 87
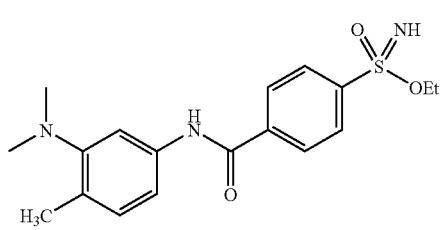

Example 88
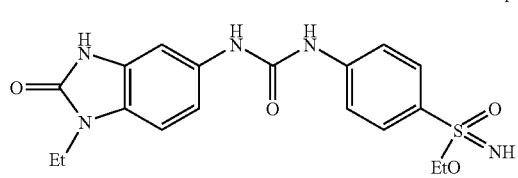

Example 89
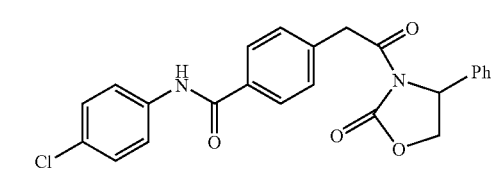

Example 90
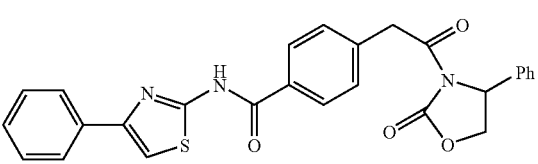

Example 91
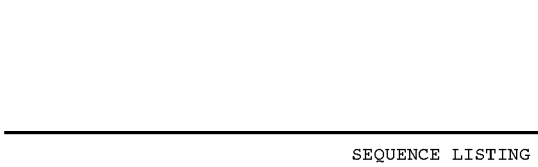

-continued

Example 92
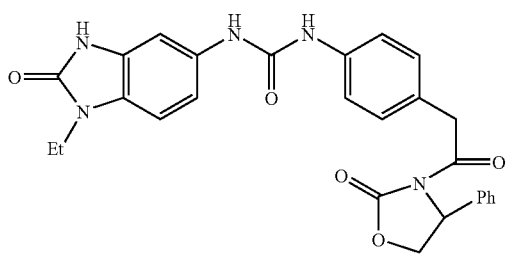

Example 93
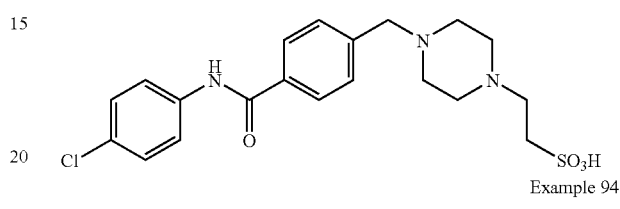

Example 94
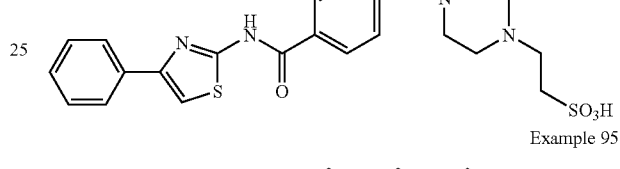

Example 95
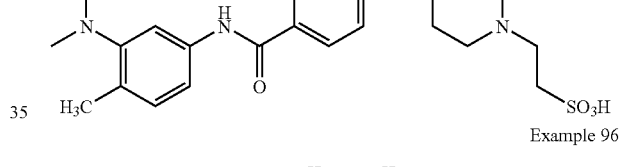

Example 96
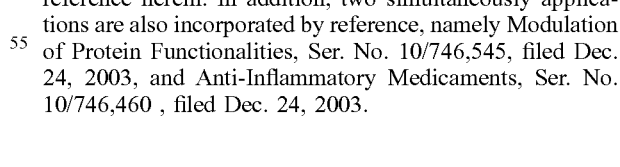

All of the references above identified are incorporated by reference herein. In addition, two simultaneously applications are also incorporated by reference, namely Modulation of Protein Functionalities, Ser. No. 10/746,545, filed Dec. 24, 2003, and Anti-Inflammatory Medicaments, Ser. No. 10/746,460, filed Dec. 24, 2003.

What is claimed is:

1. A compound of the formula

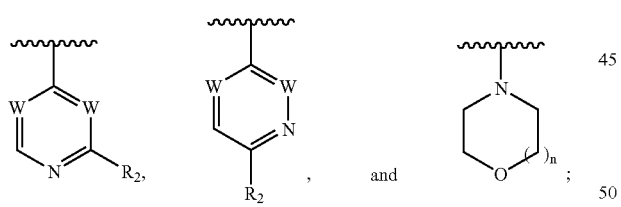
(I)

wherein:

$R_1$ is selected from the group consisting of:

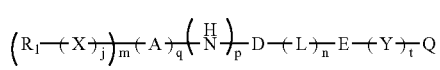

and W is CH thereof; each $R_2$ is individually selected from the group consisting of —H, alkyls, aminos, alkylaminos, arylaminos, cycloalkylaminos, halogens, alkoxys and hydroxys;

each X and Y is individually selected from the group consisting of —O—, —S—, —$NR_6$—, —$NR_6SO_2$—, —$NR_6CO$—, alkynyls, alkenyls, alkylenes, —O(CH$_2$)$_h$—, and —$NR_6$(CH$_2$)$_h$—, where each h is individually selected from the group consisting of 1, 2, 3, or 4, and where for each of alkylenes, —O(CH$_2$)$_h$—, and —$NR_6$(CH$_2$)$_h$—, one of the methylene groups present therein may be optionally double-bonded to a side-chain oxo group except that with —O(CH$_2$)$_h$—, the introduction of the side-chain oxo group does not form an ester moiety;

A is a pyrimidyl;

D is a phenyl;

E is a phenyl;

L is selected from the group consisting of —C(O)—, —S(O)$_2$—, —N($R_6$)CO—, —N($R_6$)SO$_2$—, —N($R_6$)CON($R_6$)—;

each of m, n, p and q is 1;

j is 0 or 1;

t is 0 or 1;

Q is selected from the group consisting of

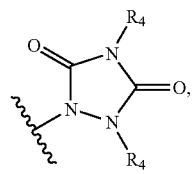
Q-3

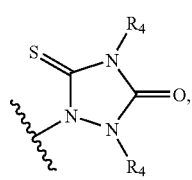
Q-4

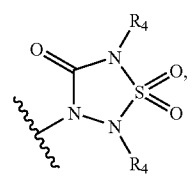
Q-5

-continued

Q-6 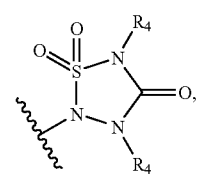

Q-7 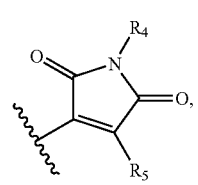

Q-9 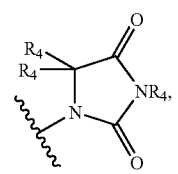

Q-12 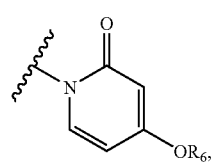

Q-13 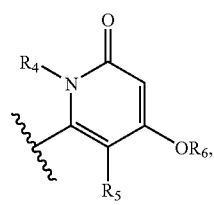

Q-14 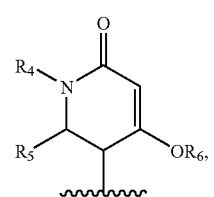

Q-18 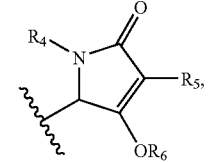

Q-20 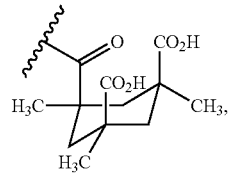

-continued

Q-28 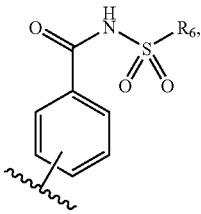

Q-29 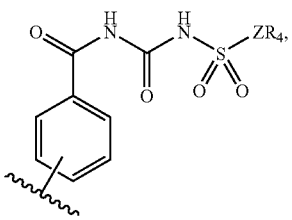

Q-30 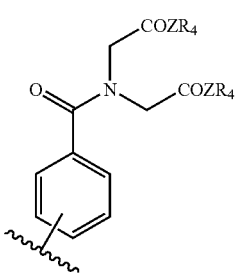

Q-31 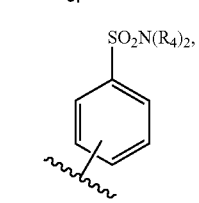

Q-32 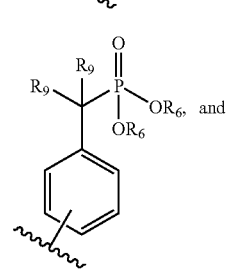

Q-35 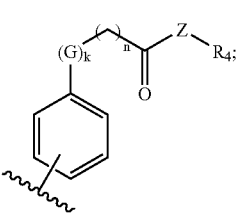

each $R_4$ group is individually selected from the group consisting of —H, alkyls, aminoalkyls, alkoxyalkyls, aryls, aralkyls, except when the $R_4$ substituent places a heteroatom on an alpha-carbon directly attached to a ring nitrogen on Q;

each $R_5$ is individually selected from the group consisting of —H, alkyls, aryls, alkylaminos, arylaminos, cycloalkylaminos, hydroxys, alkoxys, aryloxys, alkylthios, arylthios, cyanos, halogens, perfluoroalkyl, alkylcarbonyls, and nitros;

each $R_6$ is individually selected from the group consisting of —H, alkyls, allyls, and β-trimethylsilylethyl;

each $R_8$ is individually selected from the group consisting of alkyls, and aralkyls;

each $R_9$ group is individually selected from the group consisting of —H, —F, and alkyls, wherein when two $R_9$ groups are geminal alkyl groups, said geminal alkyl groups may be cyclized to form a 3-6 membered ring;

G is selected from the group consisting of —O—, —S—, and —N($R_4$)—;

k is 0 or 1;

each Z is individually selected from the group consisting of —O— and —N($R_4$)—; and each ring of formula (I) optionally includes one or more of $R_7$, where $R_7$ is a noninterfering substituent individually selected from the group consisting of—H, alkyls, aryls, alkylaminos, arylaminos, cycloalkylaminos, hydroxys, alkoxys, aryloxys, alkylthios, arthylthios, cyanos, halogens, nitros, alkylsulfinyls, alkylsulfonyls, aminosulfonyls, and perfluoroalkyls.

2. The compound of claim 1, wherein L is —NH—CO—NH— and j is 0.

3. The compound of claim 2, wherein Q is

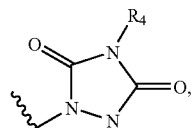

Q-3

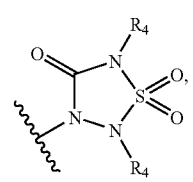

Q-5

-continued

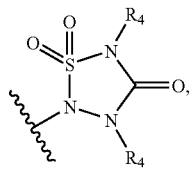

Q-6

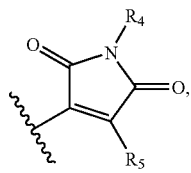

Q-7

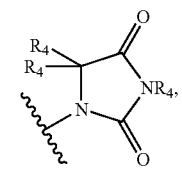

Q-9

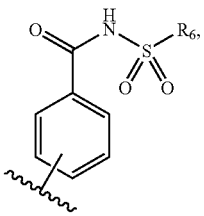

Q-28

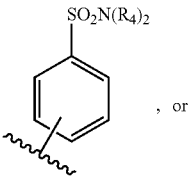

Q-31

, or

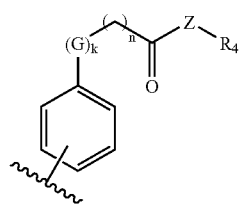

Q-35

* * * * *

SEQUENCE LISTING

<160> NUMBER OF SEQ ID NOS: 5

<210> SEQ ID NO 1

```
<211> LENGTH: 292
<212> TYPE: PRT
<213> ORGANISM: Homo sapiens

<400> SEQUENCE: 1

Gly Ala Met Asp Pro Ser Ser Pro Asn Tyr Asp Lys Trp Glu Met Glu
1               5                   10                  15

Arg Thr Asp Ile Thr Met Lys His Lys Leu Gly Gly Gly Gln Tyr Gly
            20                  25                  30

Glu Val Tyr Glu Gly Val Trp Lys Lys Tyr Ser Leu Thr Val Ala Val
        35                  40                  45

Lys Thr Leu Lys Glu Asp Thr Met Glu Val Glu Glu Phe Leu Lys Glu
50                  55                  60

Ala Ala Val Met Lys Glu Ile Lys His Pro Asn Leu Val Gln Leu Leu
65                  70                  75                  80

Gly Val Cys Thr Arg Glu Pro Pro Phe Tyr Ile Ile Thr Glu Phe Met
                85                  90                  95

Thr Tyr Gly Asn Leu Leu Asp Tyr Leu Arg Glu Cys Asn Arg Gln Glu
            100                 105                 110

Val Asn Ala Val Val Leu Leu Tyr Met Ala Thr Gln Ile Ser Ser Ala
        115                 120                 125

Met Glu Tyr Leu Glu Lys Lys Asn Phe Ile His Arg Asp Leu Ala Ala
130                 135                 140

Arg Asn Cys Leu Val Gly Glu Asn His Leu Val Lys Val Ala Asp Phe
145                 150                 155                 160

Gly Leu Ser Arg Leu Met Thr Gly Asp Thr Tyr Thr Ala His Ala Gly
                165                 170                 175

Ala Lys Phe Pro Ile Lys Trp Thr Ala Pro Glu Ser Leu Ala Tyr Asn
            180                 185                 190

Lys Phe Ser Ile Lys Ser Asp Val Trp Ala Phe Gly Val Leu Leu Trp
        195                 200                 205

Glu Ile Ala Thr Tyr Gly Met Ser Pro Tyr Pro Gly Ile Asp Leu Ser
210                 215                 220

Gln Val Tyr Glu Leu Leu Glu Lys Asp Tyr Arg Met Glu Arg Pro Glu
225                 230                 235                 240

Gly Cys Pro Glu Lys Val Tyr Glu Leu Met Arg Ala Cys Trp Gln Trp
                245                 250                 255

Asn Pro Ser Asp Arg Pro Ser Phe Ala Glu Ile His Gln Ala Phe Glu
            260                 265                 270

Thr Met Phe Gln Glu Ser Ser Ile Ser Asp Glu Val Glu Lys Glu Leu
        275                 280                 285

Gly Lys Arg Gly
    290

<210> SEQ ID NO 2
<211> LENGTH: 11
<212> TYPE: PRT
<213> ORGANISM: Homo sapiens

<400> SEQUENCE: 2

Val Glu Glu Phe Leu Lys Glu Ala Ala Val Met
1               5                   10

<210> SEQ ID NO 3
<211> LENGTH: 10
<212> TYPE: PRT
<213> ORGANISM: Homo sapiens
```

```
-continued

<220> FEATURE:
<221> NAME/KEY: MISC_FEATURE
<222> LOCATION: (1)..(11)
<223> OTHER INFORMATION: X is any amino acide

<400> SEQUENCE: 3

His Arg Asp Leu Ala Ala Arg Asn Xaa Leu
1               5                   10

<210> SEQ ID NO 4
<211> LENGTH: 9
<212> TYPE: PRT
<213> ORGANISM: Homo sapiens

<400> SEQUENCE: 4

Asp Phe Gly Leu Ser Arg Leu Met Thr
1               5

<210> SEQ ID NO 5
<211> LENGTH: 7
<212> TYPE: PRT
<213> ORGANISM: Homo sapiens

<400> SEQUENCE: 5

Gly Asp Thr Tyr Thr Ala His
1               5
```